(12) United States Patent
Amshey et al.

(10) Patent No.: US 8,845,984 B2
(45) Date of Patent: Sep. 30, 2014

(54) APPARATUS FOR AND METHOD OF PROCESSING BIOLOGICAL SAMPLES

(75) Inventors: Joseph Amshey, Encinitas, CA (US); Daniel Bezdek, Oceanside, CA (US); Espir Kahatt, Carlsbad, CA (US); Alexander Khorlin, Mountain View, CA (US); Lance Parsons, San Marcos, CA (US); Todd Peterson, Coronado, CA (US); Timothy Powers, Carlsbad, CA (US); Michael Thacker, San Diego, CA (US); Timothy Updyke, Temecula, CA (US); Kornelija Zgonc, Carlsbad, CA (US)

(73) Assignee: Life Technologies Corporation, Carlsbad, CA (US)

( * ) Notice: Subject to any disclaimer, the term of this patent is extended or adjusted under 35 U.S.C. 154(b) by 0 days.

(21) Appl. No.: 13/615,500

(22) Filed: Sep. 13, 2012

(65) Prior Publication Data

US 2013/0040376 A1 Feb. 14, 2013

Related U.S. Application Data

(63) Continuation of application No. 12/549,311, filed on Aug. 27, 2009, now Pat. No. 8,404,198.

(60) Provisional application No. 61/139,539, filed on Dec. 19, 2008, provisional application No. 61/108,019, filed on Oct. 23, 2008, provisional application No. 61/098,586, filed on Sep. 19, 2008, provisional application No. 61/092,338, filed on Aug. 27, 2008.

(51) Int. Cl.
*B01L 9/00* (2006.01)
*B01L 3/00* (2006.01)
*B01L 7/00* (2006.01)
*G01N 35/00* (2006.01)
*G01N 35/10* (2006.01)

(52) U.S. Cl.
CPC ....... *B01L 3/502715* (2013.01); *B01L 2200/10* (2013.01); *B01L 7/00* (2013.01); *B01L 2200/025* (2013.01); *B01L 2200/16* (2013.01); *B01L 2300/088* (2013.01); *B01L 9/527* (2013.01); *B01L 2400/0481* (2013.01); *B01L 2400/0487* (2013.01); *B01L 2200/0689* (2013.01); *B01L 2300/0681* (2013.01); *B01L 2200/027* (2013.01); *B01L 2400/0605* (2013.01); *B01L 2300/123* (2013.01); *B01L 2300/0636* (2013.01); *B01L 2300/0867* (2013.01); *G01N 2035/00306* (2013.01); *G01N 2035/1037* (2013.01); *B01L 2400/0655* (2013.01)
USPC ................ 422/561; 422/63; 422/64; 422/65; 422/66; 422/67; 436/180

(58) Field of Classification Search
USPC ................ 422/50, 500, 561, 63–67; 436/180
See application file for complete search history.

(56) References Cited

U.S. PATENT DOCUMENTS

| | | |
|---|---|---|
| 4,118,280 A | 10/1978 | Charles |
| 5,779,868 A | 7/1998 | Parce et al. |
| 5,990,301 A | 11/1999 | Colpan et al. |
| 6,066,243 A | 5/2000 | Anderson et al. |
| 6,242,220 B1 | 6/2001 | Wahle et al. |
| 6,297,371 B1 | 10/2001 | Colpan et al. |
| 6,767,733 B1 | 7/2004 | Green |
| 6,914,137 B2 | 7/2005 | Baker |
| 7,105,225 B2 | 9/2006 | Birkholz et al. |
| 7,109,322 B2 | 9/2006 | Colpan et al. |
| 7,214,508 B2 | 5/2007 | Hucklenbroich et al. |
| 7,479,256 B1 | 1/2009 | Gruhler et al. |
| 7,723,099 B2 * | 5/2010 | Miller et al. ............... 435/287.1 |
| 2001/0051377 A1 | 12/2001 | Hammer et al. |
| 2002/0039783 A1 * | 4/2002 | McMillan et al. ......... 435/287.2 |
| 2002/0051737 A1 | 5/2002 | Sollböhmer et al. |
| 2003/0224523 A1 | 12/2003 | Thornberg et al. |
| 2003/0230488 A1 | 12/2003 | Lee et al. |
| 2004/0166504 A1 | 8/2004 | Rossier et al. |
| 2004/0203055 A1 | 10/2004 | Kennedy et al. |
| 2004/0208794 A1 | 10/2004 | Karg et al. |
| 2005/0016852 A1 | 1/2005 | Amirkhanian et al. |

| | | | |
|---|---|---|---|
| 2006/0154247 | A1 | 7/2006 | Baker et al. |
| 2006/0257993 | A1 | 11/2006 | McDevitt et al. |
| 2007/0048188 | A1 | 3/2007 | Bigus |
| 2007/0092410 | A1 | 4/2007 | Ricker et al. |
| 2007/0117972 | A1 | 5/2007 | Halaka |
| 2007/0263046 | A1 | 11/2007 | Iwasa et al. |
| 2008/0083263 | A1 | 4/2008 | Philipp et al. |
| 2008/0182301 | A1 | 7/2008 | Handique et al. |
| 2008/0200343 | A1 | 8/2008 | Clemens et al. |
| 2008/0217246 | A1 | 9/2008 | Benn et al. |
| 2009/0155123 | A1 | 6/2009 | Williams et al. |
| 2010/0120129 | A1 | 5/2010 | Amshey et al. |

FOREIGN PATENT DOCUMENTS

| | | |
|---|---|---|
| CN | 201094106 | 7/2008 |
| EP | 0763739 | 3/1997 |
| EP | 0802413 | 10/1997 |
| EP | 0865824 | 9/1998 |
| EP | 0965842 | 12/1999 |
| EP | 1385006 | 1/2004 |
| JP | 2002065242 | 3/2002 |
| JP | 2006003145 | 1/2006 |
| JP | 2006149215 | 6/2006 |
| JP | 2006308428 | 11/2006 |
| JP | 2007187674 | 7/2007 |
| KR | 100710122 | 4/2007 |
| WO | WO93/20440 | 10/1993 |
| WO | WO94/18565 | 8/1994 |
| WO | WO96/12958 | 5/1996 |
| WO | WO00/76663 | 12/2000 |
| WO | WO2004/032044 | 4/2004 |
| WO | WO2004/092721 | 10/2004 |
| WO | WO2006/065598 | 6/2006 |
| WO | WO2006/099255 | 9/2006 |
| WO | WO2008/030631 | 3/2008 |
| WO | WO2009/108260 | 9/2009 |
| WO | WO2010/025302 | 3/2010 |
| WO | WO2010/130762 | 11/2010 |

OTHER PUBLICATIONS

Invitrogen, BenchPro (TM) 4100 Western Processing System Product Literature, Invitrogen Website: http://www.invitrogen.com/site/us/en/home/Products-and-Services/Applications/Protein-Expression-and-Analysis/Western-Blotting/BenchPro4100.html. Oct. 23, 2008, 2.

* cited by examiner

*Primary Examiner* — Jyoti Nagpaul

(74) *Attorney, Agent, or Firm* — Life Technologies Corporation

(57) ABSTRACT

The present invention provides systems, devices, apparatuses and methods for automated bioprocessing. Examples of protocols and bioprocessing procedures suitable for the present invention include but are not limited to: immunoprecipitation, chromatin immunoprecipitation, recombinant protein isolation, nucleic acid separation and isolation, protein labeling, separation and isolation, cell separation and isolation, food safety analysis and automatic bead based separation. In some embodiments, the invention provides automated systems, automated devices, automated cartridges and automated methods of western blot processing. Other embodiments include automated systems, automated devices, automated cartridges and automated methods for separation, preparation and purification of nucleic acids, such as DNA or RNA or fragments thereof, including plasmid DNA, genomic DNA, bacterial DNA, viral DNA and any other DNA, and for automated systems, automated devices, automated cartridges and automated methods for processing, separation and purification of proteins, peptides and the like.

14 Claims, 53 Drawing Sheets

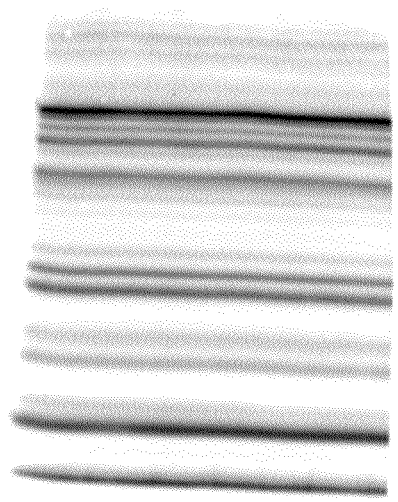 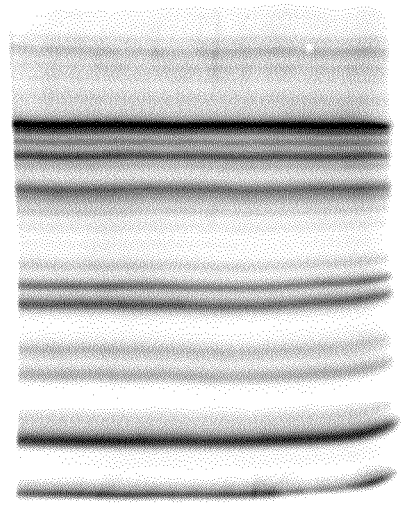
FIGURE 27A    FIGURE 27B
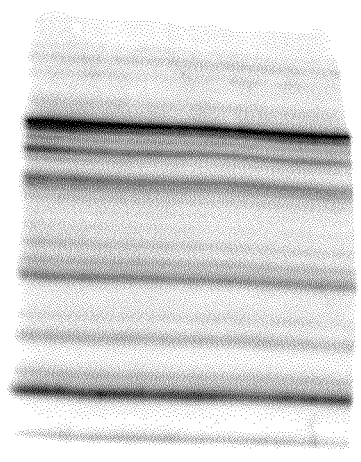 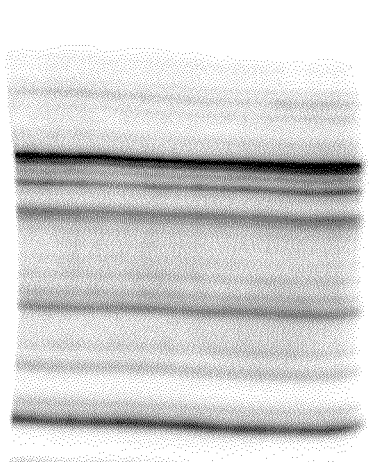
FIGURE 27C    FIGURE 27D

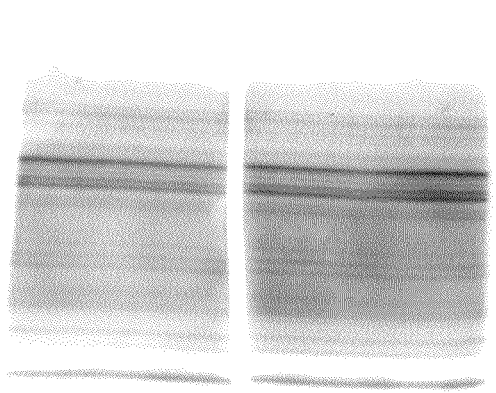
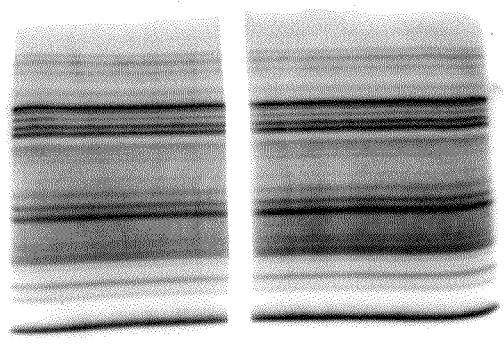
FIGURE 31A    FIGURE 31B        FIGURE 31C    FIGURE 31D
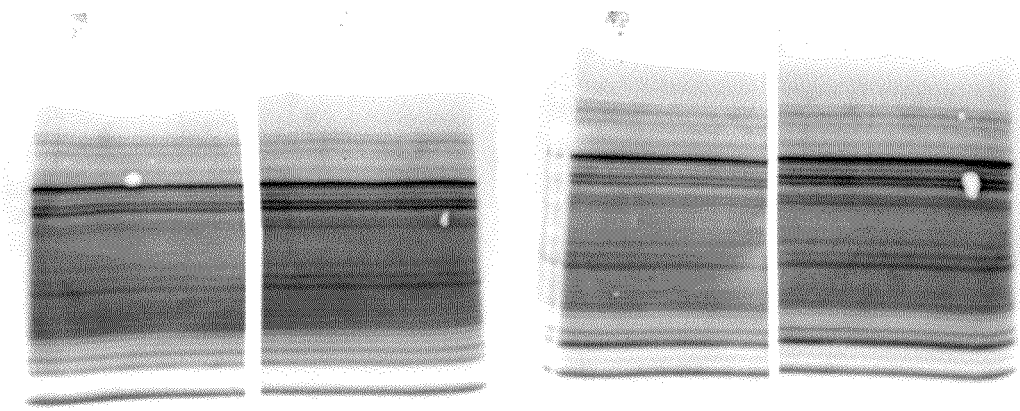
FIGURE 32A    FIGURE 32B        FIGURE 32C    FIGURE 32D

APPARATUS FOR AND METHOD OF PROCESSING BIOLOGICAL SAMPLES

CROSS-REFERENCE TO RELATED APPLICATIONS

This application is Continuation of U.S. application Ser. No. 12/549,311 filed Aug. 27, 2009, which claims priority to U.S. Application No. 61/139,539 filed Dec. 19, 2008; U.S. Application No. 61/108,019 filed Oct. 23, 2008; U.S. Application No. 61/098,586 filed Sep. 19, 2008; and U.S. Application No. 61/092,338 filed Aug. 27, 2008, which disclosures are herein incorporation by reference in their entirety.

FIELD OF THE INVENTION

The invention relates to apparatuses and methods for processing biomolecules and more specifically to automated methods and apparatuses for processing biomolecules.

BACKGROUND OF THE INVENTION

Certain laboratory procedures remain predominantly carried out using inefficient manual methods which require individual attention by the scientist or lab technician performing the procedure. Many of these procedures would benefit from automation. For example, nucleic acid purification, such as plasmid preparation is currently a time consuming, inefficient task that has not yet been automated. Gradual improvements such as the introduction of precipitation filters have reduced the hands-on time required, however even the most advanced nucleic acid purification kits still require several hours and individual attention. Similarly, processing for western blot analysis can be a labor intensive process that requires the scientist or lab technician to be tied to the bench during the process. In addition, such processes suffer from human error and lack of reproducibility inherent in manually intensive procedures. What is needed, and what is provided herein, in part, is a small, affordable, user-friendly and flexible instrument for reactions performed on solid supports, preproteomics sample preparation, nucleic acid applications, and cell separation applications with increased convenience of use, reduced labor time, decreased error, and increased reproducibility.

SUMMARY OF THE INVENTION

In some embodiments, the present invention provides systems, devices, apparatuses and methods for automated bioprocessing. Examples of protocols and bioprocessing procedures suitable for the present invention include but are not limited to: immunoprecipitation, chromatin immunoprecipitation, recombinant protein isolation, nucleic acid separation and isolation, protein labeling, separation and isolation, cell separation and isolation, and automatic bead based separation. In a particular embodiment, the invention provides automated systems, automated devices, automated cartridges and automated methods of western blot processing. Other embodiments include automated systems, automated devices, automated cartridges and automated methods for separation, preparation and purification of nucleic acids, such as DNA or RNA or fragments thereof, including plasmid DNA, genomic DNA, bacterial DNA, viral DNA and any other DNA or fragments thereof, and for automated systems, automated devices, automated cartridges and automated methods for processing, separation and purification of proteins, peptides and the like.

In some embodiments, an automated bioprocessing system includes a bioprocessing device, at least one bioprocessing cartridge, a fluid supply and a computer control system for controlling at least one parameter associated with bioprocessing using the bioprocessing cartridge. In some embodiments, an automated bioprocessing system may include multiple bioprocessing cartridges.

In some embodiments, automated bioprocessing devices include one or more cartridge slots, each slot configured to receive a bioprocessing cartridge; a removable fluid container tray comprising multiple fluid container holders configured to hold fluid containers for use during bioprocessing and a computer control system, configured to control at least one parameter associated with bioprocessing in the one or more bioprocessing cartridges.

In some embodiments, automated bioprocessing devices include a fluid manifold configured to fluidly connect one or more fluid containers within a fluid container holder with one or more process fluid connectors. In some embodiments, the automated bioprocessing devices may include a fluid manifold configured to connect one or more control fluid connectors on a bioprocessing cartridge to one or more control fluid supplies.

In some embodiments, the automated bioprocessing cartridges include at least one bioprocessing chamber configured to contain a solid support, the cartridge further including a plurality of mesoscale and/or microscale fluid flow channels in fluid communication with the bioprocessing chamber through at least one pump.

In some embodiments, the automated methods of bioprocessing include providing a bioprocessing cartridge comprising at least one bioprocessing chamber containing a solid support and a plurality of mesoscale and/or microscale fluid flow channels in fluid communication with the bioprocessing chamber, and pumping at least one processing fluid through at least one of the plurality of mesoscale or microscale fluid flow channels and into the bioprocessing chamber.

In some embodiments, provided herein is a bioprocessing cartridge comprising at least one bioprocessing chamber configured to contain a blotting membrane, a plurality of mesoscale and/or microscale process fluid channels in fluid communication with the bioprocessing chamber, and a plurality of built-in pumps, configured for pumping fluid through the process fluid channels. The diameter of the process fluid channels may be in the range of between about 10 um and about 10 mm, between about 100 um and about 5 mm, between about 250 um and about 2.5 mm, between about 500 um and about 2 mm, or about 1 mm in diameter. The cartridge may be a plastic cartridge. The cartridge may further comprise no flexible tubing. In some embodiments, the cartridge may comprise at least one access valve within a flow path defined by at least one of the plurality of process fluid channels. Each of the at least one access valves may be located within a flow bath between at least one process fluid connector and the at least one of the plurality of process fluid channels, each process fluid connector configured to fluidly connect the cartridge to one or more fluid containers. In some embodiments, the cartridge may include more than one access valve, wherein each access valve may be placed within a flow path between and independent process fluid connector and one of the plurality of process fluid channels, each independent process fluid connector configured to fluidly connect the cartridge to one or more fluid containers. The process fluid connectors may be a plurality of connectors, such as for example, between 2 and 20 aspiration and/or expiration tubes, between 2 and 10 aspiration and/or expiration tubes, or between 4 and 8 aspiration and/or expiration tubes. In some embodiments, the cartridge may comprise an access valve within each of the flow paths between each of the process fluid connectors and each of the plurality of process fluid channels. In some embodiments, the cartridge may comprise an access valve within each of the flow paths between each of the process fluid connectors and each of the plurality of process fluid channels. In some embodiments, the cartridge may include a blotting membrane within the bioprocessing chamber. The blotting membrane may be a Western blotting membrane. The shape of the cartridge may vary. In some embodiments of the cartridge, the depth may be in the range of between about 2 mm to about 5 cm, between about 4 mm to about 4 cm, between about 5 mm to about 2 cm, between about 8 mm to about 1.5 cm, between about 9 mm to about 1.2 cm, about 1 cm, or 1 cm. The height of the cartridge may be in the range of between about 10 cm and about 25 cm, between about 12 cm and about 20 cm, between about 14 cm and about 18 cm, between about 15 cm and about 17 cm, about 16 cm, or 16 cm. The width of the cartridge at its greatest may be in the range of between about 10 cm and about 25 cm, between about 12 cm and about 22 cm, between about 16 cm and about 20 cm, between about 17 cm and about 19 cm, about 18 cm, 18 cm, or about 18.2 cm, or 18.2 cm. In some embodiments, the cartridge may have a rectangular shape or a square shape. The process fluid connectors may be in the range of between about 10 um and about 10 mm in diameter, between about 100 um and about 5 mm in diameter, between about 250 um and about 2.5 mm in diameter, between about 500 um and about 2.0 mm in diameter, or about 1 mm in diameter. The cartridge in some embodiments, may be enclosed by a package. In some embodiments, the at least one process fluid connector may have a diameter that tapers to a smaller inner diameter at its distal end. In some embodiments, the inside diameter of the at least one process fluid connector closest (proximal) to the process fluid channel, is about 0.5 mm to about 15 mm, about 1 mm to about 10 mm, about 2 mm to about 6 mm, about 4 mm, or 4 mm, and the inside diameter of the end of the at least one process fluid connectors furthest (distal) from the process fluid channel, has an inner diameter of between about 10 μm and about 10 mm, between about 100 μm and about 5 mm, between about 250 μm and about 2.5 mm, between about 500 μm and about 2.0 mm in diameter, or about 1 mm in diameter. The cartridge may comprise any combination of elements as provided in the specification.

Provided herein, in some embodiments, is an automated blot processing device comprising: one or more cartridge slots, each slot configured to receive a bioprocessing cartridge, and an automated control system, configured to control at least one step associated with processing a blotting membrane within the bioprocessing cartridge in a blotting protocol. In some embodiments, the device may comprise between about 1 to about 8, between about 2 to about 6, between about 3 to about 5, or 4 cartridge slots. In some embodiments, the device may further comprise a bioprocessing cartridge. The bioprocessing cartridge may include a blot, wherein the blot is a western blot, and the blotting protocol is a western blot processing protocol. In some embodiments the blot processing device may further comprise a blotting membrane within the bioprocessing cartridge. The automated control system may be configured to automatically control most steps, all steps or all steps except one, two, three, or four steps of a blot processing protocol, such as a western blot processing protocol. In some embodiments, the automated blot processing device may include an automated control system configured to eliminate the need for all, all but 1, all but 2, or all but 3 steps of a blot processing protocol, such as a western blot processing protocol. The automated blot processing device may be any device according to any of the embodiments of the device provided herein. The automated blot processing device may use any bioprocessing cartridge described herein in the specification.

In some embodiments, an automated method of bioprocessing includes: a) inserting at least one bioprocessing cartridge into an automated bioprocessing device, said bioprocessing cartridge comprising: i) at least one bioprocessing chamber containing a solid support therein; and ii) a plurality of mesoscale and/or microscale channels in fluid connection with to said bioprocessing chamber; and b) initiating a bioprocessing protocol on said bioprocessing device, said protocol comprising one or more of the following: i) controlling pumps and valves on said bioprocessing cartridge to supply reagents and/or samples from one or more containers to the at least one bioprocessing chamber of each of the at least one bioprocessing cartridges, ii) controlling pumps and valves on said bioprocessing cartridge to recirculate the reagents and or samples across the at least one bioprocessing chamber of each of the at least one bioprocessing cartridges; and/or iii) controlling pumps and valves on said bioprocessing cartridge to remove reagents and/or samples from the at least one bioprocessing chamber of each of the at least one bioprocessing cartridges.

In some embodiments, the methods include methods of applying one or more fluids to a solid support comprising: a) inserting at least one bioprocessing cartridge into an automated bioprocessing device, said bioprocessing cartridge comprising: i) at least one bioprocessing chamber containing a solid support therein; and ii) a plurality of mesoscale and/or microscale channels in fluid communication with the at least one bioprocessing chamber; b) performing a pumping sequence on the cartridge, wherein the pumping sequence includes one or more fluid addition cycles wherein fluid is pumped from one or more containers through at least one of the plurality of mesoscale and/or microscale channels and into the at least one chamber.

Provided herein are automated methods of processing a blot comprising a) providing a bioprocessing cartridge according to any embodiment of the bioprocessing cartridge described herein, wherein the bioprocessing cartridge contains a blotting membrane; and pumping at least one process fluid through at least one of said plurality of process fluid channels and into said bioprocessing chamber. In some embodiemtns, the method may be performed by a device according to any of the bioprocessing devices described herein. The method may comprise all the steps, all but one step, all but two steps, or all but three of the steps of a blotting protocol performed on the blotting membrane by the device.

In some embodiments, the automated bioprocessing systems, automated bioprocessing devices, automated bioprocessing cartridges, and automated bioprocessing methods comprise western blot processing systems, western blot processing devices, western blot processing cartridges, and western blot processing methods.

In some embodiments, the automated bioprocessing systems, automated bioprocessing devices, automated bioprocessing cartridges, and automated bioprocessing methods comprise nucleic acid separation, purification and/or collection systems, nucleic acid separation, purification and/or collection devices, nucleic acid separation, purification and/or collection cartridges, and nucleic acid separation, purification and/or collection methods.

Further provided herein is a kit comprising any of the bioprocessing cartridges described herein in. The kit may further include one or more tubes, containers, or any other suitable fluid reservoirs.

Provided herein is a bioprocessing cartridge comprising at least one bioprocessing chamber configured to contain a solid support and a plurality of mesoscale and/or microscale process fluid channels in fluid communication with the bioprocessing chamber through at least one pump, wherein the at least one pump is included in or on the bioprocessing cartridge. In some embodiments, the cartridge may include at least one access valve within a flow path defined by at least one of the plurality of process fluid channels. Each of said at least one access valves may be located within a flow path between a process fluid connector and the at least one of the plurality of process fluid channels, each process fluid connector configured to fluidly connect the cartridge to one or more fluid containers. In some embodiments, the cartridge may include more than one access valve, wherein each access valve is placed within a flow path between an independent process fluid connector and one of the plurality of process fluid channels, each independent process fluid connector configured to fluidly connect the cartridge to one or more fluid containers. In some embodiments, the process fluid connectors may be configured to connect to said fluid containers via a manifold. In some embodiments, the process fluid connectors are configured to connect to said fluid containers via aspiration and/or expiration tubes. In some embodiments, the process fluid connectors may be aspiration and/or expiration tubes. In some embodiments, the cartridge may include an access valve within each of the flow paths between each of the process fluid connectors and each of the plurality of process fluid channels. The solid support may be selected from the group consisting of: blotting membranes, filter cassettes, filter membranes, filter papers, solid phase extraction cassettes, solid phase extraction disks, pluralities of beads, including magnetic beads, and combinations thereof. In some embodiments, the bioprocessing cartridge may include at least one, at least two, or at least three process valves in a flow path between the pump and the chamber. In some embodiments, the at least one of said process valves or said access valves includes an actuator to close the valve and/or to open the valve. In some embodiments, at least one of the process valves and/or access valves may include a check valve. In some embodiments, the bioprocessing cartridge may include two or more, or three or more bioprocessing chambers. In some embodiments, the cartridge may further include a plurality of control fluid channels. In some embodiments, the cartridge may further include control fluid connectors connecting to each of said plurality of control fluid channels, each control fluid connector configured to fluidly connect the cartridge to one or more automated control systems. In some embodiments, the automated control system controls the opening and closing of the process valves and the access valves and controls the at least one pump. In some embodiments, the cartridge may include a dye chamber in fluid communication with at least one process fluid channel, wherein a material within said dye chamber changes color when contacted with a fluid. In some embodiments, the cartridge may include a multi-use cartridge. The processing chambers may, in some embodiments, be configured to provide access to the processing chambers by a user. In some embodiments, the cartridge is a single use cartridge.

Further provided herein is an automated bioprocessing device comprising one or more cartridge slots, each slot configured to receive a bioprocessing cartridge, a removable fluid container tray comprising at least one fluid container holder configured to hold containers for use during bioprocessing, and an automated control system, configured to control at least one parameter associated with bioprocessing in one or more bioprocessing cartridges. The device may include 2 to 8 cartridge slots or 2 to 4 cartridge slots. In some embodiments, the cartridge slots may further include a fluid manifold configured to fluidly connect one or more fluid containers within the fluid container holder with one or more process fluid connectors and/or a control fluid manifold configured to connect one or more control fluid connectors to one or more automated control systems. The manifold may be configured to connect one or more control fluid connectors to one or more automated control systems. In some embodiments, the one or more automated control systems includes a vacuum supply and an air pressure supply. The vacuum supply and/or said air pressure supply may be included within the device. Alternatively, the vacuum supply and/or said air pressure supply may be external to the device. In some embodiments the vacuum supply may include a vacuum pump. In some embodiments, the air pressure supply may include a compressor. In some embodiments, the cartridge slots may include multiple openings or guide features for receiving aspiration and/or expiration tubes on a cartridge and guiding the aspiration and/or expiration tubes into fluid containers in the fluid container holders. In some embodiments of the device, the device may include at least one removable fluid container tray includes a set of fluid container holders or reservoirs configured to supply reagents and/or samples to each bioprocessing cartridge in each cartridge slot. The set of fluid container holders further comprises containers configured to receive fluids from or supply fluids to each of multiple bioprocessing cartridges. In some embodiments, the bioprocessing device may include a GUI. In some embodiments, the automated control system may independently provide for control of the pumps and the valves on bioprocessing cartridges in each of the cartridge slots. In some embodiments, the automated control system may provide for user input of one or more control parameters, user selection of pre-programmed protocols and/or user creation and storage of protocols.

Further provided herein a method of using an automated method of bioprocessing comprising: providing a bioprocessing cartridge comprising at least one bioprocessing chamber containing a solid support therein, and a plurality of mesoscale and/or microscale process fluid channels in fluid communication with said bioprocessing chamber, and pumping at least one process fluid through at least one of said plurality of process fluid channels and into said bioprocessing chamber. In some embodiments, the pumping may include pumping one or more reagents and/or a sample into said processing chamber and into contact with the solid support. Additionally, the pumping may include circulating at least one of said reagents from a channel accessing an upper portion of said chamber through a pump on said cartridge and into a channel accessing a bottom portion of said chamber. In some embodiments of the method, the pumping includes pumping at least one process fluid through or across the surface of a filter or membrane in said at least one bioprocessing chamber. In some embodiments, the filter or membrane may include a blot membrane. In some embodiments, the blot membrane may be held by a blot membrane holder within the bioprocessing chamber. In some embodiments, the filter or membrane may include a western blot membrane. In some embodiments, the filter or membrane may include a cell separation membrane. In some embodiments, the filter or membrane may include a lysate filter. In some embodiments, the at least one process fluid may include at least one blocking buffer. The at least one process fluid may include at least one antibody and/or at least one washing fluid. In some embodiments of the method, the pumping may include: a) adding a blocking buffer to the bioprocessing chamber, b) recirculating the blocking buffer across a blot membrane to form a blocked blot membrane, c) adding at least one antibody solution to the bioprocessing chamber, and d) recirculating the at least one antibody solution across said blocked blot membrane. The recirculating at least one antibody solution across said blocked blot membrane may include: a) recirculating a primary antibody solution across said blocked blot membrane, b) washing the blot membrane, c) adding a secondary antibody solution to the bioprocessing chamber; and d) recirculating the secondary antibody solution across the washed blot membrane. In some embodiments of the method the pumping may include pumping at least one process fluid through at least one solid phase extraction membrane, at least one solid phase extraction cassette or at least one solid phase extraction disk in at least one bioprocessing chamber. In some embodiments of the method, the solid phase extraction membrane, solid phase extraction cassette or solid phase extraction disk may include a silica reversible binding ligand. In some embodiments, the pumping may include pumping cell culture media across a cell separation filter to separate cells from the cell culture media, wherein said cells are captured on the filter. In some embodiments, the pumping may further include: a) resuspending the captured cells in a resuspension buffer, b) lysing the cell in a lysing solution to form a lysate, c) neutralizing the lysate; and d) clarifying the lysate. The cells may be resuspended and pumped out of the bioprocessing chamber and into a container containing a lysing solution. In some embodiments, the clarifying the lysate may include pumping the lysate through a filter or membrane to remove unwanted cellular molecules. In some embodiments of the method, the pumping may further include: a) extracting at least one biomolecule in a bioprocessing chamber containing a binding membrane, b) washing the binding membrane; and c) eluting the biomolecule from the binding membrane. In some embodiments of the method, the pumping may further include precipitating the biomolecule in a bioprocessing chamber containing a precipitation filter. In some embodiments of the method, the method may further include pretreating the sample prior to the pumping. In some embodiments, the pretreating may include adding a salt solution to a sample. In some embodiments, the salt solution may be NaCl.

Further provided herein is an automated method of bioprocessing comprising: a) inserting at least one bioprocessing cartridge into a bioprocessing device, said bioprocessing cartridge comprising: i) at least one bioprocessing chamber containing a solid support therein, and ii) a plurality of mesoscale and/or microscale channels in fluid communication with said bioprocessing chamber, b) initiating a bioprocessing protocol on said bioprocessing device, said protocol comprising one or more of the following: i) controlling pumps and valves on said bioprocessing cartridge to supply reagents and/or samples from one or more containers to the at least one bioprocessing chamber of each of the at least one bioprocessing cartridges, ii) controlling pumps and valves on said bioprocessing cartridge to recirculate the reagents and or samples across the at least one bioprocessing chamber of each of the at least one bioprocessing cartridges; and/or iii) controlling pumps and valves on said bioprocessing cartridge to remove reagents and/or samples from the at least one bioprocessing chamber of each of the at least one bioprocessing cartridges.

Provided herein is a method of applying one or more fluids to a solid support comprising: a) inserting at least one bioprocessing cartridge into a bioprocessing device, said bioprocessing cartridge including: i) at least one bioprocessing chamber containing a solid support therein; and ii) a plurality of mesoscale and/or microscale channels in fluid communication with said bioprocessing chamber; b) performing a pumping sequence on said cartridge, wherein said pumping sequence comprises entering one or more fluid addition cycles wherein fluid is pumped from the one or more containers through one of the fluid flow channels and into the chamber; wherein the fluid added in any of the fluid addition cycles is the same or different than fluid added in any other of the fluid addition cycles. In some embodiments, the pumping sequence may further include entering a purging cycle following each fluid addition cycle comprising pumping fluid within the chamber into a designated waste container. In some embodiments of the method, the pumping sequence further comprises entering a circulating cycle after any of the fluid addition cycles, wherein said circulating cycle comprises opening a valve in a fluid flow channel connected to the bottom of the chamber and pumping fluid from the bottom portion of the chamber through one or more fluid flow channels and into a top portion of the chamber. In some embodiments of the method, the method may further include initiating and terminating the pumping sequence using a programmable controller. In some embodiments, the method may further include independently opening and closing valves in each of the process fluid connectors to selectively control the amount of fluid entering or leaving the fluid flow channels. In some embodiments, the method may further include inserting multiple cartridges into the cartridge slots and performing a pumping sequence on each of the cartridges, wherein the pumping sequence performed on each cartridge is the same or different than the pumping sequence performed on any other cartridge. The pumping sequences performed on each of the cartridges may be performed at the same time. In some embodiments, the method may further include initiating and terminating the pumping sequence on each of the cartridges using a programmable controller. In some embodiments, the controller may be a central processing unit of a computer. In some embodiments, the method may further include storing one or more selectable programs on said controller. In some embodiments, the method may further include initiating a designated pumping sequence by selecting a program stored on said controller. In some embodiments, the method may further include displaying the one or more selectable programs on a GUI.

Further provided herein is an automated bioprocessing system comprising: a) a bioprocessing device comprising: i) one or more cartridge slots, each slot configured to receive a bioprocessing cartridge, and ii) an automated control system, configured to control at least one parameter associated with bioprocessing in one or more bioprocessing cartridges, and b) one or more bioprocessing cartridges comprising i) at least one bioprocessing chamber configured to contain a solid support, ii) a plurality of mesoscale and/or microscale process fluid channels in fluid communication with the bioprocessing chamber through at least one pump, wherein the at least one pump is included in or on the bioprocessing cartridge.

As used herein, card, cartridge, bioprocessing card and bioprocessing cartridge are intended to be interchangeable. Further provided herein is a cartridge, device, or method of any of the prior embodiments described herein, wherein the blot comprises proteins or nucleic acids.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIGS. 27A-27D shows the results of the western blots performed as described in Examples 10A and 10B and Examples 11A and 11B;

FIGS. 31A-31D shows the results of the western blots performed as described in Examples 16A and 16B and Examples 15A and 15B;

FIGS. 32A-32D shows the results of the western blots performed as described in Examples 18A and 18B and Examples 17A and 17B

DETAILED DESCRIPTION

Figure 1A:
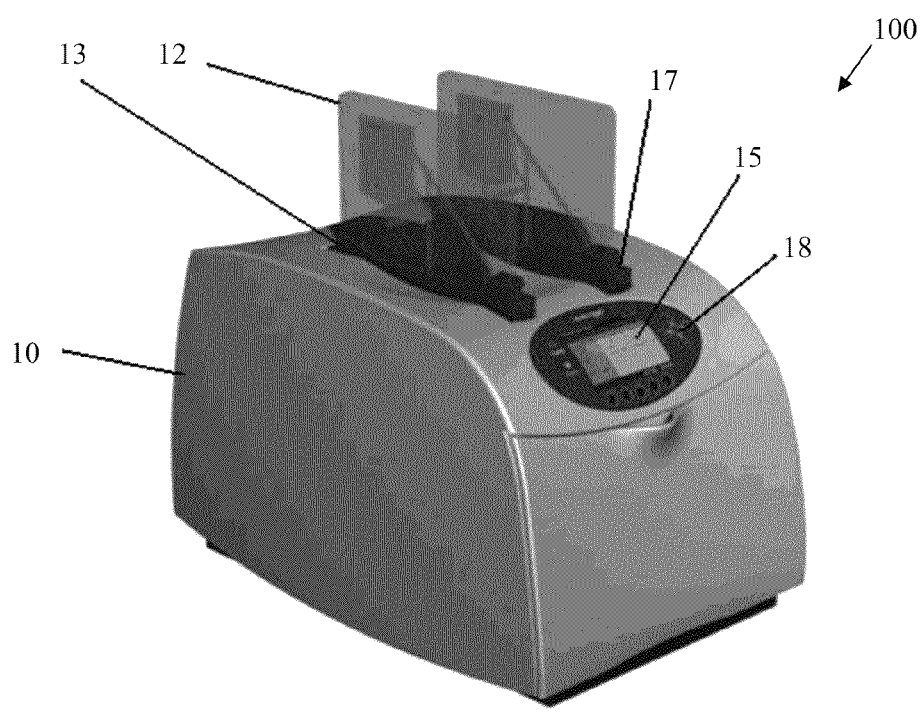
FIGS. 1A-1D depict alternate embodiments of a bioprocessing device.

The automated bioprocessing systems, automated bioprocessing devices, automated bioprocessing cartridges and automated bioprocessing methods disclosed herein include automated bioprocessing systems, automated bioprocessing devices, automated bioprocessing cartridges and automated bioprocessing methods for performing one or more protocols for processing biomolecules, such as for performing bioprocessing procedures selected from: immunoprecipitation, chromatin immunoprecipitation, recombinant protein isolation, nucleic acid separation and isolation, protein labeling, separation and isolation, cell separation and isolation, food safety analysis, and automatic bead based separation, including automatic magnetic bead based separations. In some embodiments, the bioprocessing system may include the use of labeled molecules, wherein the labels include, for example, immunofluorescence or fluorescent labels, including Qdot® nanocrystals or Alexa Fluor® dyes. In some embodiments, the protocols for processing biomolecules are protocols for processing biomolecules that are immobilized on a solid support, such as a blotting membrane with bound biomolecules. As such, the protocols can be protocols for processing Western blots (i.e., immunoblots), Northern blots, or Southern blots. The automated bioprocessing systems, automated bioprocessing devices, automated bioprocessing cartridges and automated bioprocessing methods disclosed herein provide for automated "hands-off" bioprocessing once a protocol is initiated on a bioprocessing device, while delivering performance that: is at least as good, if not better than similar manual processing; minimizes contamination/cleanup; and/or increases efficiency and flexibility.

I. Bioprocessing Devices

In some embodiments, the automated bioprocessing devices provided herein comprise automated devices for performing one or more protocols for processing biomolecules. In some embodiments, the bioprocessing devices may be configured to run protocols and bioprocessing procedures selected from: immunoprecipitation, chromatin immunoprecipitation, recombinant protein isolation, nucleic acid separation and isolation, protein labeling, separation and isolation, cell separation and isolation, food safety and automatic bead based separation, including automatic magnetic bead based separation.

In some embodiments, the automated bioprocessing devices include one or more slots, such as two or more, three or more, four or more, five or more, or six or more slots for receiving bioprocessing cartridges. Each slot may independently be configured to receive and/or support a bioprocessing cartridge within the device and to provide for fluid connection of the cartridge to one or more fluid containers that may be used with the device. Each slot may further include a cartridge holder. In some embodiments, the slots each include a fluid manifold for connecting the bioprocessing cartridges to one or more process fluid supplies. In some embodiments, the slots include openings for receiving a cartridge and may guide one or more aspiration/expiration tubes into one or more process fluid containers, such as one or more process fluid containers placed in or included within the device. In some embodiments, each of the slots comprise a single opening that includes at least one guide, such as a projection or groove on one or both sides of the slot and/or cartridge holder that guide one or more aspiration/expiration tubes into one or more process fluid containers, such as one or more process fluid containers placed in or included within the device. In some embodiments, the aspiration/expiration tubes are integral to the bioprocessing cartridges or may be attached to fluid connectors on the bioprocessing cartridges. Each aspiration/expiration tube may be sized appropriately to serve the function with which it is identified according to bioprocessing protocols included on the central processing unit on the device or according to user selected protocols. The aspiration/expiration tubes may be the same length or may vary in length, with respect to each other.

In some embodiments, each of the slots provides for connection of one or more control fluid supplies to bioprocessing cartridges placed within the slots. Such connections, may, for example, include connection of a control fluid manifold to a cartridge inserted in each slot. In some embodiments, the control fluid manifold is configured to form a sealed connection with control fluid connectors on a bioprocessing cartridge within the slot. In some embodiments, the control fluid manifold is connected or sealed to the bioprocessing cartridge, in part, by using a gasket or O-ring, or other suitable sealing mechanism. The control fluid manifold may include individual supply connectors for interacting with each of the control fluid connectors on a bioprocessing cartridge. In some embodiments, the control fluid manifolds are reconfigurable, removable and/or replaceable to provide for alternative configurations of the control fluid connectors on the bioprocessing cartridges. In some embodiments, the control fluid manifold may be urged onto or connected to the control fluid connectors on a bioprocessing cartridge using a pressurizable, inflatable, flexible container, such as a sack or a bladder which, upon inflation, causes the supply connectors to move towards and to be connected, such as sealably connected, to the control fluid connectors on the bioprocessing cartridge. In some embodiments, mechanical mechanisms such as spring loaded mechanisms or automatic or manual locking mechanisms may be used to connect the control fluid manifold to the control fluid connectors.

In some embodiments, the control fluid manifold is used to supply a control fluid, such as air pressure, vacuum, or a pressurized liquid to various control channels on a bioprocessing cartridge via the control fluid connectors in conjunction with the individual supply connectors. In some embodiments, the control fluid is used to provide pressure and/or vacuum on a non-contact side of a pump or valve membrane (i.e. a side of the membrane that does not come into contact with the process fluids) on a bioprocessing cartridge to actuate the pump or valve. This actuation may serve to open or close the valves and/or to cause the pumps to pump fluids through the process fluid channels on a bioprocessing cartridge. By using specific defined protocols included in an automated control system, the pumps and valves may be controlled by supplying pressure and/or vacuum to the pumps and valves to control the actuation of the various valves or pumps in specific orders or according to specific instructions to perform one or more bioprocesses on a bioprocessing cartridge.

Though throughout the remainder of this application, the control fluids supplied may be specifically referred to as air pressure and vacuum, it should be understood that other control fluids may be used to perform the individual control steps, including both other gaseous control fluids, such as nitrogen or oxygen or enriched air and the like, and other liquid control fluids. In addition, in some embodiments, one or more of the control fluids may be treated prior to entering the bioprocessing cartridge and/or the control fluid manifold. Such treatment may include, purification, such as via filtration, enrichment, pressure regulation, de-humidification, humidification and the like to assist with efficient processing.

Each of the individual supply connectors may be in fluid communication with a pressure source and/or a vacuum source. The pressure source and/or vacuum source may comprise an external pressure or vacuum source such as a "house" air pressure supply and/or a "house" vacuum supply. In some embodiments, the device includes a vacuum pump and/or a compressor and one or both of the vacuum and the air pressure may be supplied to the bioprocessing cartridges without use of external supplies. The device may also include appropriate pressure gauges and regulators to help control the amount of pressure supplied to each of the supply connectors and thus to the control channels and the valves and pumps and in some embodiments, the device includes reservoirs for storing pressure and vacuum to be supplied to the cartridge and to limit or avoid pressure or vacuum shortages or delays caused by delay in the supply of pressure or vacuum, such as a delay caused by the response time of the compressor and/or vacuum pump.

Alternatively, instead of a control fluid manifold, in some embodiments, some or all of the control fluid connectors on a bioprocessing cartridge may be connected individually to a vacuum and pressure source.

In some embodiments, the slots on the bioprocessing device may be reconfigurable, removable and/or replaceable to provide for different configurations, sizes or types of bioprocessing cartridges. The slots may include various guides, holes, holders, or any combination thereof, to ensure that the bioprocessing cartridges may be retained in the slots at a correct height and orientation to perform the desired bioprocess. In some embodiments, the cartridges may be vertically oriented, such that the process fluids are drawn in a generally upwards direction into the cartridges and leave the cartridges in a generally downwards direction. This vertical orientation may serve to preserve space and may help with efficient fluid removal from one or more of the bioprocessing chambers. In some embodiments, the cartridges may have one or more process fluid supplies that do not enter and/or leave the bioprocessing cartridges in a generally vertical orientation. In some embodiments, the cartridges may be horizontally oriented, such that fluid can be pumped into and out of the cartridge in a horizontal direction. The fluids may be contained such that loss of fluid or spillage would be prevented, for example, by containing the fluid in a closed volume containers which may be capable of deforming to eject fluid from the container or accept fluid coming into the container. The fluid may be pumped into the bioprocessing chambers of the cartridge and then aspirated out of the bioprocessing chambers of the cartridge using suction or vacuum pressure. The fluids may be located in the same horizontal plane or in a horizontal plane parallel to the cartridge or cartridges plane. In some embodiments, the fluid and fluid containers may be oriented in a vertical orientation with respect to the cartridge or cartridges wherein the cartridge or cartridges are in fluid communication with the fluid containers through tubing connecting the vertical fluid containers with the horizontal cartridge or cartridges.

In some embodiments, the device may comprises a removable fluid container tray comprising one set or multiple sets of fluid container holders able to hold fluid containers for use during bioprocessing. The number of sets of fluid container holders may be any suitable number according to the protocol for which the containers are being used. In some embodiments, the number of sets of fluid container holders may be equal to or less than the number of slots within the device. In some embodiments, the number of sets of fluid container holders may be more than the number of slots within the device. In some embodiments, such as embodiments when fewer bioprocessing cartridges than the number of slots in the machine are being used, blank fluid container holders may be provided beneath the empty slots.

The fluid container holders may be configured to receive waste, reagent and/or sample containers in appropriate size and number according to the bioprocess to be performed. For example, in some embodiments, the fluid container holders are provided to receive a set of fluid containers, where the set includes at least one sample container, at least one reagent container, and/or at least one waste container. In some embodiments, the fluid container holders may be configured to receive differently sized containers each according to their function. For example, in some embodiments, the sample container is sized differently from one or more of the reagent containers, the waste container may also be sized differently from either or both the reagent containers and the sample containers, and the reagent containers may each be the same size. In this way, it should be understood that a set of fluid container holders may comprise multiple differently sized holders for differently sized containers. In some embodiments, sets of the fluid container holders are individually pre-packaged with either empty or pre-filled reagent containers and available waste containers and the sets of the fluid container holders may be placed in the removable fluid container tray with the sample container added to the appropriate available fluid container holder by the operator according to a predetermined protocol. In some embodiments, multiple sets of fluid container holders are pre-packaged with either empty or pre-filled reagent containers and available waste containers together to fit an entire removable fluid container tray or may be supplied with a removable fluid container tray. In some embodiments, the fluid container holders are configured to share one or more containers. For example, the fluid container holders may be configured to share a waste container or a reagent container. In some embodiments, the fluid container holders and/or the removable fluid container tray are multi-use or single use.

In some embodiments, the bioprocessing device also includes an automated control system, which includes a computer control system configured to control at least one parameter associated with a bioprocessing procedure or protocol. In some embodiments, the computer control system may be configured to control one or more of the following non-limiting examples of parameters: the actuation of one or more access valves on a bioprocessing cartridge; the actuation of one or more pumps on a bioprocessing cartridge; the amount of one or more process fluids supplied to one or more bioprocessing cartridges; mixing of one or more process fluids; exposure time of one or more solid supports to one or more process fluids, pumping and flow paths of one or more process fluids, circulation of one or more process fluids; pumping flow rates, sequence, pumping delays, and volume of process fluid addition and/or purging from one or more bioprocessing cartridges and pressure and/or vacuum supplied to the one or more bioprocessing cartridges, such as to one or more control fluid channels on a bioprocessing cartridge.

In some embodiments, the automated control system includes one or more of the following: a computer control system comprising a central processing unit, a graphical user interface ("GUI"), and an operator input system. The central processing unit may include memory and one or more microcontrollers. In operation, a user may use the operator input system in conjunction with the GUI and software or firmware loaded on the computer control system to select either one or more stored protocols or to enter one or more user generated protocols which instruct the one or more microcontrollers to initiate a series of valve and pump actuations on one or more bioprocessing cartridges in one or more slots of the device. The valve and pump actuations may be controlled using the pressure and vacuum supplies. These valve and pump actuations may serve to pump process fluids, including reagents and samples from containers in the fluid container holders into the process fluid channels and bioprocessing chambers of the bioprocessing cartridges and from the bioprocessing cartridges into one or more fluid containers and to process the samples according to the selected protocol. In some embodiments, the automated control system is able to perform the same or different protocols on multiple bioprocessing cartridges in the device using the same types or different types of sets of fluid container holders, containers, reagents and samples for each protocol. During processing, the GUI may provide for the user to observe the progress of the one or more protocols being performed on the bioprocessing cartridges and the computer control system may provide for alarms to indicate completion of the processing or errors or other problems that may occur during processing. In some embodiments, the bioprocessing device and/or the computer control system may also include safety interlocks that prevent the device from running a protocol if the device is in one or more unsafe or unprepared states, such as, by way of non-limiting example, the container tray is not fully inserted into the device, one or more bioprocessing cartridges are not properly inserted into the slots or are not properly connected to the air and/or vacuum supply, the air or vacuum supply is inadequate, the air or vacuum supply exceeds safety limits and/or the electrical supply is inadequate or exceeds safe limits.

The operator input system may comprise any appropriate input system, such as a keyboard, keypad, mouse, touchscreen or any other suitable device used by users to interact with computer systems and to run software or firmware. The software or firmware used in the bioprocessing device may be application specific or may be commercial off the shelf software. In some embodiments, the bioprocessing device may include sensors for monitoring the progress of one or more protocols running on the device. For example, the device may include pressure and vacuum sensors for measuring the pressure and vacuum supplied during various steps of the protocol, flow rate sensors, temperature sensors, time lapse sensors, sensors for measuring any parameters associated with one or more steps of processes performed on the device. The sensors may provide passive measurement of various parameters that may be recorded in the control system or may provide active measurement that may be used for control of the progress and conduct of the process. Such control may occur using any suitable control procedure, including, but not limited to proportional, integral, proportional-integral or proportional-integral-derivative control.

In some embodiments, the computer control system further includes devices and/or mechanisms for remote control of the device and/or for uploading information into the computer control system such as software or firmware updates and for downloading and/or storing information associated with one or more runs performed on the device. For example, the device may provide for upload of information onto the device or download of the process parameters used for any run directly onto a computer via a direct connection, such as an ethernet port, a Personal Computer Memory Card International Association (PCMCIA) slot or an universal serial bus (USB) port, via a wireless connection, via a portable storage medium such as a flash drive or thumb drive, a writable CD-ROM, or DVD or the device may be connected to a network, such as a LAN or WAN or to an internet-based application. In addition, the device may provide for secure recordation of the process parameters, preventing or ensuring no modification of the actual run parameters after a run has been conducted and may provide for date/time validation of the runs. In some embodiments, the software or firmware is configured to interface with an electronic notebook program, such as a secure electronic notebook program to download the process parameters and run data directly into the program.

In some embodiments, the device is sized to allow for use on a typical lab bench-top or within a chemical hood and may be used at a variety of temperatures such as at room temperature or in a cold room.

In use, the automated control system verifies that the bioprocessing cartridges are properly inserted into the device, and then may accept the user selected protocol (either preloaded or user generated). The bioprocessing device may be pre-programmed with a protocol such as a western protocol or a nucleic acid purification protocol or a southern protocol. In some embodiments, the bioprocessing device may be capable of storing additional protocols. The device may allow the user to select from a list of existing protocols or create and save a user defined protocol, for example, a user defined western or nucleic acid purification protocol. In some embodiments, the device may further allow for more consistent and reproducible run-to-run experimentation. The device may also be programmed with a protocol without the need for re-optimization between runs. After the protocol is selected, the automated control system will actuate the valves and pumps according to the selected protocol to pump fluids from the fluid containers into the bioprocessing cartridges and bioprocessing chambers therein to perform the desired bioprocessing on the cartridge.

II. Bioprocessing Cartridge

In some embodiments, a bioprocessing cartridge may comprise mesofluidic or microfluidic circuits that have been formed from one or more substrate layers. In some embodiments, bioprocessing cartridge may include one or more additional layers or elements between the one or more the substrate layers. In some embodiments that include the one or more additional layers or elements, at least one of the additional layers or elements may include one or more membranes or a membrane layer that may be used in conjunction with the substrate and a pressure or vacuum source as at least one valve or pump.

In some embodiments, the bioprocessing cartridge may comprise at least one bioprocessing chamber configured to contain a solid support and a plurality of mesoscale and/or microscale fluid flow channels in direct or indirect fluid communication with the bioprocessing chamber through at least one pump, such as a pump that is integral or included in, within or on the cartridge or one or more layers from which the cartridge is constructed. In some embodiments, the fluid flow channels may comprise process fluid channels and/or control fluid channels. In some embodiments, the bioprocessing cartridge may comprise two or more fluid layers. In some embodiments, the bioprocessing cartridge may include at least a process fluid layer and a control fluid layer. In some embodiments, there may be communication between the process fluid layer and the control fluid layer either directly or indirectly. In some embodiments, the process fluid layer may comprise the layer with the majority of the process fluid channels thereon, while the control fluid layer may comprise the layer with the majority of the control fluid channels thereon.

As used herein, the term "microscale" refers to flow channels or other structural elements, having at least one cross-sectional dimension on the order of about 0.1 µm to less than about 1000 µm, such as about 0.1 µm to about 500 µm, about 10 µm to about 250 µm or about 100 µm to about 250 µm, and the term "mesoscale" refers to flow channels or other structural elements, having at least one cross-sectional dimension on the order of about 1000 µm to about 4 mm, such as about 1000 µm to about 3.5 mm, about 1000 µm to about 2.5 mm, about 1000 µm to about 1.5 mm, or greater than about 1000 µm, greater than about 1100 µm, greater than about 1250 µm or greater than about 1500 µm.

In some embodiments, the bioprocessing cartridge may comprise a plurality of mesoscale and/or microscale process fluid flow channels. In some embodiments, the process fluid flow channels may provide fluid connection between process fluid connectors on a bioprocessing cartridge and one or more pumps, access valves and/or process valves on the bioprocessing cartridge. In some embodiments, the process fluid flow channels may be used to supply process fluids, such as reagents and/or samples, through the various valves and pumps on a bioprocessing cartridge and into any of one or more bioprocessing chambers on a bioprocessing cartridge. In general, the process fluid channels may direct any of the process fluids, such as reagents and/or samples used in the actual processes performed on the bioprocessing cartridge, to the appropriate places at the appropriate times. In some embodiments, one or more of the process fluid flow channels may be provided on a different fluidic layer than the control fluid flow channels.

In some embodiments, the bioprocessing cartridge may comprise a plurality of mesoscale and/or microscale control fluid flow channels. In some embodiments, the control fluid flow channels are microscale. In some embodiments, the control fluid flow channels are mesoscale. In some embodiments, the control fluid flow channels may provide fluid communication between control fluid connectors on a bioprocessing cartridge and one or more pumps, access valve and/or process valves on the bioprocessing cartridge. In some embodiments, the control fluid flow channels may be used to individually supply pressure or vacuum to the membranes of pumps and valves on the bioprocessing cartridge to actuate the pumps or open or close the valves. In some embodiments, the control fluid flow channels may be on a different fluid layer of the bioprocessing cartridge than the process fluid channels.

In some embodiments, the bioprocessing cartridge may be a disposable cartridge. A disposable cartridge may reduce the danger of cross-contamination between runs. The cartridge may be configured so that a consistent amount of solution or reagents may be delivered to the cartridge to increase reproducibility.

In some embodiments, the control fluid connectors may be configured to connect the plurality of control fluid flow channels to an automated control system. In some embodiments, each of the control fluid flow channels may be in fluid communication with an independent control fluid connector. In some embodiments, the control fluid connectors may be configured to be in communication with the automated control system via a control fluid manifold. In some embodiments, the bioprocessing cartridges may be configured to be held in a cartridge holder of a bioprocessing device that urges the control fluid connectors into fluid communication with supply connectors on the bioprocessing device that are in fluid communication with a control fluid manifold. In some embodiments, the urging is accomplished using an expanding bladder or sack, a mechanical or manual latching mechanism or an electronic latching or connecting mechanism, or any other suitable mechanism for urging the control fluid connectors into fluid communication with the supply connectors.

In some embodiments, the bioprocessing cartridge may comprise one or multiple bioprocessing chambers, including, but not limited to, one bioprocessing chamber, two bioprocessing chambers, two or more bioprocessing chambers, three bioprocessing chambers, three or more bioprocessing chambers, four bioprocessing chambers, four or more bioprocessing chambers, five bioprocessing chambers or five or more bioprocessing chambers, or any suitable number of bioprocessing chambers. The bioprocessing chambers may be closed or sealed such as by any suitable sealing means including use of gaskets, o-rings, welds, clamps, and the like or, in some embodiments, one or more bioprocessing chambers may be accessible by an operator or user. In some embodiments, the bioprocessing chambers may have inlets and outlets on different fluidic layers of the bioprocessing cartridge, while in other embodiments, the bioprocessing chambers may have inlets and outlets on the same fluidic layers. In some embodiments, the volume of the processing chamber should be suitable to allow for fluid to freely flow across a solid support therein or across the surface of a solid support therein. In some embodiments, the bioprocessing chambers may have a fluid volume with or without the solid support present of between about 1 µl and about 100 ml, such as between about 10 µl and about 100 ml, between about 20 µl and about 100 ml, between about 50 µl and about 100 ml, between about 100 µl and about 100 ml, between about 150 µl and about 100 ml, between about 200 µl and about 100 ml, between about 250 µl and about 100 ml, between about 300 µl and about 100 ml, between about 500 µl and about 100 ml, between about 750 µl and about 100 ml, between about 1 ml and about 100 ml, between about 2 ml and about 75 ml, between about 3 ml and about 60 ml, between about 4 ml and about 50 ml, between about 4 ml and about 45 ml, between about 4 ml and about 40 ml, between about 4 ml and about 35 ml, between about 5 ml and about 30 ml, between about 10 ml and about 25 ml or between about 15 ml and about 20 ml.

The bioprocessing chambers may comprise fluid mixing chambers and/or may contain a solid support for processing one or more samples. The solid support can be any support for filtering, washing, staining, eluting, collecting, processing or conducting chemical reactions or bioprocessing. In some embodiments, the solid support may be selected from one or more of the following: filter cassettes, filter paper, precipitation membranes, precipitation filters, solid phase extraction columns, solid phase extraction cassettes, solid phase extraction disks, resins, membranes, such as blotting membranes, filter membranes, PVDF membranes, nylon membranes, positively charged nylon membranes and nitrocellulose membranes, reaction beads, such as glass beads and magnetic beads, rigid planar solid supports that contain arrays of biomolecules such as nucleic acid microarrays, protein arrays, and tissue arrays, microscopic slides and combinations thereof.

In some embodiments, the solid support in one or more bioprocessing chambers may comprise a filter paper, a filter or a filter cassette. The filter paper, filter or filter cassette may comprise any suitable type of filter having an appropriate chemistry, pore size, shape and three dimensional configuration, such as a symmetrical or asymmetrical three dimensional configurations including "V" or funnel-shaped pore configurations, and surface area for the intended use and maybe constructed for flow through, cross flow, tangential flow or any combination thereof. The filter paper, filter or cassette may comprise any suitable material, such as poylethersulfone, polyethylene, ultra-high molecular weight polyethylene, polypropylene, nylon, cellulose, cellulose-triacetate, polyacrylonitrile, polyamides, glass fiber, silica, polysulfone, PVDF, and the like. In some embodiments, the solid support in one or more processing chambers may comprise a precipitation membrane or a precipitation filter. In some embodiments, the solid support in one or more processing chambers may comprise a solid phase extraction column, a solid phase extraction cassette or a solid phase extraction disk. In some embodiments, the solid support in one or more processing chambers may comprise a blotting membrane. The filter, filter paper, or filter cassette may be a single layer or multiple layer filter. In some embodiments, the solid support in one or more bioprocessing chambers may comprise a plurality of beads such as coated beads, coated glass beads, glass beads, magnetic beads or coated magnetic beads.

In some embodiments, the bioprocessing chambers are open and provide access to the user for insertion of a solid support. In some embodiments, the bioprocessing chambers are open and are configured to receive a blot membrane with or without a blot membrane holder. Blot membrane holders may be used to prevent the blot membrane from contacting or sticking to one of the faces of the bioprocessing chamber and may be used to facilitate flow of the various process fluids around and across the surfaces of the blot membrane. In addition, in some embodiments, the bioprocessing chambers may include additional space to accommodate foaming during processing of a sample. For example, in some embodiments, where the bioprocessing chamber is open and a blot membrane is inserted by a user with or without a blot membrane holder, the bioprocessing chamber may be sized to provide additional space at the top of the chamber to prevent overflow of foam that may be formed during the bioprocessing. In addition, the bioprocessing chamber may be configured at the top such that the chamber is wider at the top than at the bottom. This increased width at the top provides additional volume to accommodate foam formation, if present.

In some embodiments, the bioprocessing cartridge may include one or more flow control elements. In some embodiments, the one or more flow control elements may be selected from pumps, process valves, check valves, access valves, layer pass-throughs and/or pass-through valves. In some embodiments, one or more of the flow control elements may be placed within a flow path defined by one or more of the plurality of fluid flow channels on the bioprocessing cartridges.

In some embodiments, the bioprocessing cartridge may comprise from about 1 to about 10 pumps, such as from about 1 to about 8 pumps, from about 1 to about 6 pumps, from about 1 to about 5 pumps or from about 1 to about 4 pumps. The pumps may be included in, within, or on, or may be integral to the bioprocessing cartridges or at least one layer of the bioprocessing cartridges. The pumps may be used to pump process fluids from process fluid containers into or out of the cartridges and through the plurality of process fluid channels on the cartridges. In some embodiments, a pump may be actuated by providing pressure and/or vacuum to the membrane of the pump using a control fluid channel associated with the pump on a different fluidic layer than the process fluid channels associated with the pump. In this manner the pumps may comprise membrane pumps similar to diaphragm pumps. In some embodiments, the pumps, when actuated may cause the fluid flow in the process channels to be turbulent, while in other embodiments, the fluid flow in the channels may be laminar or transitional.

In some embodiments, the bioprocessing cartridge may comprise from about 1 to about 20 access valves, such as from about 2 to about 18 from about 3 to about 16, from about 4 to about 14, from about 5 to about 13, from about 6 to about 12 or from about 7 to about 10 access valves. In some embodiments, the access valves control access of process fluids to and from the bioprocessing cartridges and generally are in direct fluid communication with one or more process fluid connectors on the bioprocessing cartridge. In some embodiments, the access valves may be actuated to open or close by providing pressure or vacuum to the membrane of the access valve using a control fluid channel associated with the access valve on a different fluidic layer than the process fluid channels associated with the valve, thereby opening or closing fluid communication between at least one process fluid channel on the bioprocessing cartridge and the process fluid connectors on the bioprocessing cartridge. When closed, the access valves may prevent process fluid from flowing into or out of the bioprocessing cartridge. In some embodiments, the bioprocessing cartridge may comprise an access valve within each of the flow paths between the process fluid connectors and each of the plurality of fluid flow channels. In some embodiments, at least two of the plurality of process fluid connectors share an access valve.

In some embodiments, the bioprocessing cartridge may comprise from about 1 to about 25 process valves, such as from about 1 to about 22, from about 1 to about 20, from about 1 to about 18, from about 2 to about 16, from about 2 to about 14, from about 3 to about 12, from about 3 to about 10 or from about 3 to about 8 process valves. The process valves may be either actuated to open or actuated to close depending on the individual process. In some embodiments, a process valve may be actuated by providing pressure or vacuum being supplied to the process valve membrane via a control fluid channel on a different fluidic layer than the process fluid channels associated with the process valve. The process valves may be used to route fluids to the appropriate places on the bioprocessing cartridges according to the protocols at the appropriate times after the fluids have accessed the bioprocessing cartridges through one or more access valves. In some embodiments, the bioprocessing cartridges comprise at least one process valve in a flow path between a pump and a bioprocessing chamber.

In some embodiments, the bioprocessing cartridge may include a check valve. In some embodiments, the bioprocessing cartridge may comprise at least one check valve. In some embodiments, the check valve or valves may allow for flow through the valve in one direction only, including flow between layers and may be actuated to open for flow in that direction via pressure supplied to the valve membrane via a control fluid channel or via pressure associated with process fluid flowing in the flow channel in the correct direction. In some embodiments, check valves may be provided to supply a control fluid between two different layers of a bioprocessing cartridge. In some embodiments, the control fluid may be supplied to serve as a process fluid, such as to provide air pressure for drying a filter or membrane or to expel residual fluids in a pump, channel or bioprocessing chamber. In some embodiments, the check valves may allow for fluid to flow across them in one direction and fluid to flow in one direction through them between layers. In some embodiments, check valves are provided that allow for flow in either direction across them, but that allow for flow through them in only one direction, such as in one direction either from the process fluid layer to the control fluid layer or from the control fluid layer to the process fluid layer on a bioprocessing cartridge. In some embodiments, the bioprocessing cartridges comprise at least one check valve that is a process valve or an access valve.

In some embodiments, the bioprocessing cartridge may include at least one layer-pass through or pass-through valve. The layer pass-throughs or pass-through valves may provide for flow of a process fluid between different fluidic layers on a bioprocessing cartridge. For example, where the inlet to a bioprocessing chamber is on a different fluidic layer than a given flow channel associated with fluid intended for the chamber, the flow channel may direct the fluid to a layer pass-through or a pass-through valve where the fluid is transferred from one fluidic layer to the fluidic layer associated with the inlet to the processing chamber and may then proceed into the processing chamber via process fluid channels on the other fluidic layer. Layer pass-throughs generally are passive fluidic connections between fluidic layers, while pass-through valves may control the flow of the fluid from one layer to another by requiring actuation to either open or close either by the pressure in the fluid channel itself or by actuation using a control fluid.

In some embodiments, the bioprocessing cartridge includes one or more process fluid connectors. In some embodiments, the process fluid connector may include tubes or tube-like structures that are configured to fluidly connect the cartridge to one or more outside (i.e. not on the bioprocessing cartridge) fluid containers. Fluids may be introduced into the cartridge or removed from the cartridge and from or into the one or more fluid containers through the process fluid connectors, and then transported through the fluid flow channels into the various portions of the bioprocessing cartridge. In some embodiments, the bioprocessing cartridge or cartridges may include between about 3 to about 20 process fluid connectors, such as about 4 to about 18, about 5 to about 16, about 6 to about 14, or about 8 to about 12 process fluid connectors, or about 3 or more process fluid connectors, about 4 or more process fluid connectors, about 5 or more process fluid connectors, or about 6 or more process fluid connectors. In some embodiments, the process fluid connectors are connected to a process fluid manifold on a bioprocessing device through which the various process fluids may be supplied to and removed from the bioprocessing cartridge via one or more of the plurality of flow channels. In some embodiments, each of the process fluid connectors receives fluid from an independent fluid container, where each container may contain the same or different fluids as in another container.

In some embodiments, the process fluid connectors may be in fluid communication with the process fluid reservoirs via aspiration/expiration tubes, which may be in fluid communication with the process fluid connectors or the process fluid connectors may be aspiration/expiration tubes. When placed in a slot of a bioprocessing device, the aspiration/expiration tubes may extend away from the cartridge and into the fluid reservoirs. In one embodiment, the aspiration/expiration tubes may extend into reservoirs positioned below the cartridge slot when the cartridge is inserted into the cartridge slot. The reservoirs may be any tube, bottle, vial or similar reservoir able to hold a fluid. In some embodiments, the reservoirs may include a sealing layer that may permit the tips of the aspiration/expiration tubes to pass into the reservoirs but which may also reduce the risk of an external substance from entering the reservoirs, or which may reduces the loss of reagents or fluids from the reservoirs. The aspiration/expiration tubes may have the same or different lengths with respect to each other, depending on the size and/or shape of the reservoir or reservoirs. While the aspiration/expiration tubes may be used to transport process fluid from a reservoir into the cartridge, the aspiration/expiration tubes may also be used to expel fluids as waste from the cartridge into one or more of the reservoirs.

In addition, in some embodiments, the containers in conjunction with the aspiration/expiration tubes and the bioprocessing cartridge or cartridges may be used to receive one or more containers or mixing containers for process fluids during bioprocessing. For example, in some embodiments, fluid may be removed from one process fluid container into the bioprocessing cartridge and then out of the bioprocessing cartridge and into a different container. In this manner the fluid may be pumped back and forth between the containers using the bioprocessing cartridge to provide mixing of the fluids. Alternatively, in some embodiments, fluids may be removed from and returned back to the same container to provide mixing of the fluid without combining it with any other fluids. Furthermore, in some embodiments, one or more of the containers and the container holder or holders, the container tray and the bioprocessing device may be configured to provide stirring of a fluid in the container, such as, for example, a magnetic stirring rod, or any other suitable stirring mechanism for stirring or agitating a fluid in the container.

In some embodiments, the bioprocessing cartridge may include one or more pre-loaded or on-board process fluids or process reagents. In such embodiments, the process fluids or process reagents may be included in separate reservoirs or chambers on the cartridge or may be included in one or more pumps or channels on the cartridge. In some embodiments, the pre-loaded or on-board process fluids or process reagents may comprise a process fluid or a component of a process fluid. In some embodiments, the pre-loaded or on-board process fluids or process reagents may comprise a process reagent that is dissolved into a process fluid after exposure to the process fluid.

In some embodiments, the bioprocessing cartridge may be designed for multiple uses. In some embodiments, the cartridge may be disposable and/or designed for a specific or limited number of uses, such as about 20 uses or less, about 15 uses or less, about 10 uses or less, about 9 uses or less, about 7 uses or less, about 5 uses or less, or about 3 uses or less. In some embodiments, protocols may be provided on the automated control system to provide for cleaning of the multiple use cartridge prior to re-use. Accordingly in some embodiments, the cartridge may be a consumable product.

In some embodiments, the bioprocessing cartridges may be single use cartridges. In some embodiments, the cartridge may include an indicator configured to signal when a cartridge has and/or has not been used. In some embodiments, the indicator may be any suitable indicator for indicating when a cartridge has and/or has not been used. In some embodiments, the indicator may be a color indicator located on the card at a suitable location, such as in a color indicator chamber, which color indicator may permanently change color during bioprocessing to indicate that the cartridge has been used. In some embodiments, the automated control system of a bioprocessing device may be configured to detect the color change and prevent operation when a used card is placed in a slot. In some embodiments, the automated control system of a bioprocessing device may be configured to detect both the indicator color prior to the color change and after the color change and may prevent or stop operation when one or both of the colors are not observed at different times.

In some embodiments, the indicator may include, a bibulous matrix, such as a white bibulous matrix such as a paper tape that is impregnated on one side with a red dye while the other side is white such that when that matrix is wetted, the dye diffuses throughout the matrix, turning the side that was white to a red color. In some embodiments, the white side is initially displayed to the device's detector. The detector may then view the change in the indicator from white to red when a cartridge has been used. In some embodiments, the color change may be produced by directing some of the liquid used in the bioprocessing device to a separate chamber containing a piece of color indicator tape. The tape may remain wetted by including a check valve that permits fluid flow into the tape chamber but prevents the fluid from returning to the process fluid channel after it has interacted with the dye. In addition, once the indicator material has been wetted and the dye redistributed throughout the matrix, thereby turning the white side red, the color remains in the matrix even after the matrix dries out. An example of a suitable color indicator tape is described in U.S. Pat. No. 7,105,225 the entire contents of which are hereby incorporated by reference. In addition, suitable indicator tapes may include water contact indicator tapes such as 3M® Water Contact Indicator Tapes 5557, 5558, or 5559.

In some embodiments, the water sensitive paper or tape may comprise a small round piece of paper or tape (approx 5-15 mm, such as 8 mm in diameter) positioned between two layers of a bioprocessing cartridge and within a chamber that allows it to be clearly viewed by the customer when the card is out of the instrument and by an electronic color sensor while the cartridge is inserted within the instrument. When the cartridge is used during a run, a small portion of the first liquid to enter the cartridge enters the chamber containing the paper or tape, causing the color change. This change may occur after less than about 20 seconds of run time. An electronic color sensor, such as a color sensor with integrated LED illumination may be imbedded in the bioprocessing device, such as in the cartridge slot. When running a protocol, after the "Run" button is pushed by the user, the color sensor detects the color of the paper or tape and may send an input to the GUI that will direct the user to insert a new card if the incorrect color is detected. In some embodiments, the system may also allow for a second color detection during a run. In some embodiments, the second color detection can occur as follows: the GUI interrogates the sensor again after a set length of run time has occurred, such as between about 1 minute and about 10 minutes, such as about 2 minutes or more, about 3 minutes or more, about 4 minutes or more or about 5 minutes or more, to determine if the paper or tape has changed color. If the paper or tape has not, an error message is displayed and the protocol is stopped.

In some embodiments, the color sensor may determine a color change as follows. At calibration, each sensor may output a signal in response to a standard red card and a standard white card. The midpoint between those signals (in kHz) is determined to be the dividing point between what is considered red (used) and what is considered white (unused). This information may be permanently saved within the instrument memory. In operation by a user, this information is used for the first color detection as described above. For the second test, another check is made after the set time period, such as after 2 minutes into the run and the returned value compared to the first. If there is a change of 1 kHz or more, the card is determined to have not been tampered with and the run continues. If this change is not detected, the run can be stopped and the user instructed to insert a new cartridge or cartridges.

In some embodiments, the color sensor may determine a color change as follows. During the calibration period a series of measurements are taken at set time intervals to establish a baseline color level. After the calibration period, measurements of the color are taken at set time points. Each measurement is compared to the baseline level. Once a color level is detected that is more than about 2 standard deviations, more than about 3 standard deviations, more than about 4 standard deviations, or more than about 5 standard deviations from the base line color level, a color change is deemed to have occurred and the card is deemed to have not been tampered with and the run continues. If a color change as determined by an appropriate number of standard deviations has not occurred, the run can be stopped and the user instructed to insert a new cartridge or cartridges.

In some embodiments, the bioprocessing cartridge may include one or more pumps, valves, process fluid channels and/or control fluid channels that are integral to the cartridge, such as included on one or more layers of the cartridge. In some embodiments, the process fluid channels and/or the control fluid channels are rigid flow channels or have one or more rigid walls. The channels may be any suitable cross-sectional shape, including circular, elliptical, square, rectangular, D-shaped and any other suitable polygonal cross-section. In some embodiments, one or more of the channels may have a D-shaped cross-section or a square or rectangular shaped cross-section, where the substantially-semicircular portion of the channel (for D-shaped cross-section) or three sides of the channel (for the square or rectangular cross-section) has rigid walls and where the flat portion of the channel (D-Shape) or the fourth side of the channel is formed from a film that may be the same or a different material from the rigid walls and that may be flexible or less rigid than the material used for the rigid walls or more rigid than the material used for the rigid walls. In some embodiments, the flexible or less rigid material is flexible or less rigid as a result of its thinness, rather than as a result of the inherent material properties of the flexible or less rigid material. For example, in some embodiments, one or more of the process fluid channels or control fluid channels may have a D-shaped or square or rectangular cross-section, where the flat side (D-shaped) or one of the sides (square or rectangular-shaped cross-section) of one or more of the channels comprises a metal or plastic film or foil and the other side or sides of the one or more channels comprise plastic. In some embodiments the process fluid channels and/or the control fluid channels are not flexible tubing.

In some embodiments, the bioprocessing cartridges may be regularly shaped, such as rectangular, square or generally rectangular or generally square, while in other embodiments, the bioprocessing cartridges may have more complex polygonal shapes or be generally polygonal in shape or be irregularly shaped. In some embodiments, the cartridges may have at least one dimension that is longer than about 5 cm, such as at least one dimension that is between about 6 cm and about 40 cm, such as between about 7 cm and about 37 cm, between about 8 cm and about 35 cm, between about 9 cm and about 30 cm, between about 10 cm and about 25 cm, between about 11 cm and about 22 cm, between about 12 cm and about 21.5 cm, between about 12 cm and about 20 cm, between about 12 cm and about 18.5 cm, between about 14 cm and about 18.5 cm, excluding any addition to the dimensions of the bioprocessing cartridges as a result of protrusions, including but not limited to protrusions such as process fluid connectors, control fluid connectors and aspiration/expiration tubes. In some embodiments, the bioprocessing cartridges may be generally flat, having at least one dimension ("depth") that is substantially shorter than one or both of the other dimensions. In some embodiments, the bioprocessing cartridges have a depth that is less than about 50% of the longest dimension as measured above, such as less than about 40% of the longest dimension, less than about 30% of the longest dimension, less than about 25% of the longest dimension, less than about 20% of the longest dimension, less than about 15% of the longest dimension, less than about 10% of the longest dimension or less than about 7.5% of the longest dimension.

In some embodiments, the bioprocessing cartridges may include one or more cartridge alignment guides to ensure the cartridge is inserted in the proper orientation into the cartridge slot. In some embodiments, the cartridge alignment guide may be a tab or tabs or a projection or projections, or groove or grooves that fit within a corresponding opening in the cartridge slot as the cartridge is inserted into the cartridge slot.

III. Methods of Bioprocessing

In some embodiments, methods of bioprocessing include: providing a bioprocessing cartridge, where the cartridge comprises at least one bioprocessing chamber containing a solid support and a plurality of mesoscale and/or microscale fluid flow channels in fluid communication with the bioprocessing chamber; and pumping at least one process fluid through at least one of the plurality of channels into the at least one bioprocessing chamber. In some embodiments, the pumping includes pumping one or more process fluids and/or a sample into said processing chamber and into contact with the solid support. The process fluids delivered to the solid support in the cartridge may be any suitable solvent, solution or reagent for use in the desired bioprocess, including but not limited to liquid reagents used for chemical reactions, solvents or solutions used for washing, antibody solutions, buffer solutions, blocking buffer solutions and solutions containing fluorescent labeling reagents. The process fluids also may include samples that are to be processed such as proteins, nucleic acids and other macromolecules, cells, cell lysates, and combinations thereof. In some embodiments, the at least one processing fluid includes at least one blocking buffer. In some embodiments, the at least one processing fluid includes at least one antibody. In some embodiments, the at least one processing fluid includes at least one washing fluid. In some embodiments, the method of bioprocessing may include pretreating the cells prior to pumping. In some embodiments, pretreating the cells may include adding a salt to the cells, such as for example, NaCl, MgCl$_2$, CaCl$_2$, NH$_4$Cl and the like. The cells may be pretreated using any suitable method for pretreating cells to increase plasmid yield. In some embodiments, the salt solution concentration may be any suitable concentration for improving yield, for example, a concentration of between about 0.1M and about 0.5M, between about 0.2M and about 0.5M. In some embodiments, the salt concentration may be any suitable concentration for increasing the plasmid yield by at least 20%, by at least 30%, by at least 40%, by at least 50%, by at least 55%, by at least 65%.

In some embodiments, the pumping at least one process fluid through at least one of the plurality of channels into the at least one bioprocessing chamber includes pumping the at least one process fluid through a flow channel accessing the bottom portion of the chamber. In some embodiments, the pumping at least one process fluid through at least one of the plurality of channels into the at least one bioprocessing chamber includes pumping the at least one process fluid through a flow channel accessing the top portion of the chamber. In some embodiments, the pumping at least one process fluid through at least one of the plurality of channels into the at least one bioprocessing chamber includes pumping the at least one process fluid through a flow channel accessing a side portion of the chamber.

In some embodiments, pumping at least one process fluid through at least one of the plurality of channels into the at least one bioprocessing chamber includes circulating at least one process fluid from the bioprocessing chamber through a fluid flow channel accessing the bottom portion of the chamber, and back into the chamber through a fluid flow channel accessing an upper portion of the chamber.

In some embodiments, pumping at least one process fluid through at least one of the plurality of channels into the at least one bioprocessing chamber includes circulating at least one process fluid from the bioprocessing chamber through a fluid flow channel accessing the top portion of the chamber, and back into the chamber through a fluid flow channel accessing the bottom upper portion of the chamber.

In some embodiments, pumping at least one process fluid through at least one of the plurality of channels into the at least one bioprocessing chamber includes circulating at least one process fluid from the bioprocessing chamber through a fluid flow channel accessing the side portion of the chamber, and back into the chamber through a fluid flow channel accessing a bottom portion of the chamber.

In some embodiments, pumping at least one process fluid through at least one of the plurality of channels into the at least one bioprocessing chamber includes pumping at least one processing fluid through a filter or filter membrane in the at least one bioprocessing chamber. In some embodiments, the filter membrane comprises a blot membrane. In some embodiments, the filter membrane comprises a western blot membrane. In some embodiments, the filter comprises a cell separation or cell capture membrane. In some embodiments, the filter comprises a lysate clarification filter. In some embodiments, the filter comprises a nucleic acid precipitate filter. In some embodiments, the filter comprises a nucleic acid purification filter. In some embodiments, one or more of the filter membranes or one or more layers of the filter membranes have at least one pore size that is between about 0.2 μm and about 3 μm, between about 0.45 μm and about 2.5 μm, between about 0.5 μm and about 2.4 μm, between about 0.65 μm and about 2.2 μm, between about 0.8 μm and about 2.0 μm, between about 1.0 μm and about 1.5 μm, or between about 1.2 μm and about 1.5 μm. In some embodiments, the filter membrane comprises a cell separation or capture filter having two layers, one layer having a pore size between about 1.0 μm and about 1.5 μm, such as about 1.2 μm, and one layer having a pore size between about 0.5 μm and about 0.8 μm, such as about 0.65 μm. In some embodiments, the filter membrane may include a nucleic acid precipitation filter having two layers, one layer having a pore size between about 1.0 μm and about 1.5 μm, such as about 1.2, μm and one layer having a pore size between about 0.5 μm and about 0.8 μm, such as about 0.65 μm. In some embodiments, the filter membrane may include a cell separation or capture filter or a nucleic acid precipitation filter which may include an asymmetric filter having a pore size ranging from about 0.65 μm to about 2 μm. In some embodiments, the filter may include a glass fiber lysate clarification filter having a pore size between about 0.8 μm and about 1.5 μm, such as about 1.0 μm.

In some embodiments, pumping at least one process fluid through at least one of the plurality of channels into the at least one bioprocessing chamber includes adding a blocking buffer to the bioprocessing chamber, recirculating the blocking buffer across the surface of a blot membrane to form a blocked blot membrane, adding at least one antibody solution to the bioprocessing chamber; and recirculating the at least one antibody solution across the surface of said blocked blot membrane. In some embodiments, recirculating at least one antibody solution across the surface of the blocked blot membrane may include recirculating a primary antibody solution across the surface of said blocked blot membrane; washing the blot membrane; adding a secondary antibody solution to the bioprocessing chamber; and recirculating the secondary antibody solution across the surface of the washed blot membrane.

In some embodiments, the action of pumping may provide additional mixing within the bioprocessing chamber. For example, in some embodiments, where process fluid is circulated or recirculated through a fluid flow channel accessing the top or a side portion of the chamber, and back into the chamber through a fluid flow channel accessing a bottom portion of the chamber, the pressure associated with the pumping action into or back into the chamber may create localized eddy formation or the formation of areas of turbulence that promote flow of the process fluid across the bioprocessing chamber and mixing of the process fluid within the chamber. In some embodiments, when such a pumping method is used in the presence of a blot membrane with or without a blot membrane holder, the pumping action may serve to move the blot membrane within the bioprocessing chamber slightly with each pumping cycle, serving to ensure that the blot membrane is exposed on all sides to the process fluid in a substantially uniform manner and to prevent the blot membrane from sticking to a surface of the bioprocessing chamber or the blot membrane holder.

In some embodiments, pumping at least one process fluid through at least one of the plurality of channels into the at least one bioprocessing chamber includes pumping at least one processing fluid through at least one solid phase extraction column, at least one solid phase extraction membrane, at least one solid phase extraction cassette or at least one solid phase extraction disk in at least one bioprocessing chamber.

In some embodiments, the solid phase extraction column, solid phase extraction membrane, solid phase extraction cassette or solid phase extraction disk comprises a silica reversible binding ligand or a charge-switch binding ligand.

In some embodiments, pumping at least one process fluid through at least one of the plurality of channels into the at least one bioprocessing chamber includes pumping cell culture media or cells suspended in a solution across a cell separation filter to separate cells from the cell culture media, wherein the cells are captured on the filter. In some embodiments, the pumping may further include resuspending the captured cells in a lysing solution to form a lysate; neutralizing the lysate; and clarifying the lysate. The cells may be resuspended in the lysing solution and lysed in the chamber or the lysing solution or another solution may be used to resuspend the cells and pump them into a container, such as a reagent container containing lysing solution, where the cells may be lysed. In some embodiments, the lysate may be clarified by pumping the lysate through a filter membrane to remove unwanted cellular molecules and debris.

In some embodiments, pumping at least one processing fluid through at least one of the plurality of channels into the at least one bioprocessing chamber may further include extracting at least one biomolecule onto a solid phase extraction membrane or disk or cassette in a bioprocessing chamber; washing the solid phase binding material; and eluting the biomolecule from the solid phase. In some embodiments, pumping at least one processing fluid through at least one of the plurality of channels into the at least one bioprocessing chamber further includes precipitating and collecting the biomolecule in a bioprocessing chamber containing a precipitation filter In some embodiments, a method of bioprocessing may include: a) inserting at least one bioprocessing cartridge into a bioprocessing device, the bioprocessing cartridge comprising: i) at least one bioprocessing chamber containing a solid support therein; and ii) a plurality of mesoscale and/or microscale channels in fluid connection with the bioprocessing chamber; b) initiating a bioprocessing protocol on the bioprocessing device, the protocol comprising one or more of the following: i) controlling pumps and valves on the bioprocessing cartridge to supply reagents and/or samples from one or more containers to the at least one bioprocessing chamber of each of the at least one bioprocessing cartridges, ii) controlling pumps and valves on the bioprocessing cartridge to recirculate the reagents and or samples across the at least one bioprocessing chamber of each of the at least one bioprocessing cartridges; and/or iii) controlling pumps and valves on the bioprocessing cartridge to remove reagents and/or samples from the at least one bioprocessing chamber of each of the at least one bioprocessing cartridges.

In some embodiments, a method of applying one or more fluids to a solid support may include: a) inserting at least one bioprocessing cartridge into a bioprocessing device, the bioprocessing cartridge comprising: i) at least one bioprocessing chamber containing a solid support therein; and ii) a plurality of mesoscale and/or microscale channels in fluid connection with to said bioprocessing chamber; and b) performing a pumping sequence on the cartridge, wherein the pumping sequence includes entering one or more fluid addition cycles wherein fluid is pumped from the one or more containers within the bioprocessing device through one of the fluid flow channels and into the chamber.

In some embodiments, the pumping sequence may further include entering a purging cycle following each fluid addition cycle, the purge cycle including pumping fluid within the bioprocessing chamber into a designated waste container. In some embodiments, the pumping sequence may further include entering a circulating cycle after any of the fluid addition cycles, wherein the circulating cycle includes opening a valve in a fluid flow channel connected to the bottom of a bioprocessing chamber and pumping fluid from the bottom portion of the chamber through one or more fluid flow channels and into a top portion of the chamber. In some embodiments, the pumping sequence may be initiated and terminated using a programmable controller.

In some embodiments, a pumping sequence is performed including entering one or more fluid addition cycles wherein fluid is pumped from container in fluid communication with one of the process fluid connectors and into the chamber. The fluid in any of the containers or added during any of the fluid addition cycles can be the same or different than fluid in any of the other containers or added during any other of the fluid addition cycles. The pumping sequence may further include performing a purging cycle following any of the fluid addition cycles where fluid within the chamber is pumped out of the chamber into a waste container or a container designated to collect waste fluid. In some embodiments, fluid from multiple reservoirs may be added during the same fluid addition cycle, or a subsequent fluid addition cycle is performed without performing a purging cycle so that two or more fluids may be introduced to a chamber at the same time (although the total volume of the added fluids cannot exceed the available volume within the chamber). The pumping sequence may further include entering a circulating cycle after any of the fluid addition cycles where fluid in the chamber is pumped from the chamber through one or more process fluid channels of the cartridge and back into the chamber.

In some embodiments, the fluid addition cycles may be terminated after a predetermined amount of time elapses or after a predetermined volume of fluid is added. Similarly, the purging cycles and circulating cycles may be terminated after a predetermined time elapses. The amount of time elapsed and/or the amount of fluid added may vary depending on the selected protocol or type of bioprocessing. In some embodiments, the protocol may include at least one circulation or incubation cycle, where the solid support is exposed to one or more process fluids for a selected period of time either with the fluid circulating or for a hold period without fluid circulating.

In some embodiments, the pumping sequence may be designed for the immunolabeling, rinsing and incubation for a western blot analysis. In such embodiments, a blot membrane, such as by way of example a nitrocellulose or polyvinylidene flouride (PVDF) membrane, containing the separated proteins is placed in the cartridge chamber using a membrane holder that provides for flow of fluid across the chamber and membrane without allowing the membrane to stick to any of the walls of the chamber, and the cartridge is placed in the bioprocessing device. Antibody solutions may be added from the fluid containers in the bioprocessing device to the cartridges and the chamber containing the membrane along with the appropriate blocking and washing solutions. The pumping sequence, duration, and solutions used are selected depending on the specific analysis and proteins involved and can be modified by the user.

In some embodiments, the pumping sequence may be designed for the labeling of a molecule for a western blot analysis using a label or tag, such as a fluorescent tag, such as quantum dots or fluorescence dyes, such as Alexa Fluor® dyes. Solutions containing labels may be added from the fluid containers in the bioprocessing device to the cartridges. The pumping sequence, duration, and solutions used are selected depending on the specific analysis and proteins involved and can be modified by the user.

In another embodiment, the pumping sequence may be designed for transfection grade plasmid preparations. Bacterial cells in a solution or in cell culture media are placed in a sample container in the bioprocessing device containing an appropriate bioprocessing cartridge. The cells are captured on a filter by pumping them across a filter in a cartridge chamber using the device. The cells are resuspended and lysed using a lysing solution, such as one or more alkaline solutions, the lysate is clarified by pumping the lysate across another filter in a different cartridge chamber. The clarified lysate is passed through a solid phase extraction disk and then to a waste container. The solid phase extraction disk is washed at least once and then the bound biomolecules are eluted from the solid phase extraction disk. The eluted biomolecules are captured on a precipitate filter and washed at least once, at which point the precipitated biomolecules are dissolved in an appropriate buffer and pumped into a final product container in the bioprocessing device.

In another embodiment, the pumping sequence may be designed for food safety analysis. A sample may be placed in a sample container in the bioprocessing device containing an appropriate bioprocessing cartridge. Bacterial cells may be separated from larger debris and are captured on a filter by pumping them across a filter in a cartridge chamber using the device. The bacteria may be lysed using a lysing solution, the lysate may be clarified by pumping the lysate across another filter in a different cartridge chamber. The clarified lysate may be passed through a solid phase extraction disk and then to a waste container. The solid phase extraction disk may be washed at least once and then the bound DNA are eluted from the solid phase extraction disk and pumped into a final product container in the bioprocessing device.

In some embodiments, a method of applying one or more fluids to a solid support may further include independently opening and closing access valves connecting to process fluid connectors to selectively control the amount of fluid entering or leaving the fluid flow channels. In some embodiments a method of applying one or more fluids to a solid support further comprises inserting multiple cartridges into the cartridge slots and performing a pumping sequence on each of the cartridges, where the pumping sequence performed on each cartridge is the same or different than the pumping sequence performed on any other cartridge. In some embodiments, the pumping sequences performed on each of the cartridges are performed at the same time.

In some embodiments, any of the methods of bioprocessing described herein may be stored as a portion of or as a complete bioprocessing protocol on a bioprocessing device. In some embodiments, the stored protocol may further include details delineating timing for each step and the sequence of opening and closing of valves and pumping of pumps on a bioprocessing cartridge.

In some embodiments, the bioprocessing device and cartridges may be used as follows: the bioprocessing device is turned on and the various pressure and vacuum connections and supplies may be checked, one or more samples to be analyzed or bioprocessed are inserted into one or more fluid container holders along with reagents in reagent containers and waste containers as necessary. The one or more fluid container holders are placed in the removable fluid container tray and the tray is pushed into the bioprocessing device. One or more bioprocessing cartridges is inserted into the slots of the bioprocessing device and placed in fluid communication with the fluid containers in the fluid container holders. This fluid communication may be accomplished via a fluid manifold in each slot or may be accomplished by inserting aspiration/expiration tubes connected to each bioprocessing cartridge into the fluid containers. The slots hold the cartridges in place and the control fluid manifold is connected to the cartridges by inflating bladders within the slots that urge supply connectors on the manifolds to engage control fluid connectors on the cartridges. The device performs a systems check to verify that there are no safety issues or connection errors. Using the GUI and an input system, an operator selects a bioprocessing protocol from a menu of stored protocols or may enter a protocol into the automated control system of the device. The protocol selected or entered includes instructions for controlling pumps and valves on the bioprocessing cartridges to perform the steps of one or more bioprocessing procedures. After completion of the procedure, the device may provide an alarm or signal for notifying the operator that the procedure is complete. The cartridges may be removed from the device and disposed of and the fluid containers and fluid container holders may be removed with the removable fluid tray and cleaned and/or disposed of as necessary.

It should be understood that the above process may be modified, including having one or more steps removed, added or the order of one or more steps changed without departing from the scope of the methods described herein.

Referring to FIG. 1A, in some embodiments, a bioprocessing device 100 has a housing 10 which may be constructed from any suitable material, such as plastics, metals, composite materials, or any combination thereof, and which is designed to house the various components of the device. In some embodiments, housing 10 may include a sheet metal chassis that is covered with a plastic cover. The sheet metal chassis may be any suitable sheet metal, such as an aluminum sheet chassis, which may provide for structural integrity to the instrument, may limit EMI emissions and may serve as a heat sink for the power supply. The plastic cover may be constructed from any suitable plastic, such as urethane, and may provide basic protection for the internal components and an easy to clean surface. Housing 10 includes openings 17 for access to slots 13 within the device.

As shown in FIG. 1A, in some embodiments the bioprocessing device 100 has two slots 13 into which a cartridge 12 has been inserted into each slot 13. In general, the bioprocessing devices may have any suitable number of slots, such as from about 1 to about 20 slots, such as about 2 to about 15 slots, about 3 to about 12 slots, from about 4 to about 10 slots, from about 6 to about 8 slots. In some embodiments, only one card 12 and one slot 13 may be used during a run. In some embodiments, every slot 13 may be used with a cartridges 12 during a run. In general, an operator may use keypad 18 to turn the device on and to interact with the device, such as a computer control system or central processing unit included in the device to select various options and perform various functions or provide and/or respond to commands or queries in conjunction with the graphical user interface (GUI) 15, which may provide status information, prompting information, protocol selection information, protocol generation information, protocol storage information and any other suitable information to the operator. In addition, the GUI may be used to override a protocol before or during a run, if needed. The GUI 15 may be any suitable display device, such as for example liquid crystal display (LCD) touchscreens, light emitting diodes (LEDs), or cathode ray tubes (CRTs).

Figure 1B:
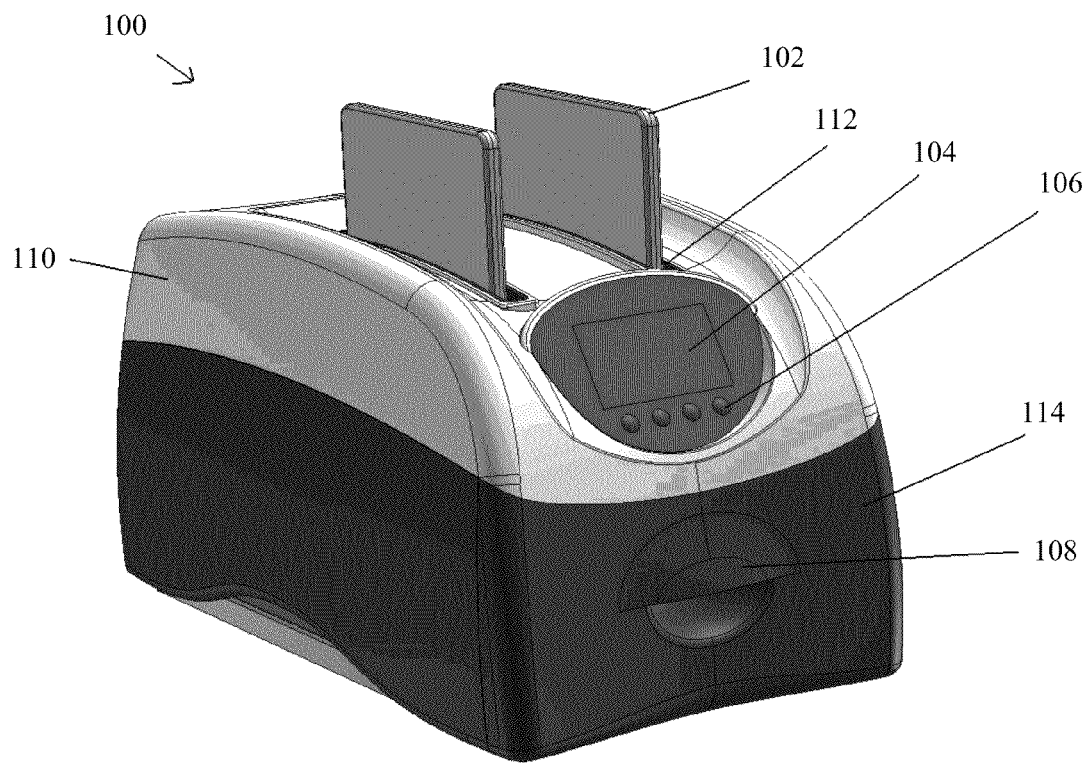

FIG. 1B shows an alternate embodiment of a bioprocessing device 100, as viewed from the front. Bioprocessing device 100 has bioprocessing cartridges 102 inserted into slots 112. As shown in FIG. 1B, bioprocessing device 100 also includes GUI 104, keypad 106, drawer 114 having handle 108, each of which may be incorporated into or surrounded by chassis 110.

Figure 1C:
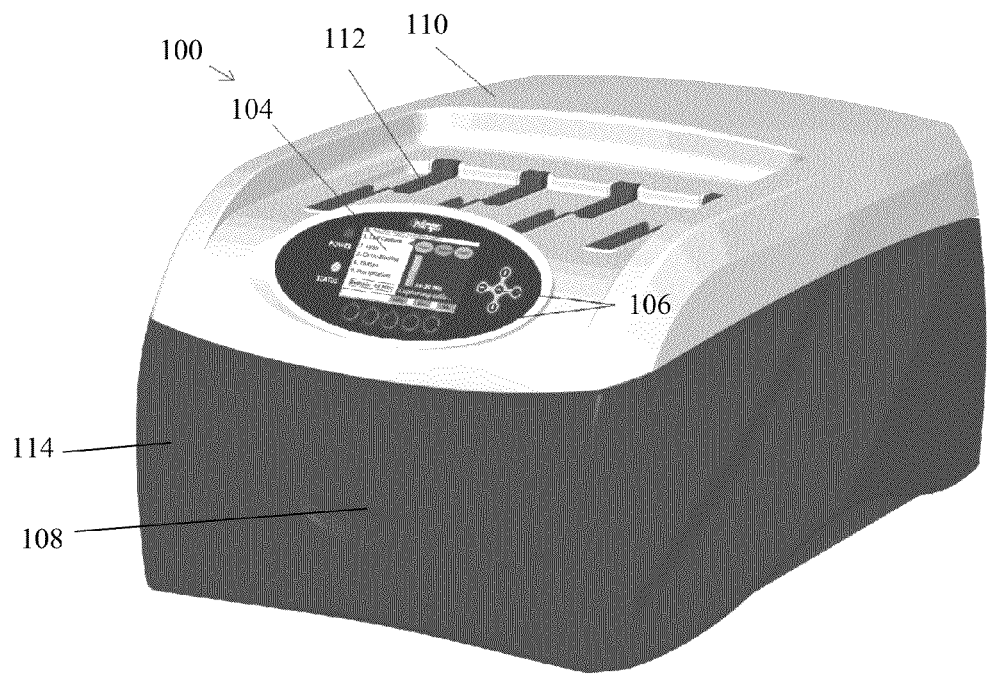
Figure 1D:
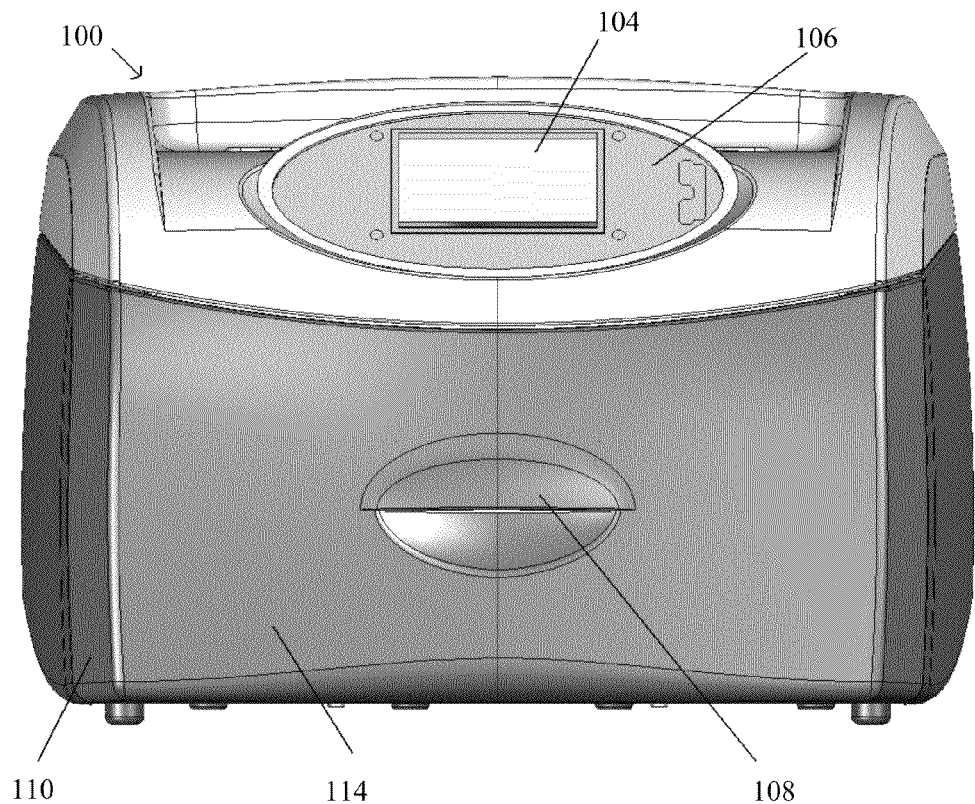

FIG. 1C shows an alternate embodiment of a bioprocessing device 100 including a GUI 104 for displaying information to a user, such as protocol information or status, run information, protocol details, protocol selection, and other options. In some embodiments, the device 100 may be configured with one, two, three, four, or more than four slots 112, which may all be loaded and/or used at the same time, or simultaneously. Bioprocessing device 100 may also include a keypad 106 on the GUI 104 for inputting and selecting options on the device, and a drawer 114 having handle 108, each of which may be incorporated into or surrounded by chassis 110. FIG. 1D shows the bioprocessing device 100 of FIG. 1C as viewed from the front, having a GUI 104 with a keypad 106, a drawer 114, a handle 108, and the surrounding chassis 110.

Figure 2A:
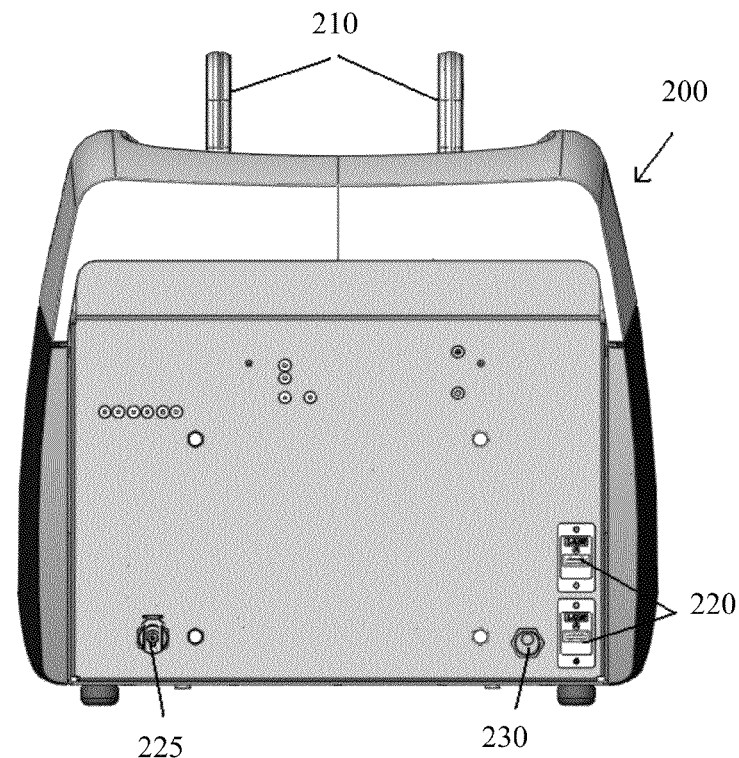
FIGS. 2A-2C depict alternate rear views of a bioprocessing device.

FIG. 2A shows a rear view of an embodiment of a bioprocessing device 200 having cartridges 210 inserted therein. Bioprocessing device 200 has universal service bus (USB) ports 220 which may be used by an operator or a technician to download information from the device, such as for example, protocol run information or device service information from self diagnostic software or firmware that may be installed on the device to compatible storage devices. Alternatively, USB ports 220 may be used to upload software or firmware updates and patches or additional protocols onto a computer control system within the device. Bioprocessing device 200 may also include house or auxiliary air connector 225 for connection of the device to an external air supply, and power connection 230 for connection of the device to a source of electrical power such as a DC or AC power source. In some embodiments of the devices 200, house air and/or house vacuum may be used rather than including a compressor and a vacuum pump within the device.

Figure 2B:
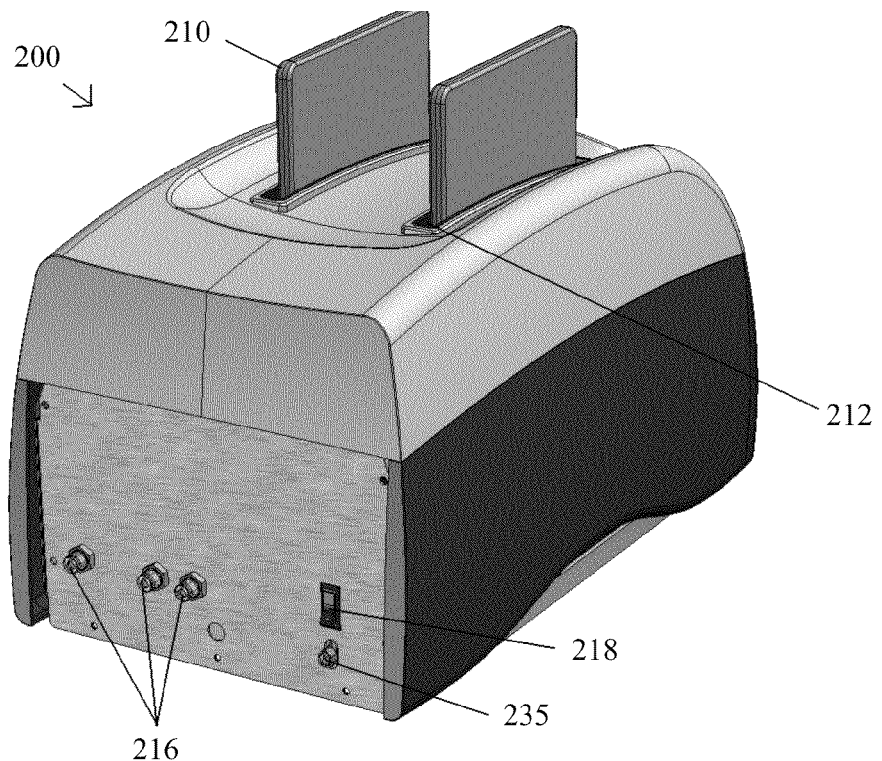
Figure 2C:
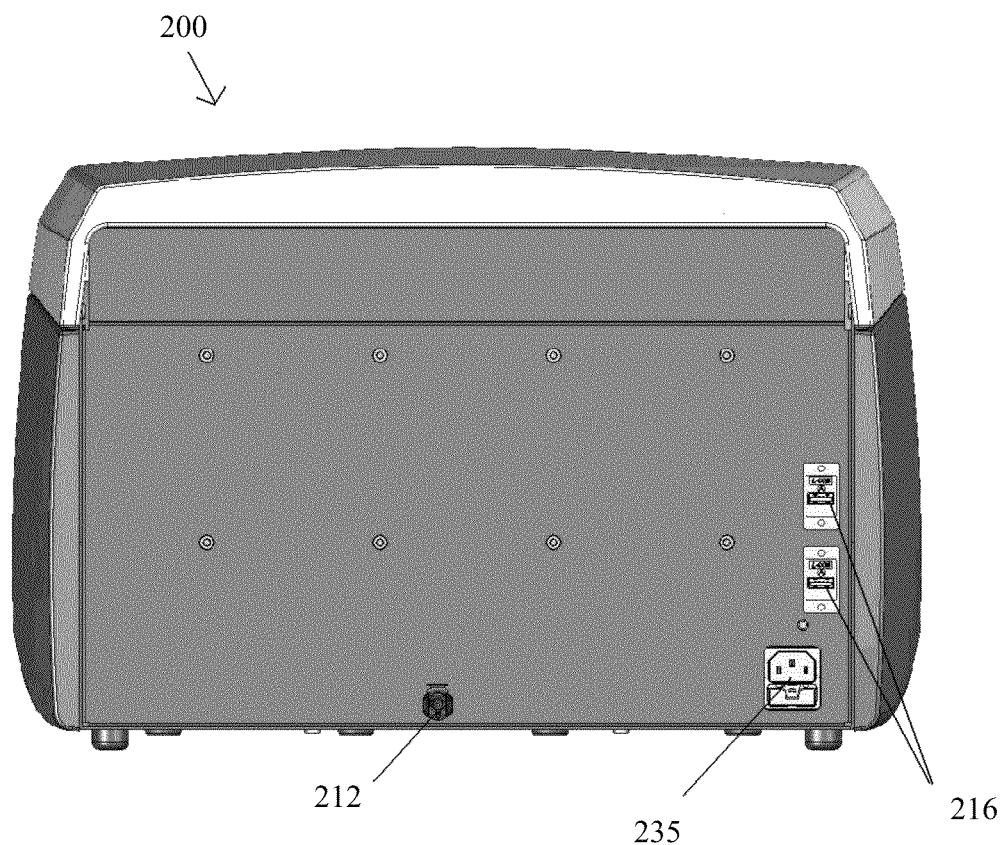

A rear perspective view of an alternate embodiment of the device with cartridges 210 inserted into slots 212 is shown in FIG. 2B. The device shown in FIG. 2B also shows a power switch 218, power cord slot 235 and utility connections 216, which may be used to supply air, vacuum and/or other utilities to bioprocessing device 200. FIG. 2C shows an alternate rear view of a bioprocessing device 200 with USB ports 216, power cord slot 235, and optional reservoir drain connection 212.

Figure 3A:
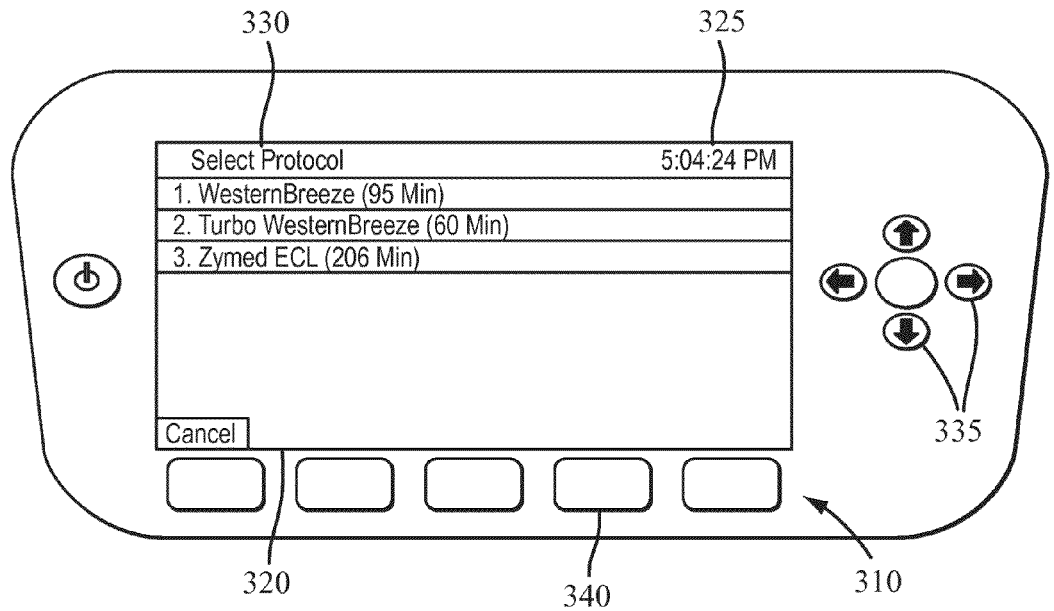
FIGS. 3A & 3B show embodiments of a graphical user interface (GUI)

FIG. 3A shows a view of an embodiment of the keypad 310 and GUI 320 of an embodiment of the bioprocessing device at the protocol selection step 330 of the process. As shown, the user may choose to select one of multiple protocols preloaded on the system. Any number of preloaded protocols may be included with the device and displayed on the GUI 320 including 1 or more protocols, 2 or more, 3 or more, 5 or more, 10 or more protocols, or any other suitable number of protocols that can be loaded into the memory of the GUI 320. In some embodiments, a preloaded protocol may be edited or modified by a user. Additionally, a protocol with user defined parameters may be entered into the GUI 320. The system may also include a time stamp 325. Keypad 310 provides directional buttons 335 for navigating in and to different windows on the GUI 320 and selection buttons 340 for selecting various options depending on the window and commands/functions available.

Figure 3B:
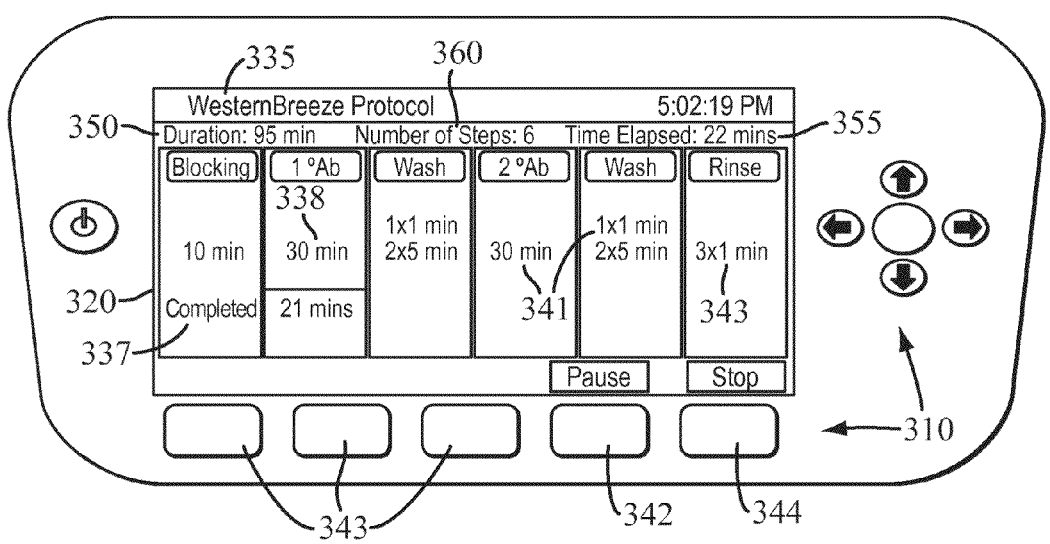

FIG. 3B shows a view of an embodiment of the keypad 310 and GUI 320 of an embodiment of the bioprocessing device while a bioprocessing protocol run is in process. As shown, a Western Breeze protocol 335 has been selected, a blocking step 337 has been completed and a 30 minute primary antibody step 338 is in process. Additional steps 341 to be performed may be displayed with the run times 343 set up for each additional step. Also active on this screen are selection buttons 342 and 344 for pausing or stopping the process respectively. Additional selection buttons 343 may be provided, as shown in FIG. 3B, which may be used to change parameters of a step, advance to the next step before the run time for the current step has been completed, cancel a step, cancel the run, or may be used for any other suitable function. The duration time for the entire protocol 350, the number of steps in the protocol 360, and the time remaining or elapsed 355 on the current step may also be shown on the screen of the GUI 320. It should be understood that the automated control system may provide for changing any of the step durations, the sequence of steps, types of steps, number of steps, display options, alarm options and any other suitable parameters for inputting, running, controlling and recording any suitable protocol on the bioprocessing device and cartridges inserted therein.

Figure 4:
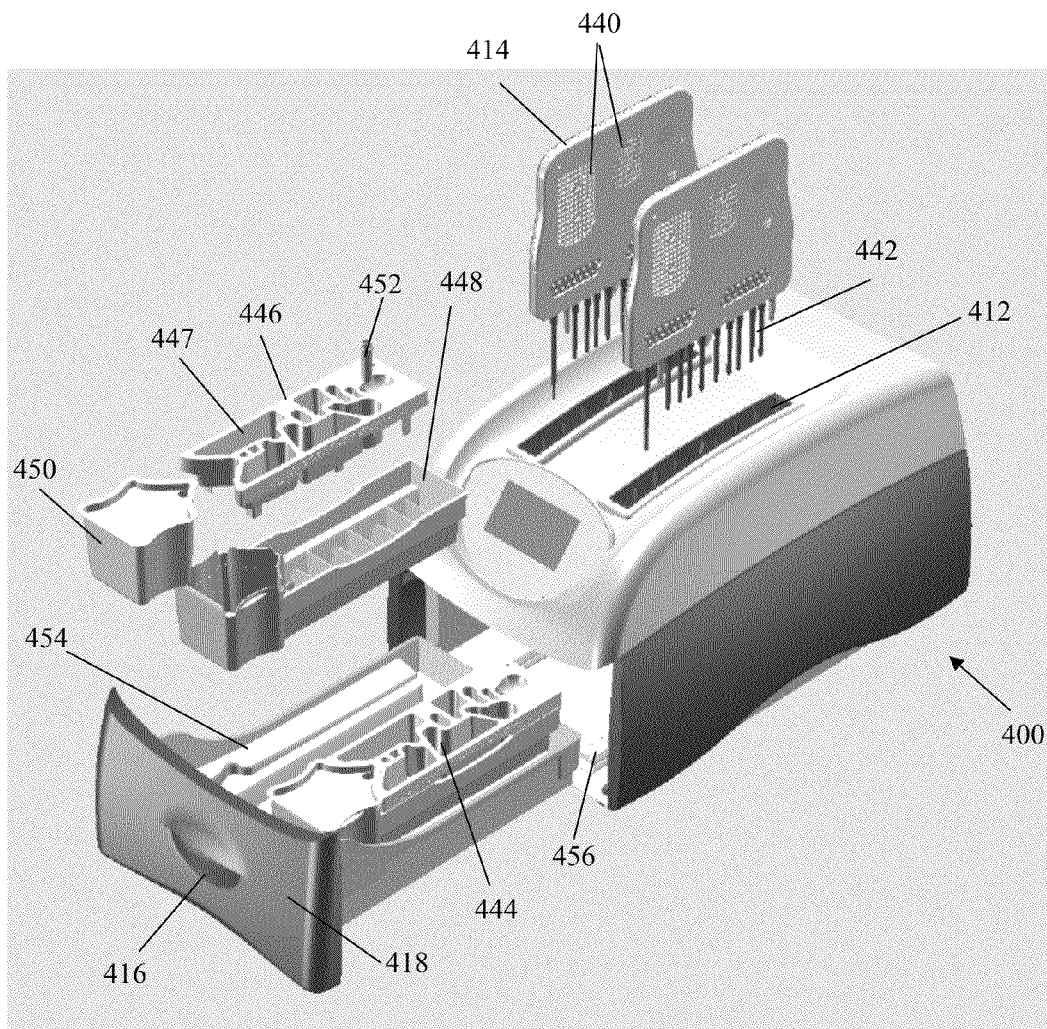
FIG. 4 shows an exploded view of an embodiment of a bioprocessing device.

FIG. 4 illustrates a partially exploded view of an embodiment of a bioprocessing device 400 and relevant components. The device 400 is shown having two slots 412 with two cartridges 414 ready to be positioned within the slots 412 of the device. The two cartridges may include at least one, at least two, at least three, or at least four processing chambers 440 for performing various steps of a protocol run. The cartridges 412 may further include sippers 442 that are in communication, preferably fluid communication, with the fluid reservoirs 444 of the device 400. The drawer 418 of the device 400 may include a handle 416 and is shown in the open position. Drawer slides 456 may be used to facilitate the opening and closing of the drawer 418. In some embodiments, the slides 456 may be located along the bottom of the drawer, or alternatively, may be located along the sides of the drawer. The drawer may have supports 454 for aligning the fluid reservoir tray 446 and waste container 448 in the machine for proper alignment with the sippers 442 on the cartridge 414. The drawer may in some embodiments house at least one fluid reservoir tray 446 and waste container 448. A sample container 450 may be inserted into the waste container 448. The fluid reservoir tray 446 may also be positioned in the waste container 448 and may include at least one reagent reservoir 447 for containing and confining at least one reagent. The fluid reservoir tray 446 may be further configured to hold a collection tube 452 into which the purified sample may be collected.

Figure 5:
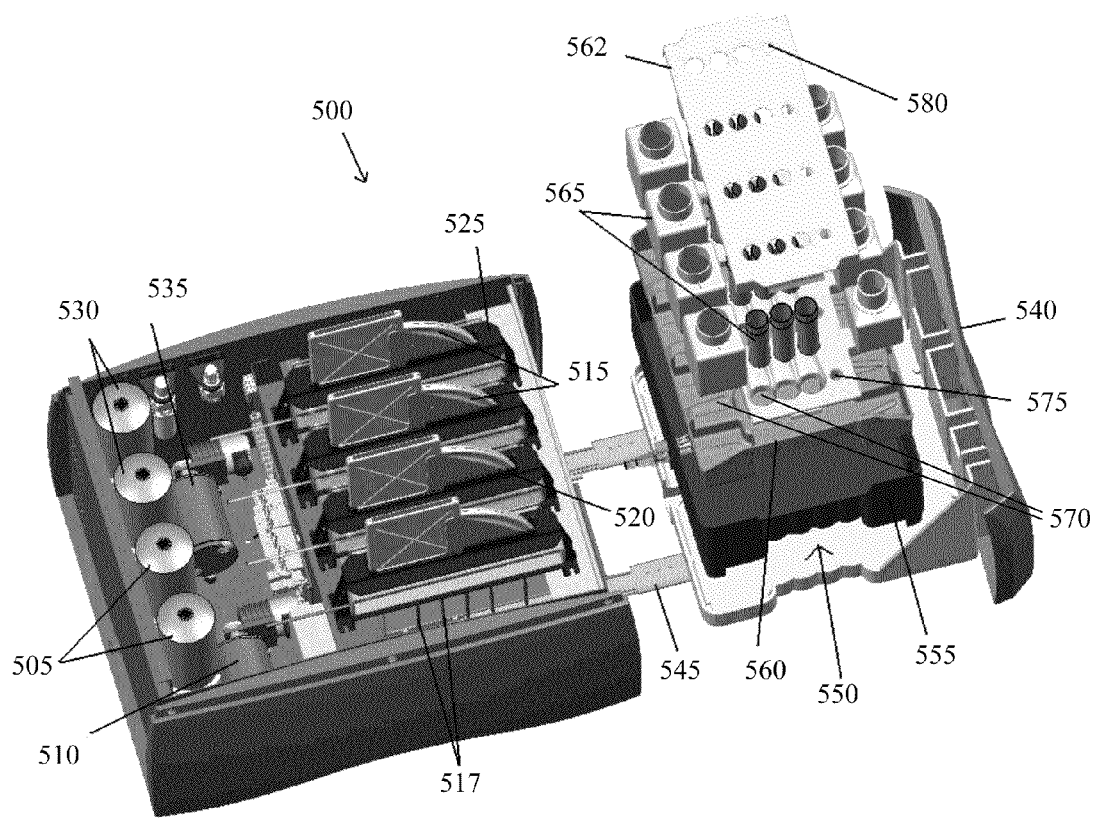
FIG. 5 shows an embodiment of a bioprocessing device with external housing removed.

FIG. 5 shows an embodiment of a bioprocessing device 500 with the external housing removed. Bioprocessing device 500 may include at least one vacuum reservoir 505 and/or at least one vacuum pump 510 for supplying vacuum or suction as needed during processing to the bioprocessing cartridges 515 having aspiration/expiration tubes 517 in slots 520 and cartridge holders 525. Similarly, bioprocessing device 500 includes at least one pressure reservoir 530 and/or at least one compressor 535 for supplying air pressure to the bioprocessing cartridges 515 during processing. In some embodiments, at least one of the vacuum reservoir 505, vacuum pump 510, pressure reservoir 550 and compressor 535 are in fluid communication with the cartridge 515 using tubing or other suitable vacuum or pressure connectors. In some embodiments, a diffuser may be in communication with the vacuum or pressure connectors to self-adjust the level of pressure/suction being delivered to the cartridge. The pressure or vacuum supplied to the cartridge may be controlled according to the configuration of the bioprocessing cartridge or may be a consistent preset pressure (up to 50 psi) and vacuum (up to 20 in Hg). In a specific example, the pumping mechanism of the bioprocessing device has a pneumatic valve response time of 20 ms, an air reservoir capacity of 37.7 in$^3$ (both vacuum and pressure), an air compressor pump duty cycle of 50% duty (both vacuum and pressure), and an air compressor pump pressure of 80 PSI.

As shown, removable fluid container tray 540 may be movably engaged with tray slides 545 which may help guide tray 540 as it is moved into and out of bioprocessing device 500. Tray 540 may house fluid container holder 550, which, in the embodiment shown may comprise waste reservoir 555, container receptacle 560 and container retention plate 562. As shown, containers 565 may be inserted into appropriately sized container slots 570 on container receptacle 560 and container retention plate 562 may be placed atop some or all of the containers 565 to secure the containers 565 in place, for example when dumping excess reagents or waste from the fluid container holder 550. Container receptacle 560 also includes waste reservoir access penetrations 575 which, when aligned with waste aspiration/expiration tube penetrations 580 on container retention plate 562, provides access to the waster reservoir 555 to aspiration/expiration tubes on one or more bioprocessing cartridges 515 that have been inserted into the device. In some embodiments, the fluid container holder 550 is configured such that aspiration/expiration tubes on one or more bioprocessing cartridges align with the appropriate containers or receptacles on the fluid container holder 550 to allow for running of a desired bioprocessing protocol. Alternatively, in some embodiments, the fluid container holder 550 is configured such that a fluid manifold in the bioprocessing device 500 may access the appropriate containers or receptacles on the fluid container holder 550 to allow for running of a desired bioprocessing protocol.

Though shown having a specific configuration, it should be understood that the fluid container holder may have any suitable configuration and that multiple different types, sizes and shapes of containers 565 and configurations of container receptacles 560 may be used depending on the fluid types and volumes required for the individual steps of protocols performed using the bioprocessing device. For example instead of comprising a single integrated fluid container holder that provides slots for housing reagents and samples, multiple individual fluid container holders may be used and placed in the removable fluid container tray or fluid container holders that are sized for all of the fluid containers for a single slot may be used. Similarly, the fluid container holder may be supplied with or without fluid containers and when supplied with fluid containers, one or more or all of the fluid containers may be supplied empty, sterile, clean, pre-filled and/or endotoxin free. In addition, in some embodiments, the fluid container holders and some or all of the reagents and the waste containers may be supplied as part of a pre-filled kit, where the user may only need to supply a sample, where a sample is provided for in the protocol, or one or more of the reagents as necessary.

Figure 6:
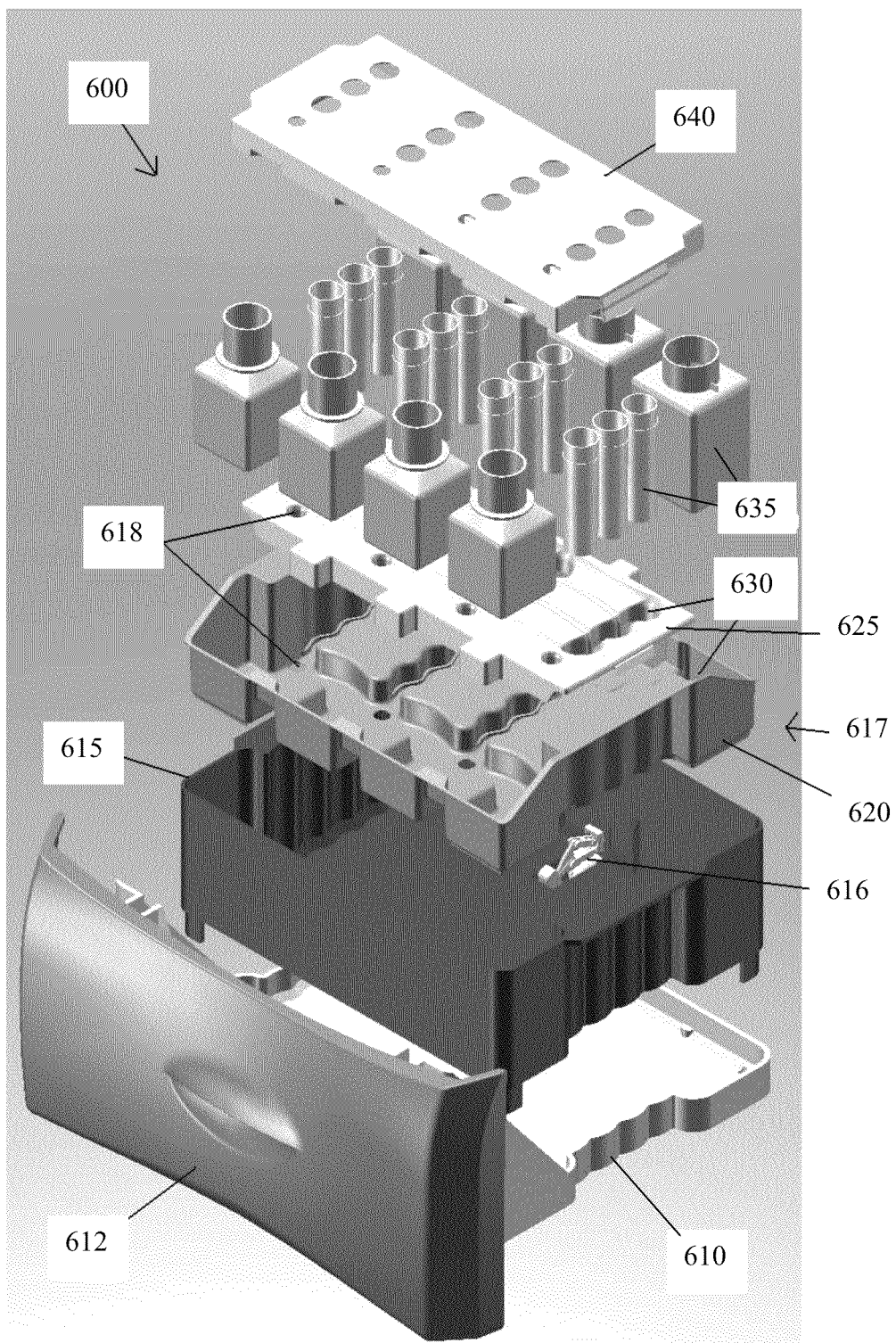
FIG. 6 shows an exploded view of an embodiment of a removable fluid container tray.

Referring to FIG. 6 showing an exploded view of an embodiment of a fluid container holder 600 and removable fluid container drawer 612 and fluid container tray 610, in some embodiments a fluid container holder 600 may comprise a waste reservoir 615, a container receptacle 617 comprising a container holder bottom 620 and a container holder top 625 and having container slots 630 into which containers 635 may be inserted. Waste reservoir 615 may include a waste level sensor 616 that may provide feedback to an automated control system within a bioprocessing device, which may display a notice on the GUI and/or provide for an audible alarm. Waste reservoir 615 may also include a fluid drain nozzle that may fit through a penetration in the housing of a bioprocessing device and may be connected to an appropriate drain or other waste fluid receptacle. Container receptacle 617 may include waste reservoir access penetrations 618 for placing one or more waste lines from a bioprocessing cartridge and/or from a fluid manifold in fluid communication with the waste reservoir 615. Fluid container holder 600 may also include a container retention plate 640. As shown, the fluid container holder 600, when assembled with appropriate containers and reagents and samples as necessary for the desired bioprocessing protocol, may be placed in to removable fluid container tray 610, which may be moved into and out of a bioprocessing device like a drawer.

Figure 7:
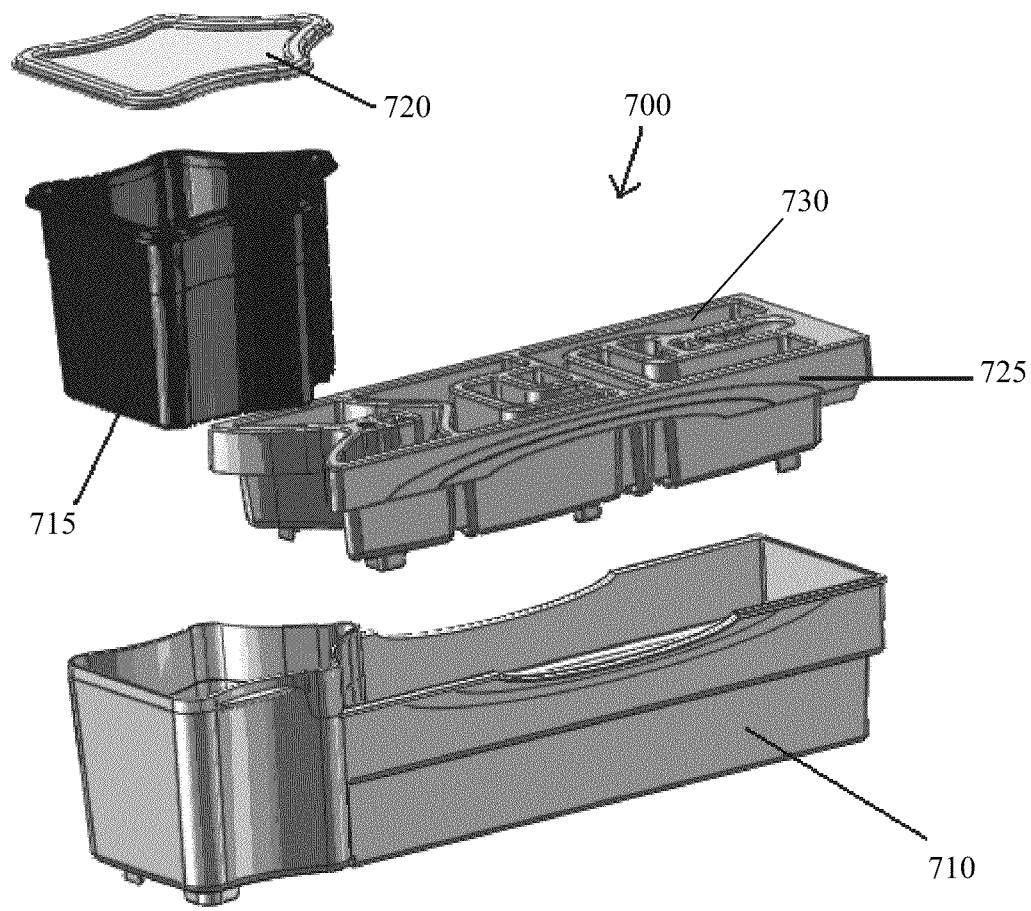
FIG. 7 shows an exploded view of an embodiment of a fluid container holder.

Referring to FIG. 7 in some embodiments, a fluid container holder 700 may be provided that includes a container receptacle 710, which may also serve as a waste reservoir, a sample container 715, which may include a sample container lid 720, and a reagent reservoir tray 725, which may include multiple reagents reservoirs 730 for containing reagents as part of a pre-filled kit, or may include one or more empty reagent containers or empty reagent receptacles for containing a reagent. In some embodiments, where the all or some of the reagent reservoirs are pre-filled, the reagent tray may be all or partially covered with an aluminum, plastic, or any other suitable film, which can then be broken prior to usage either before the tray is inserted into the device or after the tray has been positioned in the device. The reagent or reagents may be buffers, including but not limited to, wash buffers, lysis buffers, neutralization buffers, resuspension buffers, precipitation buffers or any other suitable buffer, or other suitable reagents, such as antibodies, standards, blocking solutions, deionized water. In some embodiments, the reagent may be ETOH, e.g. 70% ETOH (70% ETOH with 30% NanoPure water, isopropanol, Genomed wash solution, Genomed elution solution, Rnase, or any other suitable reagent, rabbit antibodies, bovine serum albumin (BSA), standards such as MagicMark™ standard, and chemiluminescent anti-antibodies, such as Western Breeze® Chemiluminescent kit-Anti-Rabbit. The system may be suitable for use with all chromogenic, chemiluminescent, and fluorescent immunodetection reagents and protocols. In some embodiments, the reagents may be supplied as pre-filled reagents in appropriate sized reagent vials and bottles. In some embodiments, the reagents may be added to supplied reagent bottles and/or vials that are placed in the reagent tray of the device. The fluid container lid 720 may include an access penetration to allow for placing of a sample into sample container 715 and for processing of the sample on a bioprocessing cartridge. In some embodiments, the fluid container holder 700 is configured such that aspiration/expiration tubes on one or more bioprocessing cartridges align with the appropriate containers or receptacles on the fluid container holder 700 to allow for running of a desired bioprocessing protocol. Alternatively, in some embodiments, the fluid container holder 700 is configured such that a fluid manifold in a bioprocessing device may access the appropriate containers or receptacles on the fluid container holder 700 to allow for running of a desired bioprocessing protocol.

Figure 8A:
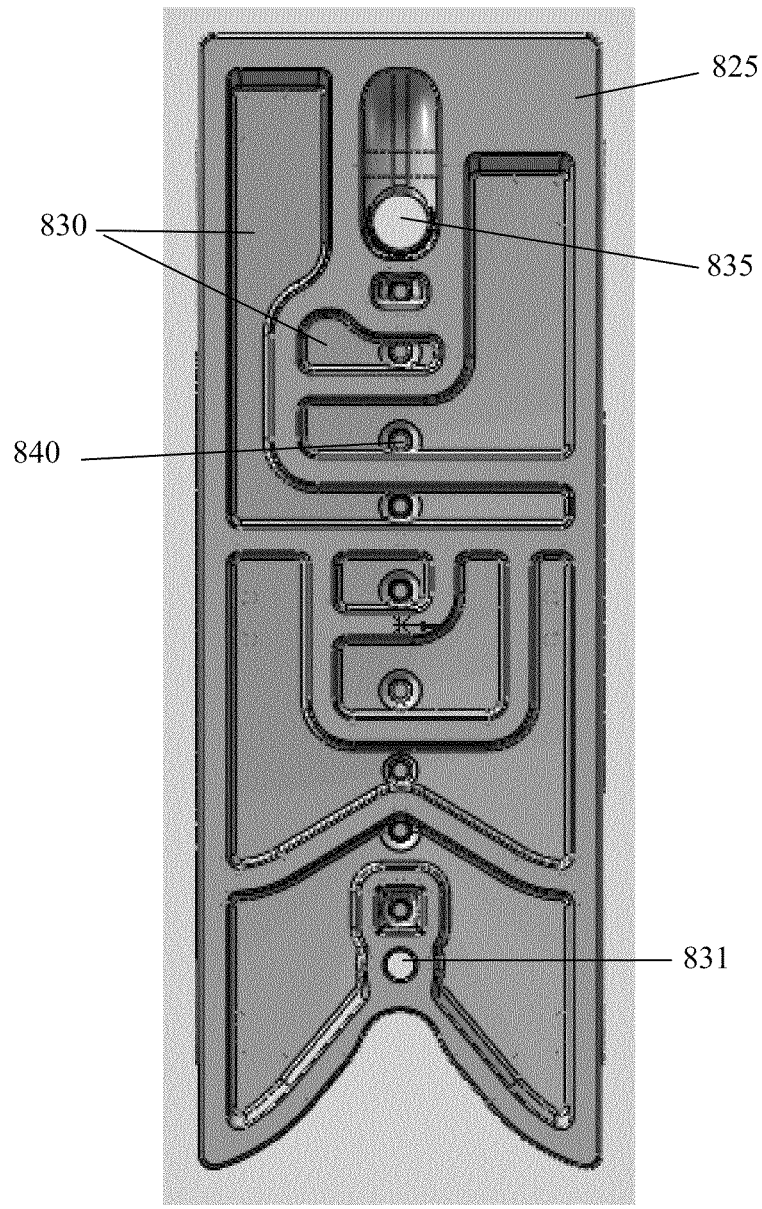
FIGS. 8A-8G show various views and embodiments of a reagent tray and reagent reservoirs.
Figure 8B:
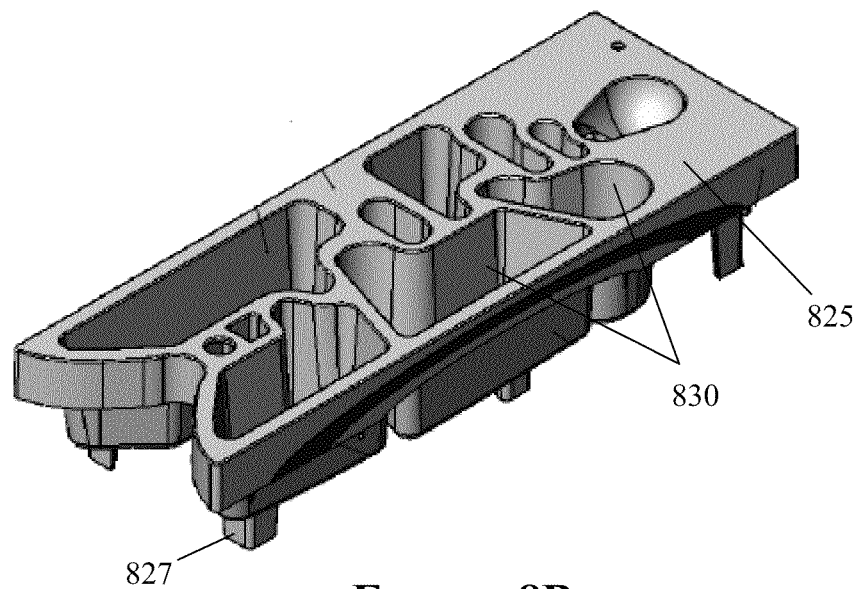
Figure 8C:
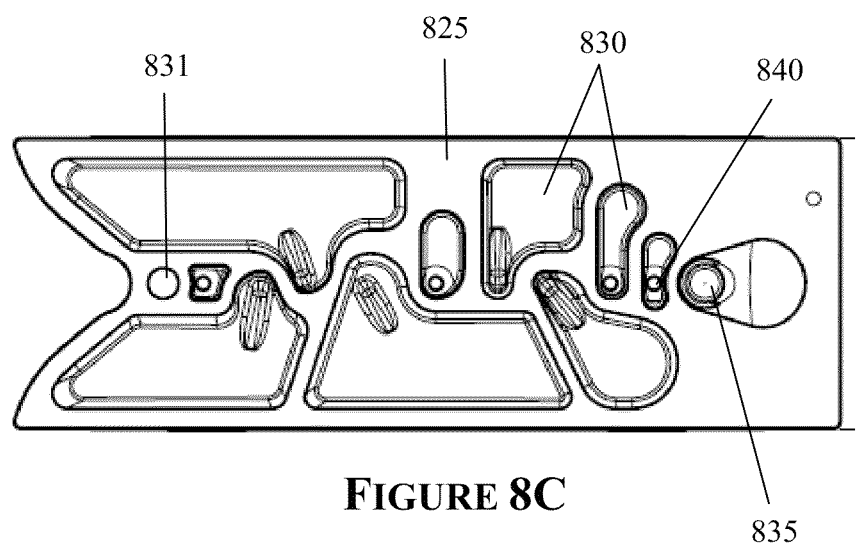
Figure 8D:
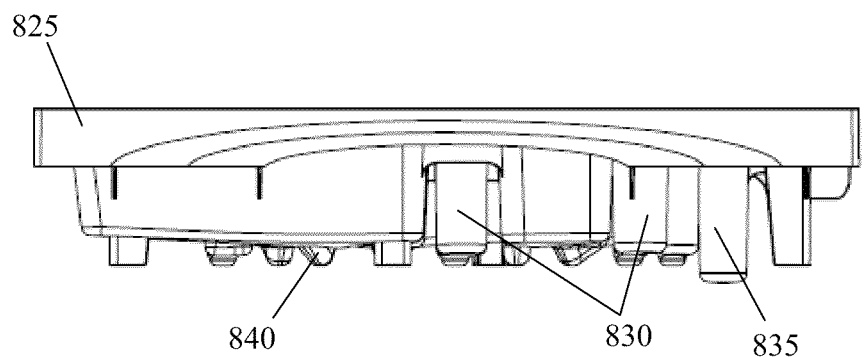
Figure 8E:
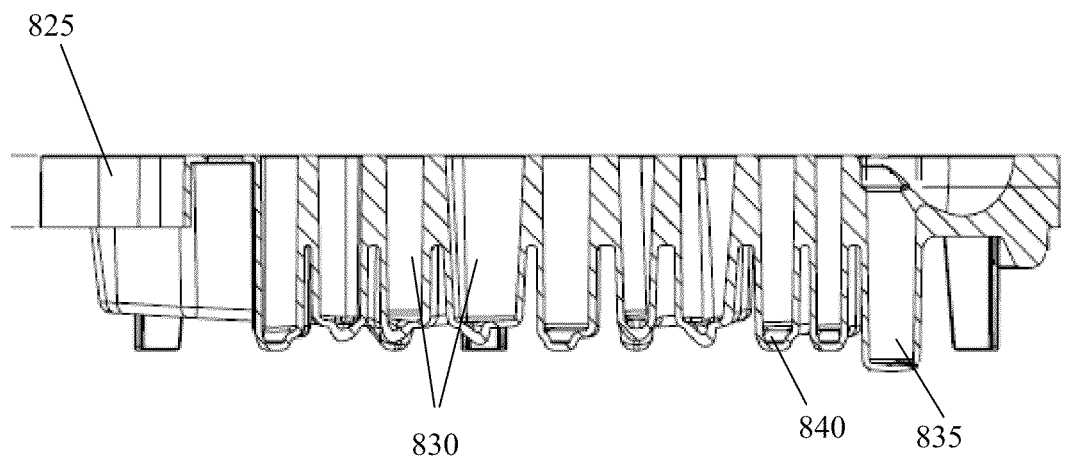
Figure 8F:
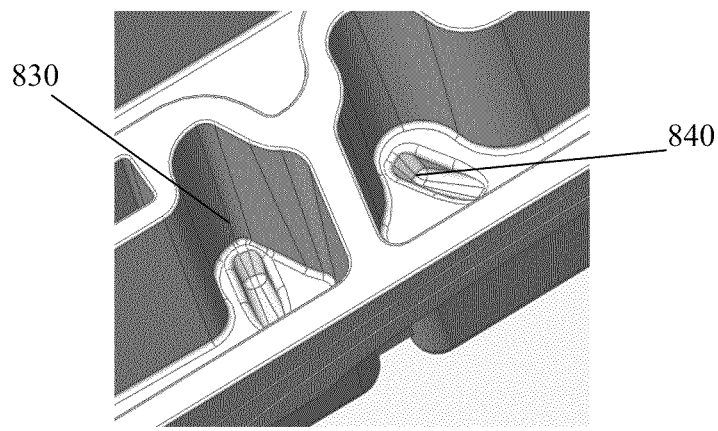
Figure 8G:
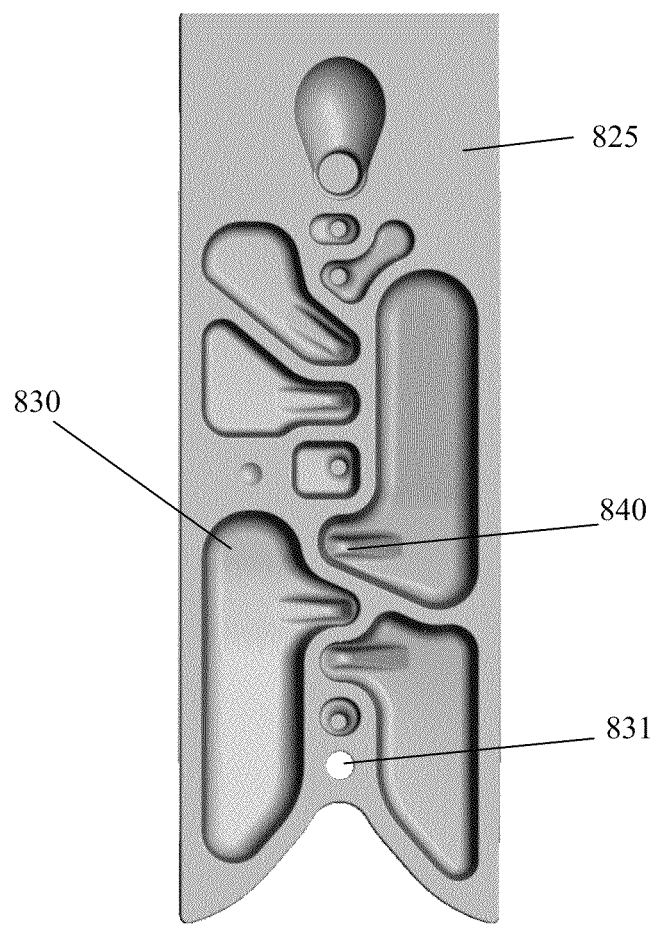

FIG. 8A shows an embodiment of a reagent reservoir tray 825. The reagent reservoir tray 825 may have between about 1 and about 15, between about 1 and about 10, between about 1 and about 7, between about 1 and about 5, between about 1 and about 3 reagent reservoirs 830. In some embodiments, the reagent reservoir tray 825 may include at least 1 reagent reservoir, at least 2 reagent reservoirs, at least 5 reagent reservoirs, or at least 12 reagent reservoirs. The shape of the reagent reservoir 830 may be circular, square, polygonal, or any other suitable shape for containing a reagent of suitable volume for containing a desired amount of reagent. In some embodiments, the reagent reservoir tray 825 may further include at least one tube holder 835 into which a collection tube or container for collecting a purified sample can be inserted. The tube holder 835 may either be a hole into which a collection tube may be inserted or may be a structure for receiving and supporting a collection tuber inserted therein. In some embodiments, the reagent reservoir tray may comprise more than one tube holder. In some embodiments, the tube holder 835 may be configured to hold a collection tube with a volume of about 100 uL, about 1 mL, about 2 mL, about 5 mL, or about 10 mL tube. The reagent reservoirs 830 may further comprise at least one sipper 840 in the reagent reservoir which is in preferably fluid communication with a portion of the bioprocessing cartridge. The sippers 840 may be configured in any suitable configuration for allowing the reagent in the reagent reservoir to collect in the sipper 840 and thereby allowing a substantial part of the reagent to be in introduced into a bioprocessing cartridge and at the same time reducing bubbles from entering the bioprocessing cartridge. In some embodiments, the reagent reservoir tray 825 may include an opening 831 to provide fluid communication to a waste tray A perspective view of an alternate embodiment of a reagent reservoir tray 825 with alternate embodiments/configurations of reagent reservoirs 830 is shown in FIG. 8B. In some embodiments, the reagent reservoir tray 825 may include posts 827 for supporting and/or positioning the reagent reservoir tray 825 in the drawer and/or waste tray. The reagent reservoir tray 825 may include at least one reagent reservoir 830 for containing and confining a reagent, at least one tube holder 835, and at least one opening 831 to waste, as shown in FIG. 8C. In some embodiments, at least one reagent reservoir 830 may further include a sipper 840 configured to facilitate the movement of reagent between the bioprocessing cartridge and the individual reagent reservoirs 830 of the reagent reservoir tray 825. FIG. 8D is a side view of the reagent reservoir tray 825 showing the reagent reservoirs 830, the tube holder 835, and sippers 840. The reagent reservoirs 830 may be substantially the same depth with respect to each other or they may vary with respect to each other. In some embodiments, the depth of the individual reagent reservoirs 830 may depend on the length of the aspiration/expiration tubes of the cartridge. FIG. 8E is a cross-sectional view of a reagent reservoir tray 825 showing the tube holder 835, the reagent reservoirs 830 and the sippers 840 located at the bottom of each reservoir 830. FIG. 8F is a close-up view of the sippers 845 located in the bottom of two different reagent containers 830. FIG. 8G illustrates an embodiment of a reagent reservoir tray as viewed from the bottom of the tray, the sippers 840 extending from the bottom of each reagent reservoir 830, and the opening 831 to waste. The reagent reservoir tray can be configured to hold a suitable number and/or amount of reagents, for example purposes only, the reagent reservoir tray 825 may include at least of a one collection tube slot or tube holder, a TE buffer reservoir, and 70% Ethanol reservoir, an isopropyl reservoir, an elution buffer reservoir, a resuspension buffer reservoir, and a wash buffer reservoir.

Figure 9A:
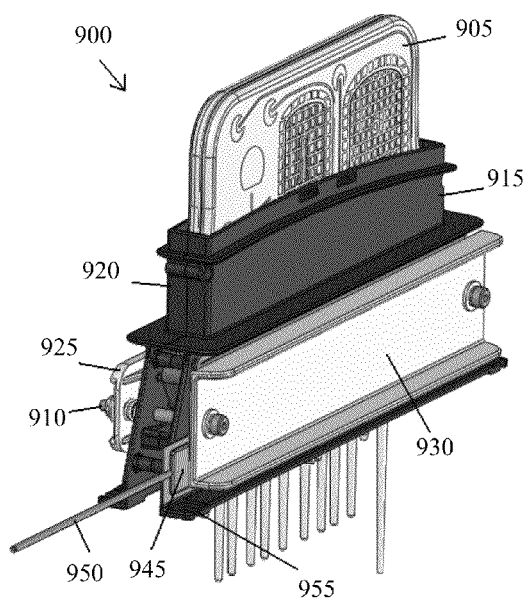
FIGS. 9A & 9B show perspective views of an embodiment of a cartridge holder.
Figure 9B:
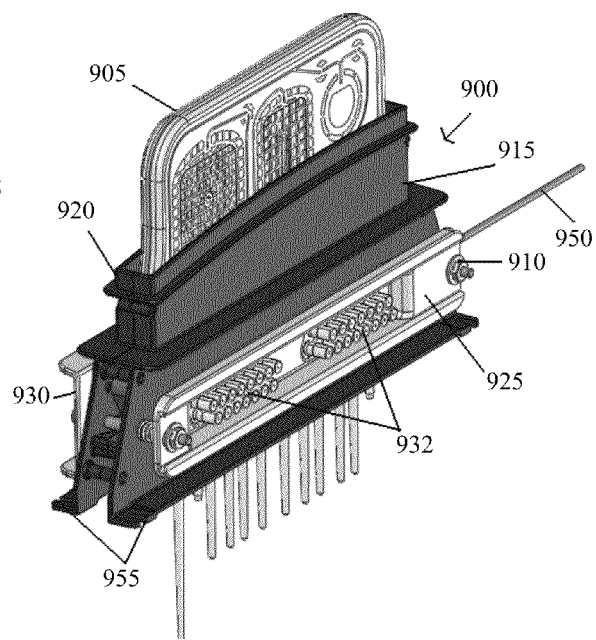

FIGS. 9A and 9B show opposite side perspective views of an embodiment of a cartridge holder 900 with a bioprocessing cartridge 905 inserted therein. As shown, cartridge holder 900 includes spring loaded housing bolts 910 which provide for connection of opposing holder sides 915 and 920 via interaction with support plates 925 and 930. Support plate 930 may include individual supply connectors 932 (as shown in FIG. 9B) as part of a manifold for supplying control fluids to a bioprocessing cartridge. The individual supply connectors 932 may provide connection of a control fluid manifold to control fluid connectors on bioprocessing cartridge 905. Cartridge holder 900 may also include an inflatable bladder or sack 945, which may be connected to a pressure source via a bladder inflation/deflation line 950. Cartridge holder 900 may also include attachment slots 955 that may provide for attachment of holder 900 in a slot of a bioprocessing device.

Figures 10A, 10B:
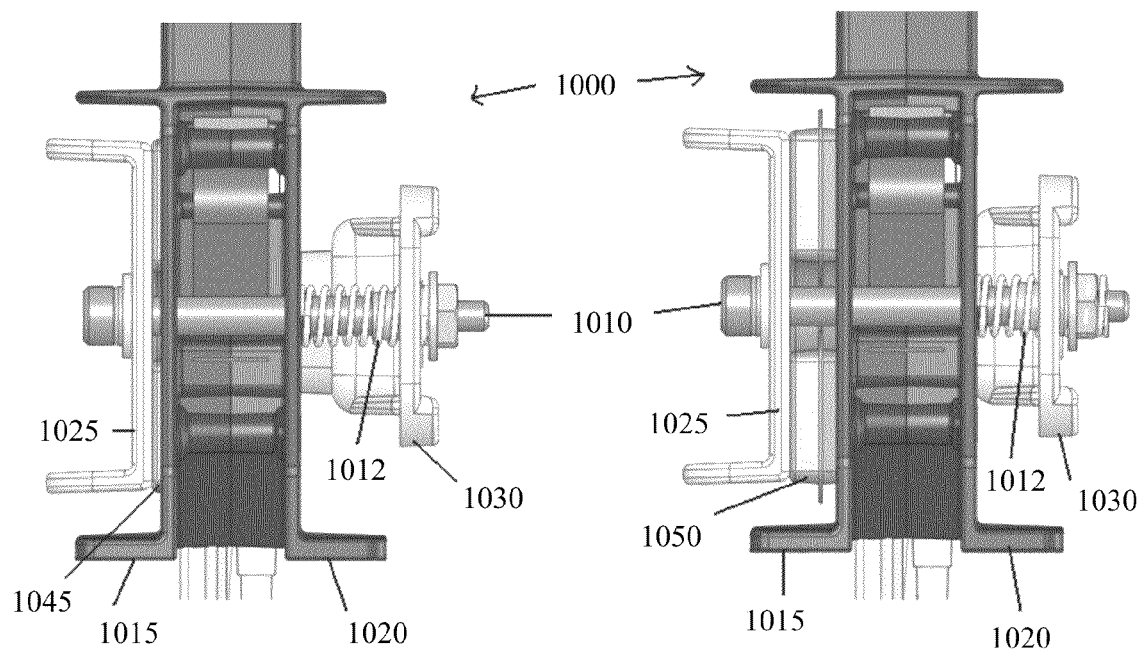
FIGS. 10A and 10B show side views of an embodiment of a cartridge holder.

FIGS. 10A and 10B show side views of a cartridge holder 1000 of a bioprocessing device. As shown, cartridge holder 1000 includes spring loaded housing bolts 1010 which include spring 1012 for urging support plate 1030 apart from support plate 1025, while urging opposing holder sides 1015 and 1020 together. Also shown in FIG. 10A is inflatable bladder or sack 1045 in a deflated state. Upon inflation of the bladder 1045, cartridge holder appears as shown in FIG. 10B, showing inflated bladder 1050 urging the two opposing holder sides 1015 and 1020 as a unit towards support plate 1030, thereby compressing spring 1012. In this manner, by holding support plate 1025 stationary, the opposing holder sides 1015 and 1020 housing and a bioprocessing cartridge held therein may be moved towards support plate 1030. In this manner (and as shown in better detail in FIGS. 11A and 11B), the control fluid connectors of a bioprocessing cartridge may be urged into fluid communication with supply connectors on support plate 1030 and the supply connectors may be connected to the control fluid manifold. In some embodiments, pressure and vacuum may be provided to the bioprocessing cartridges to control the opening and closing of valves and to control the actuation of pumps, thereby controlling the flow of fluids throughout the channels in a bioprocessing cartridge. It should be understood that other mechanisms of achieving the connection between the control fluid connectors and the supply connectors may be used include manual latches, locking latches, mechanical or electrically driven connections and the like.

Figure 11A:
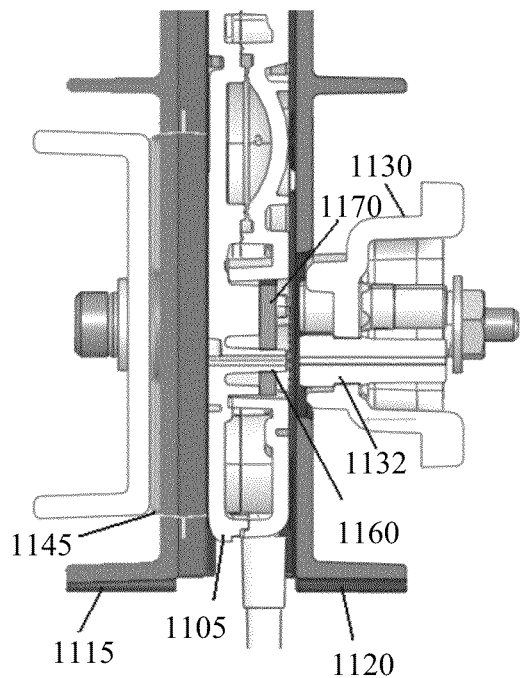
FIGS. 11A and 11B show cross-sectional views of an embodiment of a cartridge holder.
Figure 11B:
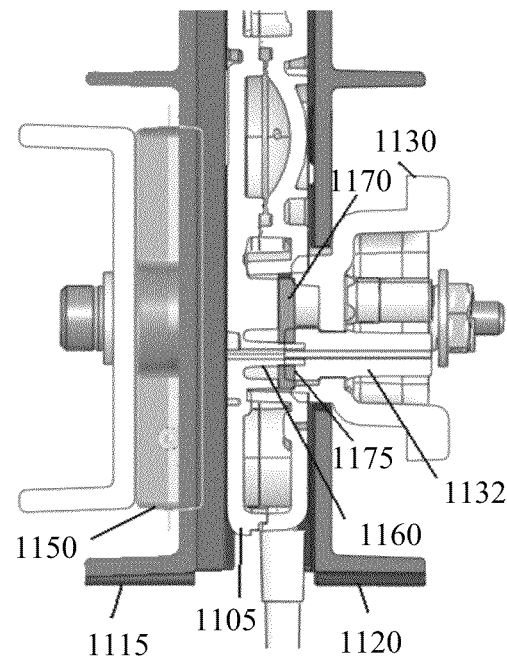

FIGS. 11A and 11B show cross-sectional views of an embodiment of the cartridge holder 1000 shown in FIGS. 10A and 10B. As shown in FIGS. 11A and 11B, when bladder 1145 is in a deflated state as shown in FIG. 11A, control fluid connectors 1160 on bioprocessing cartridge 1105 are not engaged with supply connectors 1132 on support plate 1130. Upon inflation of bladder 1145 to form inflated bladder 1150, the opposing holder sides 1115 and 1120 and bioprocessing cartridge 1105 held therein are moved towards support plate 1130 and supply connectors 1132, compressing gasket 1170 and forming a seal 1175 between the supply connectors 1132, the gasket 1170 and the control fluid connectors 1160 and placing the supply connectors 1132 in fluid communication with control fluid connectors 1160.

Figure 12:
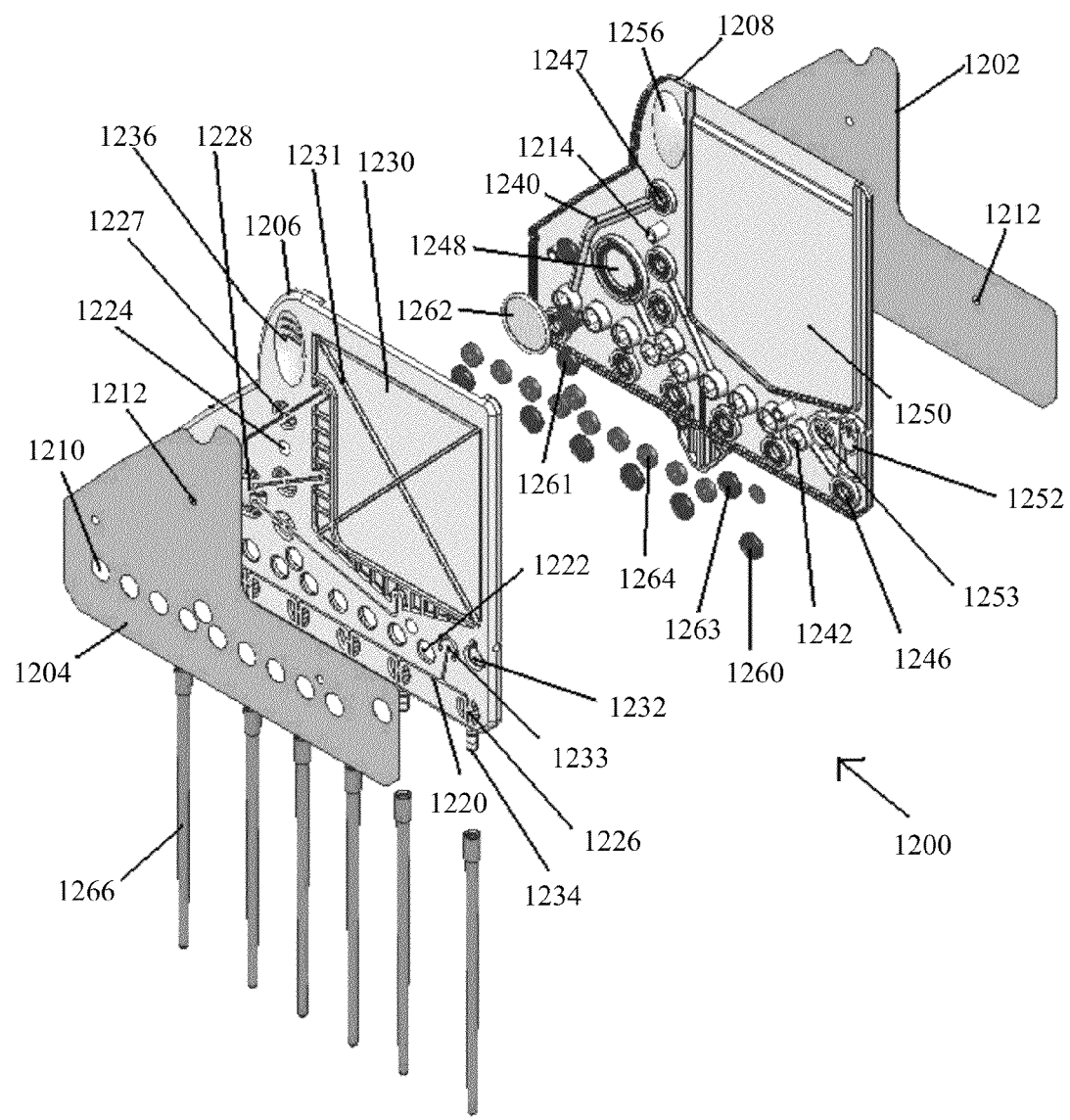
FIG. 12 shows an exploded view of an embodiment of a bioprocessing cartridge.

FIG. 12 shows an exploded view of an embodiment of a bioprocessing cartridge 1200. Cartridge 1200 has two film or foil layers 1202 and 1204 which may be sealed, such as heat sealed onto the exterior face of the process fluid layer 1206 and the exterior face of the control layer 1208 of the cartridge 1200. The film layers 1202, 1204 may comprise any suitable plastic film, such as coated plastic film, or suitable metallic film, such as metallic foils or coated metallic foils, including aluminum foils, and the films may be coated with any appropriate coating and/or adhesives, such as heat seal adhesive. In some embodiments, the film may be a PET film with a PE tie layer that is coated with a heat seal adhesive on the face that is in contact with the process fluid layer 1206 or control layer 1208. In other embodiments, the film layers may comprise aluminum foil that is coated with a heat seal adhesive on the face that is in contact with the process fluid layer 1206 or control layer 1208. The film layers may include penetrations 1210 for the control fluid connectors, penetrations 1212 for alignment guides 1214 for aligning the process fluid layer 1206 and the control layer 1208. In some embodiment, the card may include a penetration to provide viewing access to a color indicator chamber. When sealed onto the relevant surface of the cartridge 1200, the film layers 1202 and 1204 may form the final wall for the process fluid channels 1220 on fluid layer 1206 and the control fluid channels 1240 on control layer 1208.

The cartridge 1200 may include a process fluid layer 1206 having multiple process fluid channels 1220 and multiple penetrations 1222 through which control fluid connectors may be placed, and multiple penetrations 1224 for alignment guides. Process fluid channels 1220 may span the entire process fluid layer 1206. Alternatively, the process fluid channels may be open on the front or exterior surface of the layer and not open on the back or interior surface of the layer. In this manner, process fluid channels 1220 may be isolated from the control fluid layer 1208, except where layer pass-throughs or pass-through valves are provided and when applied to the process fluid layer 1206, film layer 1202 may complete the walls of the process fluid channels 1220. In addition, process fluid layer 1206 may include access valve compartments 1226, process valve compartments 1227, pump compartment 228, bioprocessing compartment 1230 having support ribs 1231, color indicator compartment 1232, check valve compartment 1233, process fluid connectors 1234 and gripper 1236.

Cartridge 1200 may also include control fluid layer 1208 having control fluid channels 1240 and control fluid connectors 1242. Control fluid channels 1240 may span the entire control fluid layer 1208 or alternatively, may instead be open on the back or exterior surface of the layer and not open on the front or interior surface of the layer. In this manner, control fluid channels 1240 may be isolated from the process fluid layer 1206, except where layer pass-throughs or pass-through valves are provided and, in some embodiments, when applied to the control fluid layer 1208, a film layer 1204 may complete the walls of the control fluid channels 1240. In addition, control fluid layer may include at least one of access valve compartments 1246, process valve compartments 1247, pump compartment 1248, bioprocessing compartment 1250, color indicator compartment 1252, check valve compartment 1253 and gripper 1256.

Cartridge 1200 may also include access valve membranes 1260, process valve membranes 1261, pump membrane 1262, and gaskets 1264 between the interior faces of the process fluid layer 1206 and the control fluid layer 1208. In some embodiments, the cartridge 1200 may include at least one check valve membrane 1263. In the embodiment shown, aspiration/expiration tubes 1266 are also included as part of cartridge 1200. When assembled, access valve membranes 1260 fit into compartments formed by the access valve compartments 1226 and 1246 on the process fluid layer 1206 and control fluid layer 1208 to form the access valves sealed by pinching the membranes between the two layers. Fluid may flow into the valves via process fluid channels 1220 connected to the process fluid side of the valve membranes and the valves may be opened or closed using pressure or vacuum supplied using the control fluid channels 1240 on the control fluid side of the valve membranes. In this manner, process valves may be formed by fitting the process valve membranes 1261 into compartments formed by the process valve compartments 1227 and 1247, the pump may be formed by fitting the pump membrane 1262 into the pump compartments 1228 and 1248, the bioprocessing chamber may be formed by aligning the bioprocessing compartments 1230 and 1250, the color indicator chamber may be formed by aligning the color indicator compartments 1232 and 1252, the check valve, if present, may be formed by fitting the check valve membrane 1263 into the check valve compartments 1233 and 1253 and the control fluid connectors 1242 may be provided with sealing gaskets by placing the gaskets over the control fluid connectors 1242 and allowing the smaller opening of the control fluid connector penetrations 1222 on the process fluid layer 1206 to hold the gasket in place. As shown, in this embodiment, the bioprocessing chamber formed by the bioprocessing compartments 1230 and 1250 may be open at the top for access by a user. In addition, the films 1202 and 1204 may be sealed to the exterior surfaces of the process fluid layer 1206 and control layer 1208 sealing the fluid channels 1220 and 1240 and forming one wall for the channels.

Figures 13A, 13B:
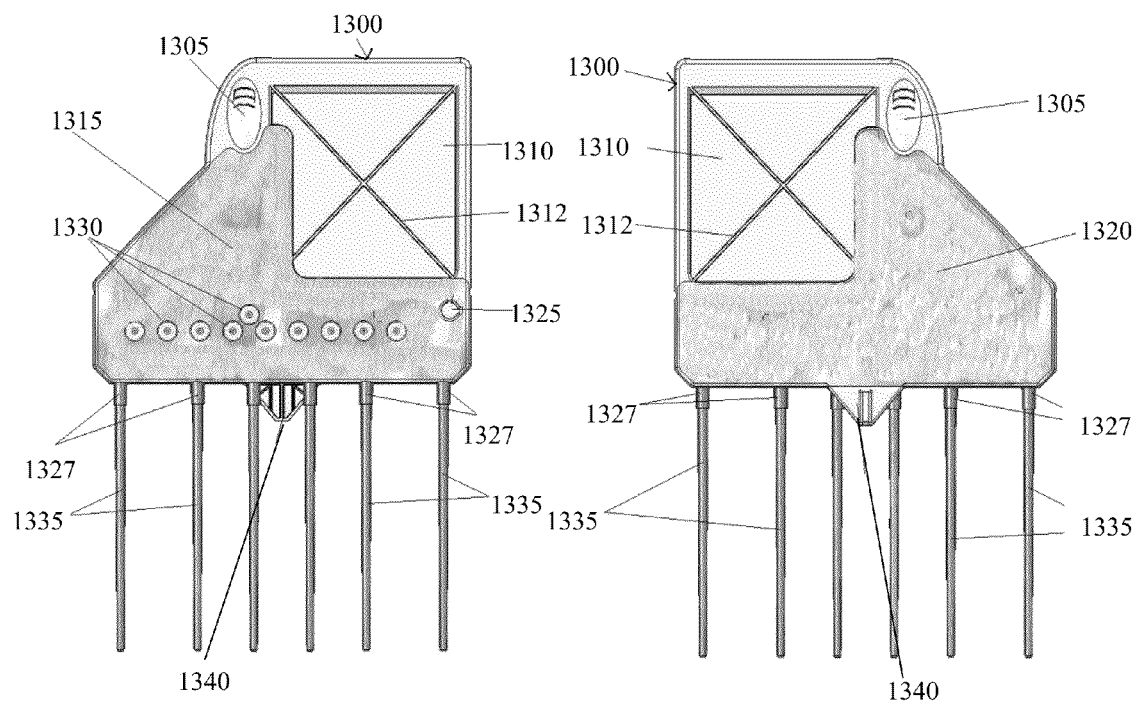
FIGS. 13A & 13B show front and rear views of an embodiment of a bioprocessing cartridge, respectively.

When assembled, the bioprocessing cartridge of FIG. 13 may appear as shown, with front and back views respectfully in FIGS. 13A and 13B. As shown, the visible portions of the cartridge 1300 when assembled may include grippers 1305, bioprocessing chamber 1310 with support ribs 1312, film layers 1315 and 1320, color indicator chamber 1325, process fluid connectors 1327, control fluid connectors 1330, aspiration/expiration tubes 1335 and slot alignment guide 1340.

Figure 14:
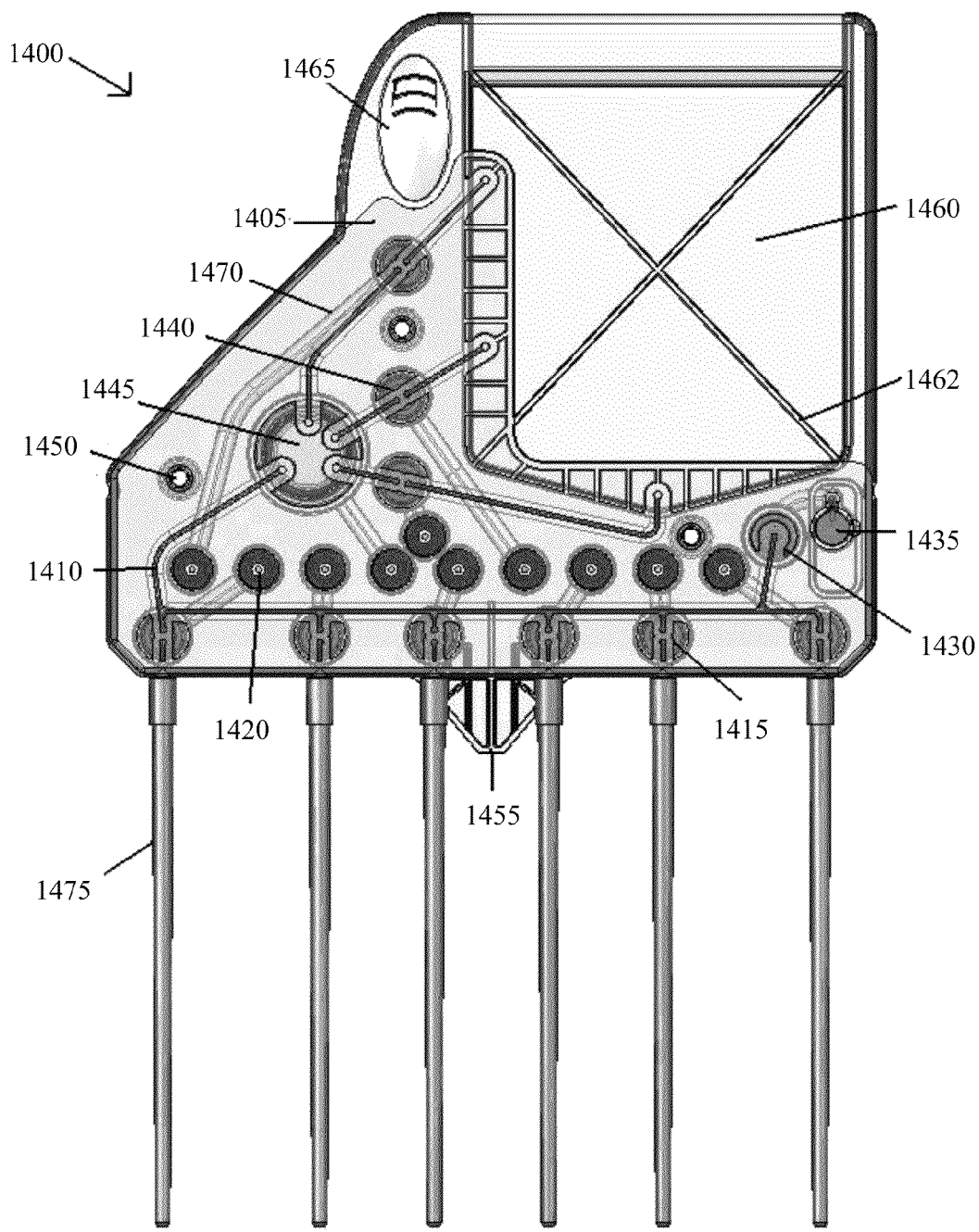
FIG. 14 shows a transparent view of an embodiment of a bioprocessing cartridge showing front and rear layers.

In addition, a transparent view of the assembled bioprocessing cartridge of FIG. 13 is shown in FIG. 14. As shown, bioprocessing cartridge 1400 is viewed through film layer 1405 on the surface of the process fluid layer and the view extends through each of the layers from the front. FIG. 14 shows process fluid channels 1410 on the process fluid layer, access valves 1415, control fluid connectors 1420, check valve 1430, color indicator chamber 1435, process valves 1440, pump 1445, alignment guides 1450, slot alignment guide 1455, bioprocessing chamber 1460 with support ribs 1462, gripper 1465, control fluid channels 1470 on the control fluid layer and aspiration/expiration tubes 1475.

Figure 15:
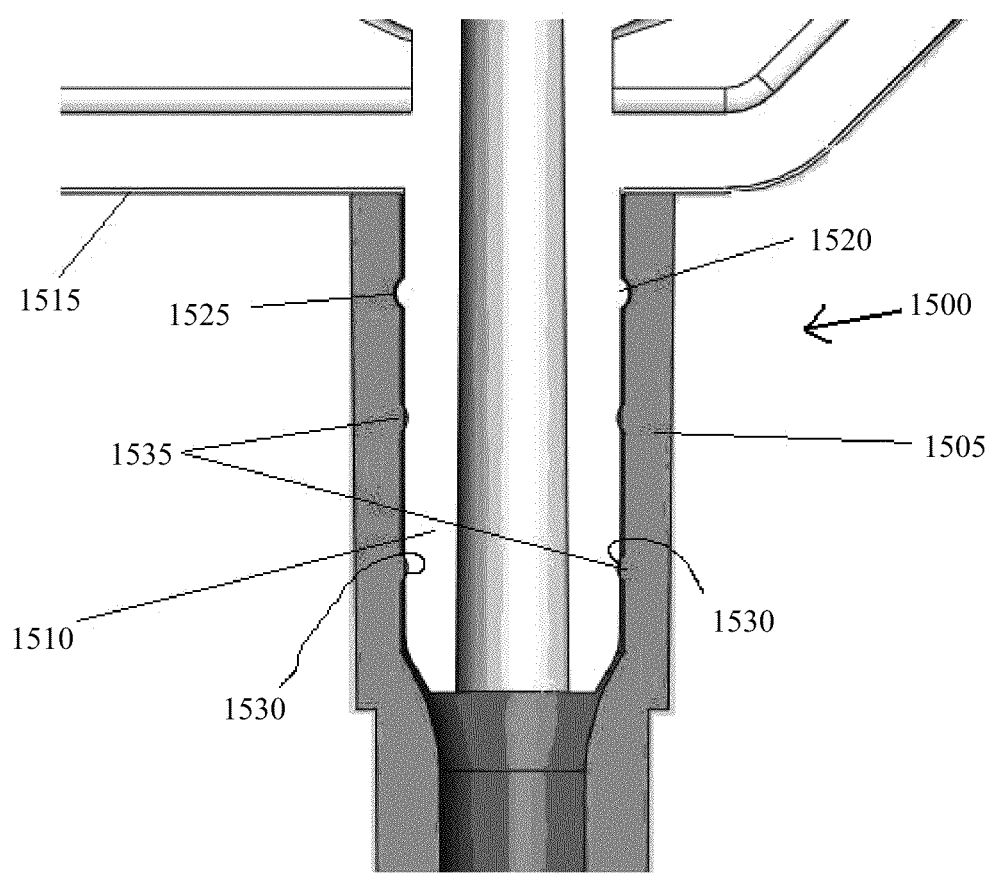
FIG. 15 shows a detail view of an embodiment of the connection between a process fluid connector and an aspiration/expiration tube.

FIG. 15 shows a detail view of an embodiment of the connection 1500 between an aspiration/expiration tube 1505 and a process fluid connector 1510 on a bioprocessing cartridge 1515. As shown, process fluid connector 1510 may be provided with one or more retention rings 1520 which may provide a clearance fit with a corresponding retention groove 1525 on the inner wall of the aspiration/expiration tube 1505. Process fluid connector 1510 includes one or more sealing grooves 1530, which may provide an interference fit with sealing rings 1535 on the inner wall of aspiration/expiration tube 1505. In this manner, retention rings 1520 may secure the aspiration/expiration tube 1505 to the process fluid connector 1510, while the sealing rings 1535 may provide for sealing of the aspiration/expiration tube 1505 to the process fluid connector 1510. It should be understood that many alternative connections may be used to provide aspiration/expiration tubes connected to the cartridges and that the tubes may also be formed integrally with the cartridges.

Figure 16A:
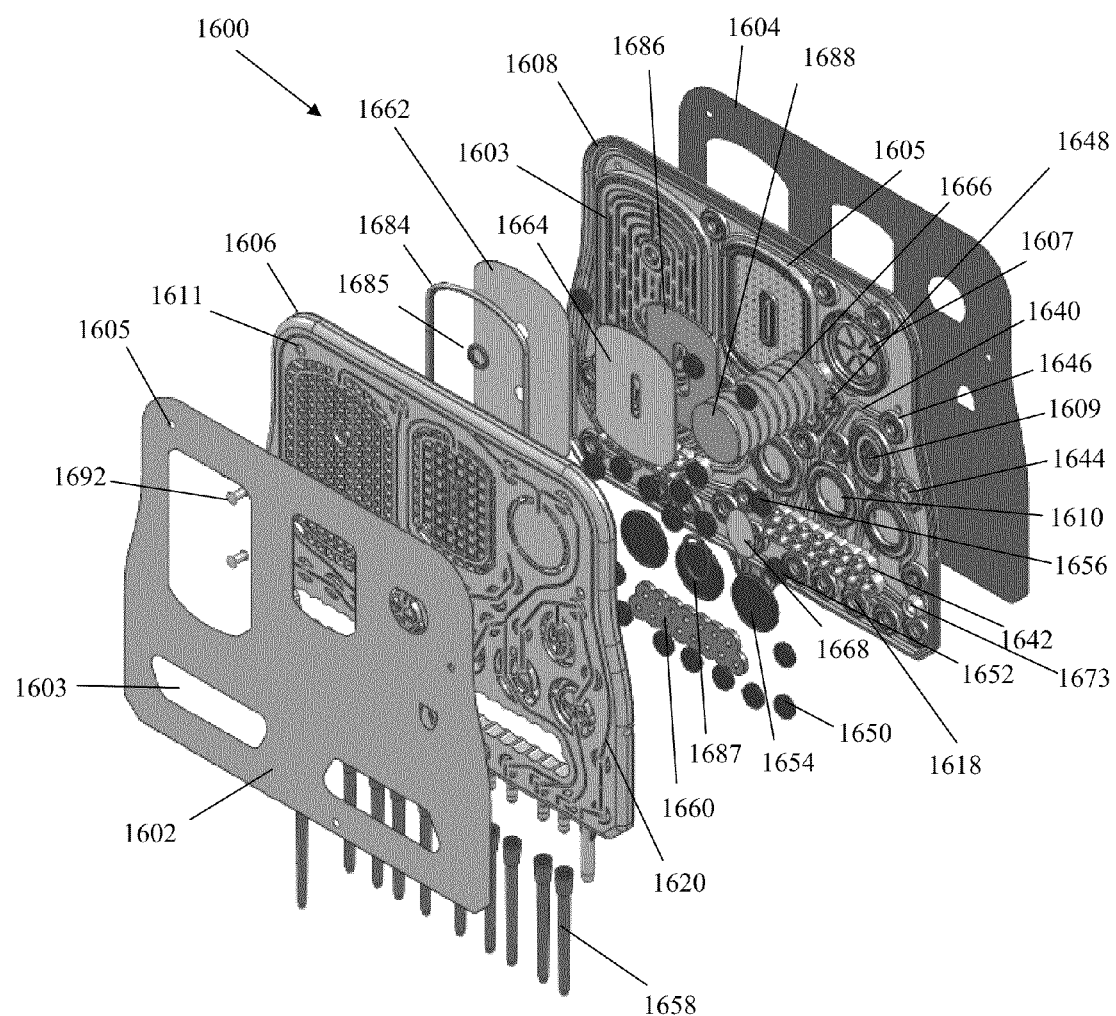
FIG. 16A an exploded view of an embodiment of a bioprocessing cartridge.

FIG. 16A shows an exploded view of an embodiment of a bioprocessing cartridge 1600. Cartridge 1600 has two film or foil layers 1602 and 1604 which may be sealed, such as heat sealed or adhesive sealed onto the exterior face of the process fluid layer 1606 and the exterior face of the control or pneumatic layer 1608 of the cartridge 1600. The film layers 1602, 1604 may include any suitable plastic film, such as coated plastic films, or suitable metallic film, such as metallic foils or coated metallic foils, including aluminum foils, and the films may be coated with any appropriate coating and/or adhesives, such as heat seal adhesive. In some embodiments, the film may be a PET film with a PE tie layer that is coated with a heat seal adhesive on the face that is in contact with the process fluid layer 1606 or pneumatic layer 1608. In other embodiments, the film layers may comprise aluminum foil that is coated with a heat seal adhesive on the face that is in contact with the process fluid layer 1606 or pneumatic layer 1608. The film layers may include penetrations 1603 for the control fluid connectors 1642, penetrations 1605 for alignment guides 1611 and, in some embodiments, a penetration to provide viewing access to a color indicator chamber, if present. When sealed onto the relevant surface of the cartridge 1600, the film layers 1602 and 1604 may form the final wall for the process fluid channels 1620 on fluid layer 1606 and the pneumatic channels 1640 on pneumatic layer 1608.

The cartridge 1600 may include a process fluid layer 1606 having multiple process fluid channels 1620. Process fluid channels 1620 may span the entire process fluid layer 1606 or alternatively, may be open on the front or exterior surface of the layer and not open on the back or interior surface of the layer. In this manner, process fluid channels 1620 may be isolated from the control fluid layer 1608, except where layer pass-throughs or pass-through valves are provided and when applied to the process fluid layer 1606, film layer 1602 may complete the walls of the process fluid channels 1620.

Cartridge 1600 may also include pneumatic layer 1608 having pneumatic channels 1640 and pneumatic connectors 1642. Pneumatic channels 1640 may span the entire pneumatic layer 1608 or, alternatively, may instead be open on the back or exterior surface of the layer and not open on the front or interior surface of the layer. In this manner, pneumatic channels 1640 may be isolated from the process fluid layer 1606, except where layer pass-throughs or pass-through valves are provided and when applied to the pneumatic layer 1608, film layer 1604 may complete the walls of the pneumatic channels 1640.

As shown, each of the pneumatic or control layer 1608 and the process fluid layer 1606 includes bioprocessing chamber compartments 1603, 1605, 1607 and 1609, pump compartments 1610 and valves 1654, and access valve compartments 1618 and valves 1650, process valve compartments 1644 and valves 1652, and in some embodiments, check valve compartments 1646 and valves 1656. In some embodiments, the cartridge 1600 may include pass-through penetrations 1673. The control layer 1608 may also includes control fluid connectors 1642, which may include with gaskets.

In some embodiments, a bioprocessing chamber may include a filter 1662, 1664, 1666, and 1668, O-rings 1684, and gaskets 1685, 1687 as is shown in the exploded view of bioprocessing cartridge 1600. In some embodiments, the filter may be a B1a065 membrane, nitrocellulose membrane, glass fiber membrane, Xthick membrane, PPTR membrane, Anion Exchange membrane or any other suitable filter. In some embodiments, the filter of a bioprocessing chamber may be supported by a solid support or frit 1686, 1688. The filter may be a single layer filter or a multiple layer filter, and may be supported by one or more than one solid support, for example as is shown in bioprocessing chamber 1607. The two layers of the cartridge and the components found in between may be sealably joined, such as by ultrasonic or other welding or using an adhesive, latches, clasps, or any other mechanism for joining the two plastic layers to form an embodiment of a bioprocessing cartridge. In some embodiments one or more of the bioprocessing compartments includes one or more O-rings and/or tongue and groove components to assist with sealing. In addition, in some embodiments one or more of the bioprocessing chamber compartments on one or both of control layer 1608 and the process fluid layer 1606 includes structures, such as protrusions, along or on one or both of their interior walls to prevent or limit interaction of the filter or solid support with the walls of the bioprocessing chambers. In some embodiments, rivets 1692 may be used to further support the membrane and to seal a bioprocessing chamber.

Figure 16B:
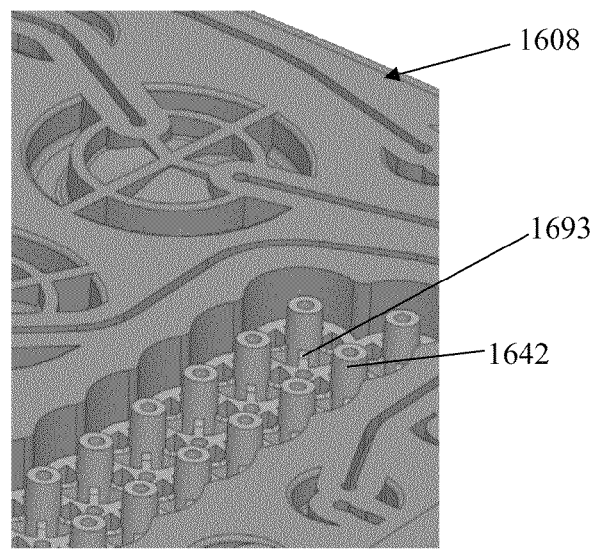
FIGS. 16B-16D show close-up views of portions of the bioprocessing cartridge shown in FIG. 16A.
Figure 16C:
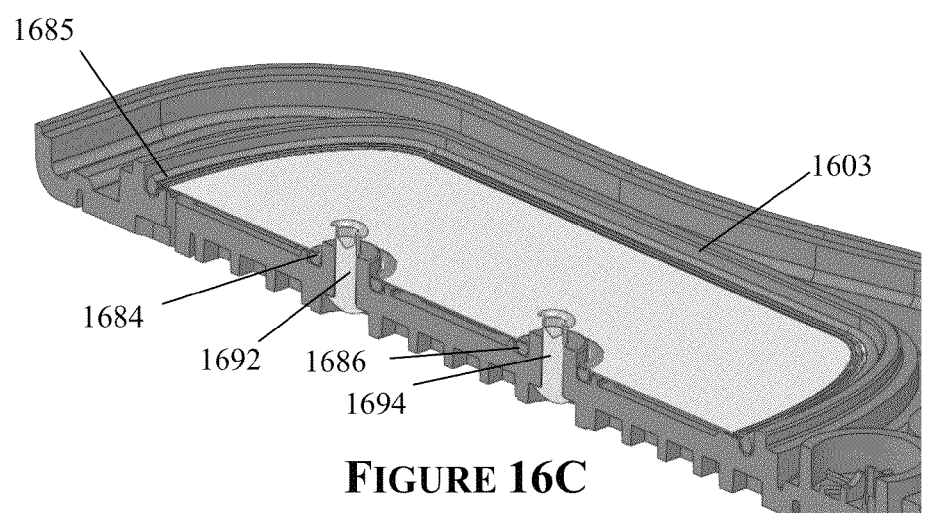
Figure 16D:
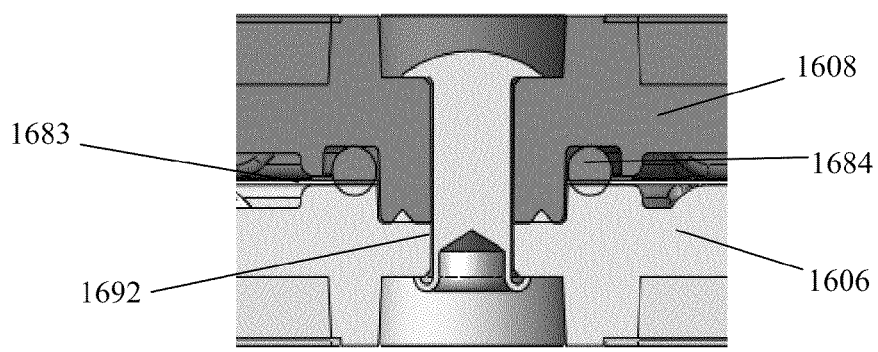

FIG. 16B is a close up view of control fluid connectors 1642 located on the pneumatic layer 1608. In some embodiments, the control fluid connectors 1642 further include supports 1693 which provide additional support to the control fluid connectors during attachment of supply tubes to the card. FIG. 16C is a lateral cross-sectional view of one half of bioprocessing chamber 1603 showing a gasket 1685, O-rings 1684, 1686 and rivets 1692, 1694. FIG. 16D shows a side view of the pneumatic layer 1608 and the fluid layer 1606, the filter 1683, O-ring 1684, and a rivet 1692 creating additional support and/or connecting the pneumatic layer 1608 and the fluid layer 1606 together.

Figure 17A:
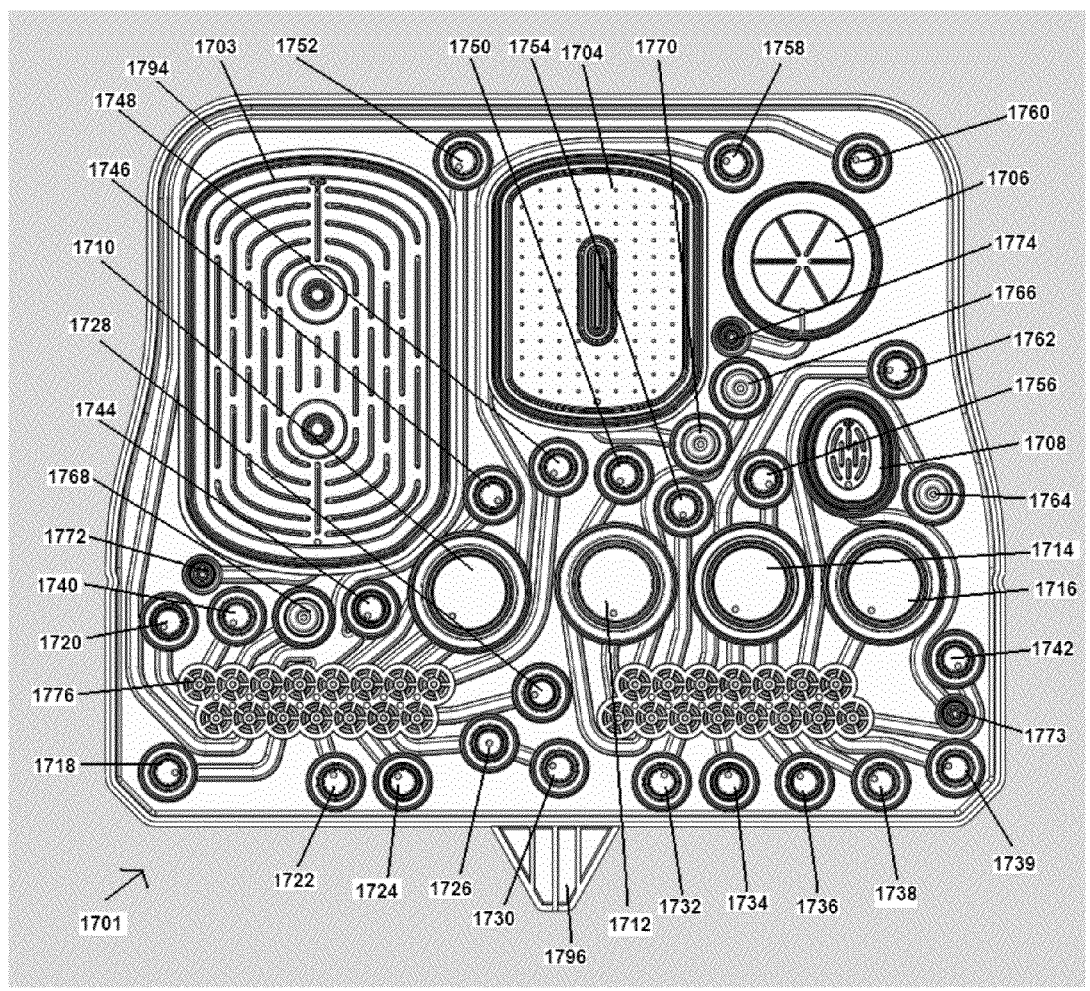
FIGS. 17A & 17B show front and rear layer views of an embodiment of a bioprocessing cartridge.
Figure 17B:
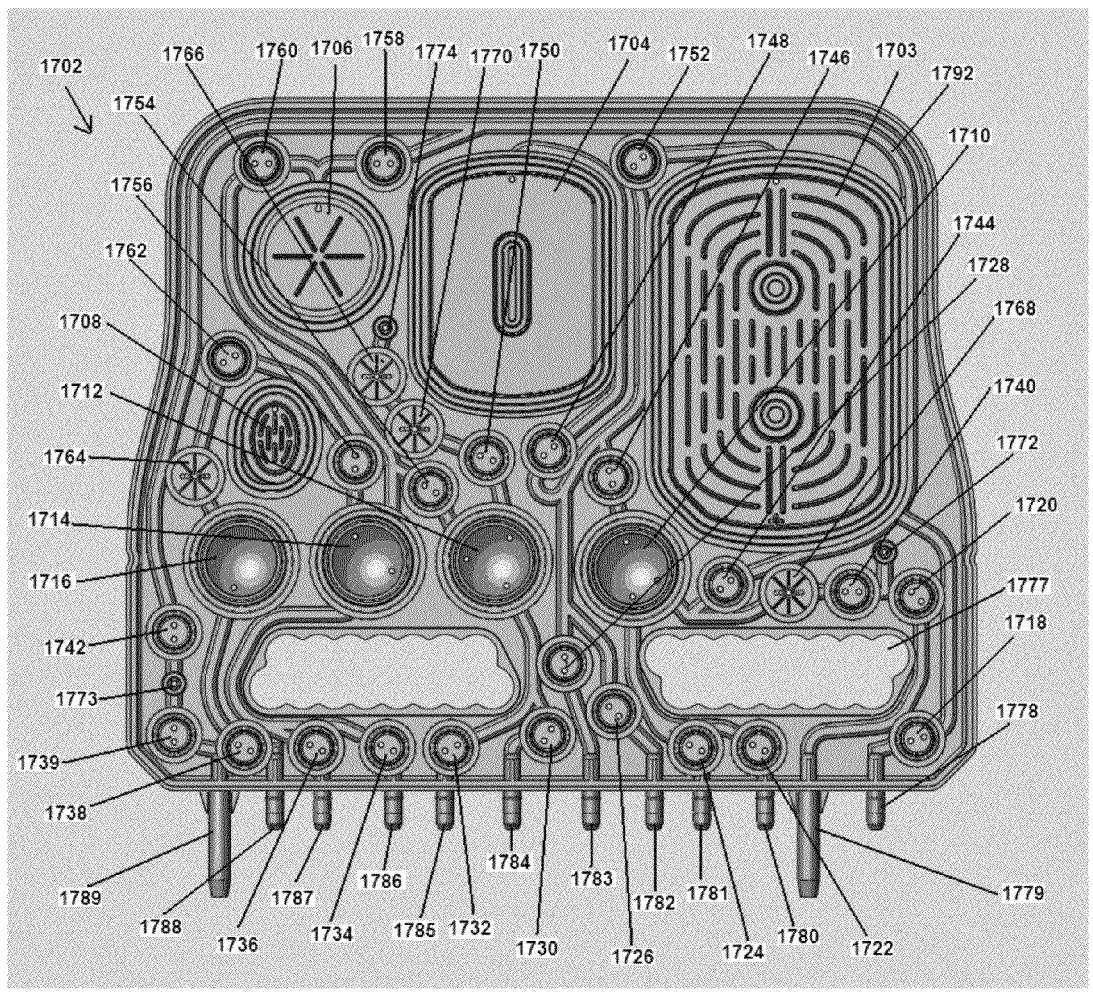

FIGS. 17A and 17B show views of the interior sides of a control layer 1701 and a process fluid layer 1702 of an embodiment of a bioprocessing cartridge 1700. As shown, each of the control layer 1701 of FIG. 17A and the process fluid layer 1702 of FIG. 17B includes bioprocessing chamber compartments 1703, 1704, 1706 and 1708, pump compartments 1710, 1712, 1714 and 1716, access valve compartments 1718, 1720, 1722, 1724, 1726, 1728, 1730, 1732, 1734, 1736, 1738, and 1739, process valve compartments 1740, 1742, 1744, 1746, 1748, 1750, 1752, 1754, 1756, 1758, 1760 and 1762, check valve compartments 1764, 1766, 1768, pass-through check valve compartments 1770 and pass-throughs penetrations 1772, 1773, and 1774. The control layer 1701 may also include control fluid connectors 1776, control fluid channels 1794 and slot alignment guide 1796. The process fluid layer 1702 also includes control fluid connector penetrations 1777, process fluid connectors 1778, 1779, 1780, 1781, 1782, 1783, 1784, 1785, 1786, 1787, 1788 and 1789 and process fluid channels 1792.

The control layer 1701 and/or process fluid layer 1702 may have pump membranes, valve membranes, O-rings, and solid supports placed within the relevant compartments and then the two layers may be sealably joined, such as by ultrasonic or other welding or using an adhesive, latches, clasps, clamps, or any other mechanism for joining the two plastic layers to form an embodiment of a bioprocessing cartridge. In some embodiments one or more of the bioprocessing compartments includes one or more O-rings and/or tongue and groove components to assist with sealing. In some embodiments, each of bioprocessing chamber compartments 1703, 1704, and 1708 include O-rings. In addition, in some embodiments one or more of the bioprocessing chamber compartments on one or both of control layer 1701 and the process fluid layer 1702 includes structures, such as protrusions, along or on one or both of their interior walls to prevent or limit interaction of the filter or solid support with the walls of the bioprocessing chambers.

Figure 18A:
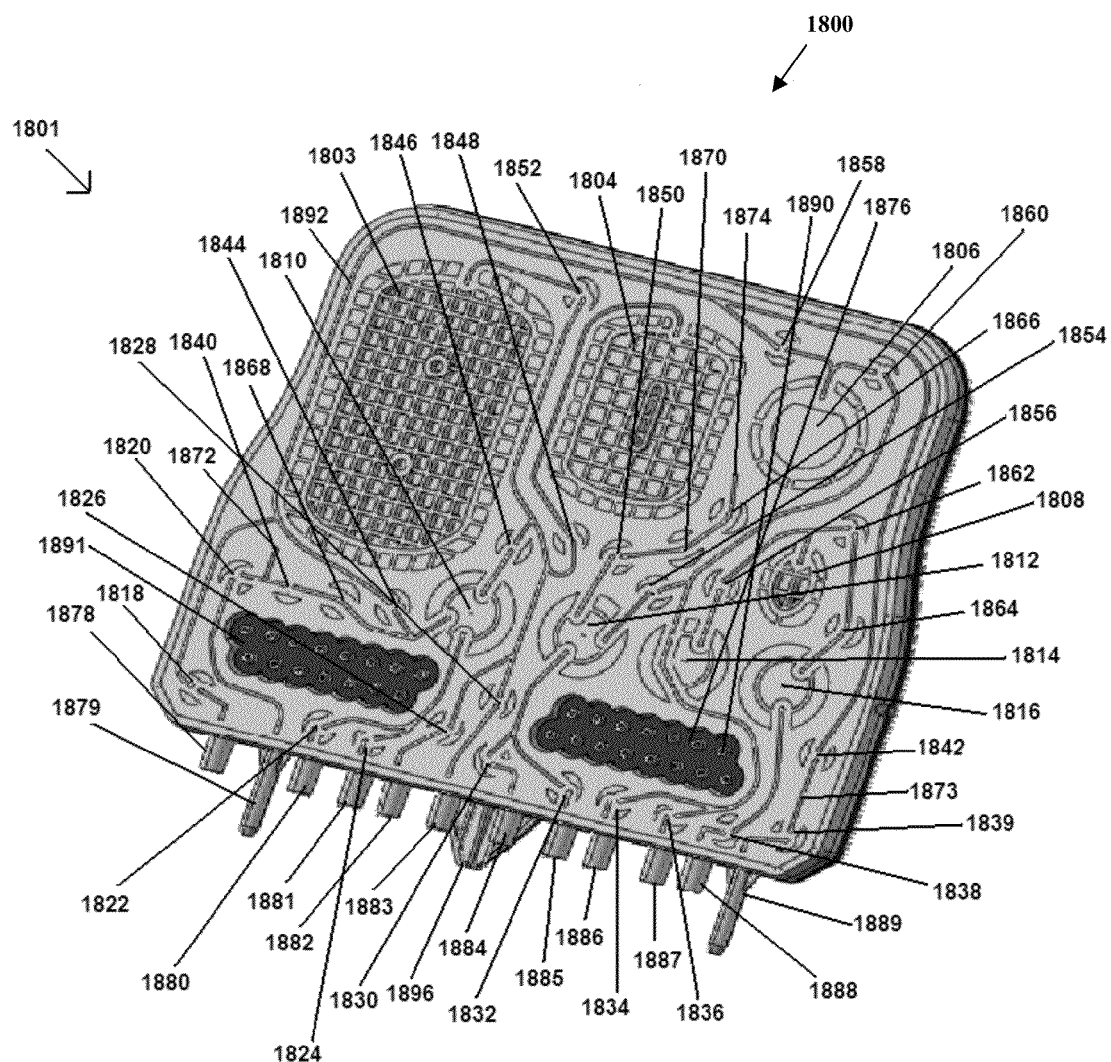
FIGS. 18A & 18B show front and rear views of an embodiment of a bioprocessing cartridge.
Figure 18B:
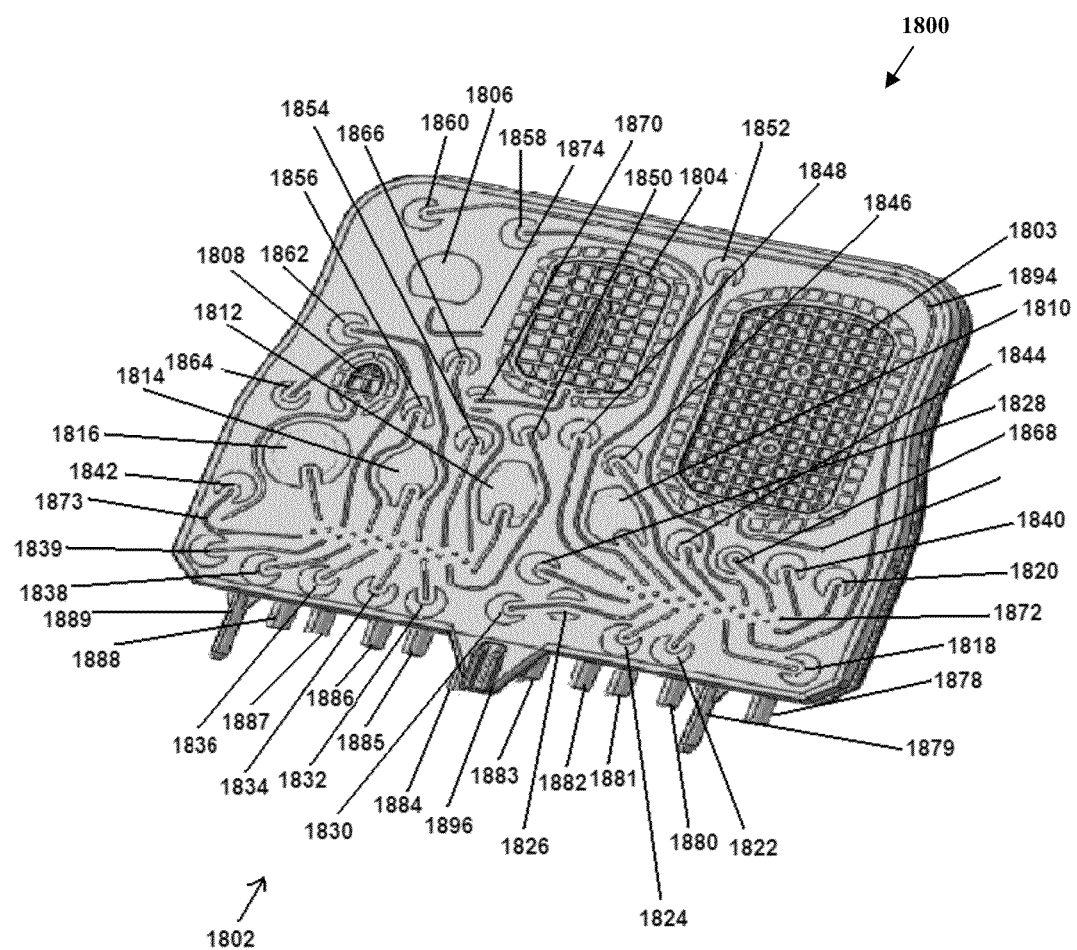

FIGS. 18A and 18B show front and rear views 1801 and 1802 respectively of an embodiment of an assembled bioprocessing cartridge. As shown, the bioprocessing cartridge includes bioprocessing chambers 1803, 1804, 1806 and 1808, pumps 1810, 1812, 1814 and 1816, access valves 1818, 1820, 1822, 1824, 1826, 1828, 1830, 1832, 1834, 1836, 1838, and 1839, process valves 1840, 1842, 1844, 1846, 1848, 1850, 1852, 1854, 1856, 1858, 1860 and 1862, check valves 1864, 1866, 1868, pass-through check valve 1870, pass-throughs 1872, 1873 and 1874, control fluid connectors 1876, process fluid connectors 1878, 1879, 1880, 1881, 1882, 1883, 1884, 1885, 1886, 1887, 1888 and 1889, control fluid gaskets 1890 and 1891, process fluid channels 1892, control fluid channels 1894 and slot alignment guide 1896.

Each of bioprocessing chambers 1803, 1804, 1806 and 1808 may include a solid support. In some embodiments, where the bioprocessing cartridge is used for purification and collection of nucleic acids, such as DNA including plasmids or plasmid DNA from whole cells, bioprocessing chamber 1803 may include a cell separation filter for separating the whole cells from the cell culture media, bioprocessing chamber 1804 may include a cell lysate clarification filter for clarifying the lysate by filtering out cellular and other debris within the lysate, bioprocessing chamber 1806 may include a solid phase extraction disk, cassette or filter to reversibly bind the nucleic acids from the cellular lysate, and bioprocessing chamber 1808 may include a precipitation filter to capture the DNA eluted from the solid phase extraction disk, cassette or filter. In some embodiments one or more of the bioprocessing chambers includes one or more O-rings and or tongue and groove seals. In some embodiments, each of bioprocessing chambers 1803, 1804 and 1808 may include O-rings or gaskets. In addition, in some embodiments one or more of the bioprocessing chambers includes structures, such as protrusions, along or on one or both of their interior walls to prevent or limit interaction of the filter or solid support with the walls of the bioprocessing chambers.

Each of access valves 1818-1839, process valves 1840-1862 and check valves 1864-1868 may have pinched membranes inside joined compartments as described elsewhere herein relative to other bioprocessing cartridges, the process fluid channels 1892 and control fluid channels 1894 may be fluid channels as described elsewhere herein with respect to such channels and the process fluid connectors 1878-1889 may be process fluid connectors as described elsewhere herein. Control fluid connectors 1876 may be as described elsewhere herein, with the exception that, in some embodiments, a single control fluid gasket 1890 and/or 1891 is provided over a plurality of control fluid connectors and the control fluid gaskets 1890 and 1891 may be provided externally to the bioprocessing cartridge rather than internally. Pass-through check valve 1870 may provide for actively controlled fluid flow between a process fluid layer and a control fluid layer on bioprocessing cartridge 1800, by allowing for flow in only one direction between the layers. In some embodiments, pass-through check valve 1870 may provide for flow from the process fluid layer to the control fluid layer, while in other embodiments, pass-through check valve 1870 may provide for flow from the control fluid layer to the process fluid layer of bioprocessing cartridge 1800. The pass-throughs may provide for fluid communication between a process fluid layer and a control fluid layer on bioprocessing cartridge 1800 in both directions.

The process fluid layers and control fluid layers and the aspiration/expiration tubes of the bioprocessing cartridges may be made from any suitable material, such as plastic, such as ABS, polystyrene, polypropylene, polycarbonate and the like and may be injection molded or otherwise formed such as by etching. In some embodiments, the bioprocessing cartridges may be injection molded and may have mesoscale fluid channels. In other embodiments, the bioprocessing cartridges may have microscale channels. The valve and pump membranes may be made from the same or different materials and may be made from any material flexible enough to withstand the application of the pressure and vacuum during the bioprocessing. Examples of some suitable materials include thermoplastics and thermoplastic elastomers, such as SANTOPRENE™, and silicone. In addition, the membranes may be made from traditionally rigid materials when the membranes are suitably thin to be flexible, despite the relative general rigidity of the material.

In some embodiments, one or more of the interior surfaces of the bioprocessing chamber may include projections or may be frosted or otherwise surface modified to limit or prevent undesirable interaction between a solid support within the chamber and one or more of the interior surfaces. In addition, when assembling the cartridges, additional sealing surfaces or components may be provided either on the layers or between the layers to assist in sealing individual portions of the cartridges or the periphery of the cartridges. For example, in some embodiments, the bioprocessing cartridges may include one or more O-ring seals and/or tongue in groove or other sealing mechanisms may be included in the layers around all or a portion of the periphery of the cartridge, of one or more bioprocessing chambers or of one or more valves or pumps. Additional sealing of the layers of the cartridges may be accomplished by sealing the layers together with an adhesive, or by using ultrasonic or solvent welds or other suitable mechanism for sealing the layers together. In addition, though the bioprocessing cartridges described herein have been described as having two layers, it should be understood that the bioprocessing cartridges may have any suitable number of layers depending on the bioprocessing protocol used. For example, bioprocessing cartridges may include multiple process fluid layers, multiple control fluid layers, or temperature control layers through which the temperature of a portion of or through which all of the cartridge is controlled. Moreover, instead of providing individual membranes for the pumps and valves, in some embodiments a single membrane layer may be provided that extends across each of the various compartments, thereby providing individual membranes for the compartments as a single layer in the cartridges.

Figure 19A:
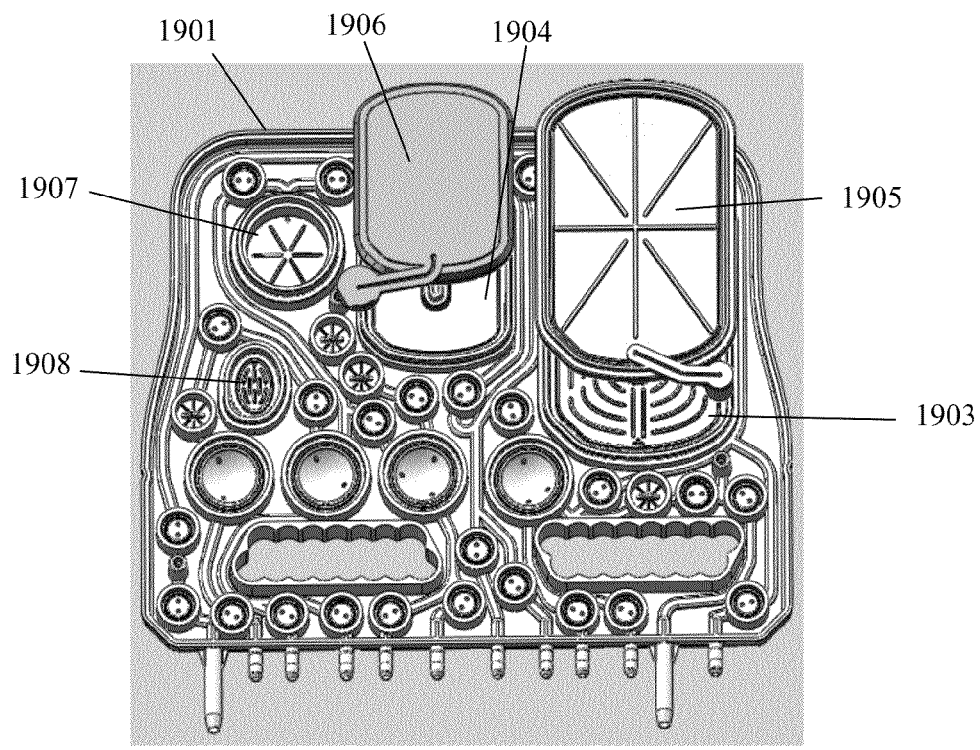
FIGS. 19A & 19B show a interior and exterior views, respectively, of an embodiment of a bioprocessing cartridge.
Figure 19B:
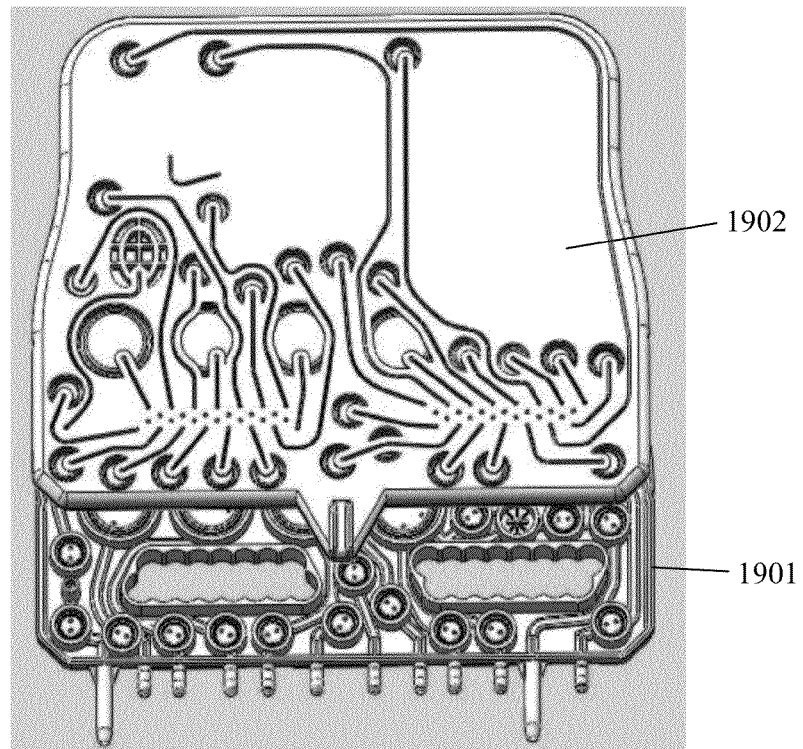

FIGS. 19A and 19B show alternate embodiments of a bioprocessing cartridge. In some embodiments, the bioprocessing cartridge may include at least one bioprocessing chambers which may include filter covers for the bioprocessing chamber. For example purposes only, as shown in FIG. 19A, at least some of the bioprocessing chambers, 1903 and 1904, may further include filter covers 1905, 1906, respectively. In some embodiments, all the bioprocessing chambers 1903, 1904, 1907, 1908 may include filter covers. In some embodiments, at least one, or at least two, at least three, or more than three bioprocessing chambers include filter covers. A filter or membrane may be positioned in the fluidic side 1901 of the bioprocessing cartridge, as shown in FIG. 19A and may serve to seal the bioprocessing chamber. In some embodiments, the filter may be positioned on the pneumatic side of the card and the filter covers positioned over the individual bioprocessing chambers. The pneumatic side 1901 and the fluidic side 1902, may then be aligned and assembled together, as shown in FIG. 19B. The fluidic side 1902 and the pneumatic side 1901 may then be assembled together by any suitable mechanism.

Figure 20A:
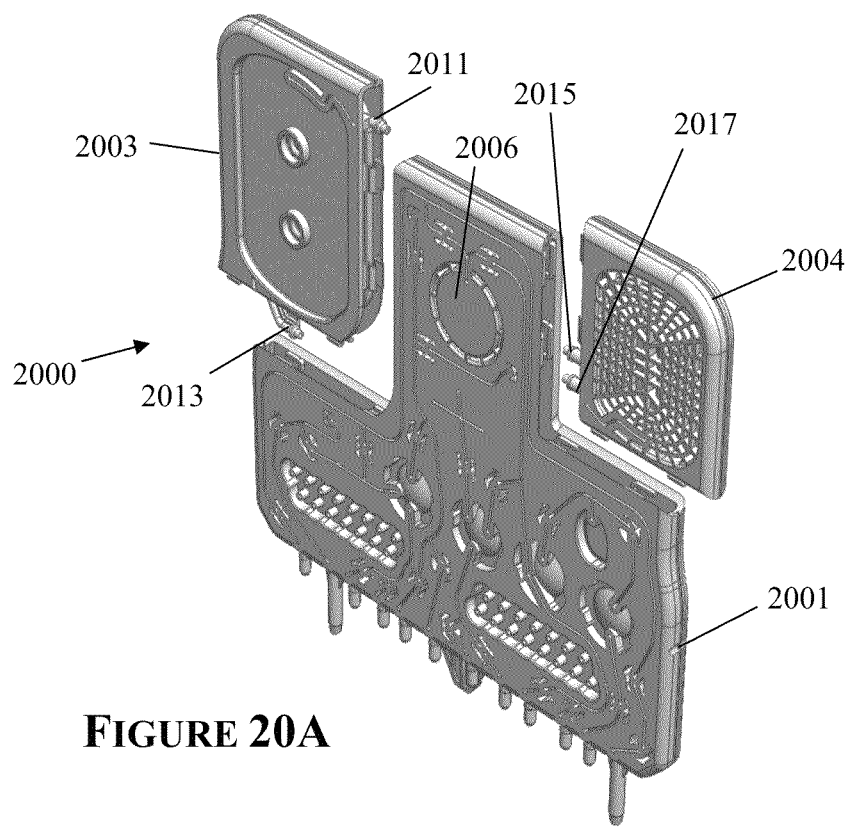
FIGS. 20A & 20B show an alternate embodiment of a bioprocessing cartridge.
Figure 20B:
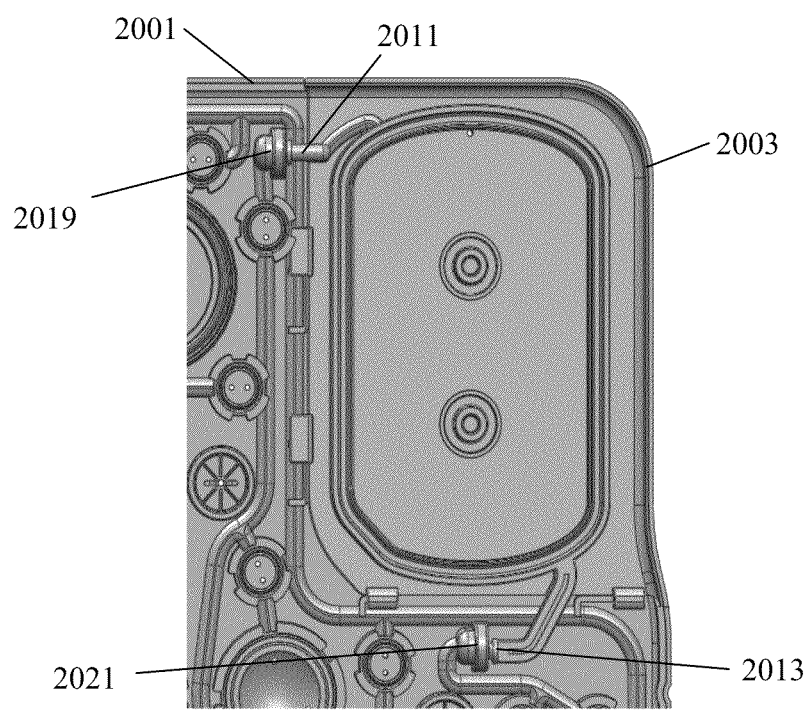

In some embodiments, at least one of the bioprocessing chambers may be modular as shown in FIGS. 20A & 20B. FIG. 20A shows a bioprocessing cartridge 2000 in which two bioprocessing chambers 2003 and 2004 may be attached to the body 2001 of the cartridge 2000. In some embodiments of the bioprocessing cartridge, at least one bioprocessing chamber is modular and may be attached to the bioprocessing cartridge. FIG. 20A shows a bioprocessing cartridge 2000 with a modular bioprocessing chamber 2003 including a cell separation filter and a modular bioprocessing chamber 2004 including a cell lysate clarification filter. In some embodiments, the bioprocessing chambers 2003, 20204 may be located on opposite sides of the bioprocessing cartridge 2000, such as for example purposes, on opposite sides of the solid phase extraction disk 2006, as shown in FIG. 20A. In some embodiments, the modular bioprocessing chambers 2003, 2004 may be connected to bioprocessing cartridge 2000 such that the two modular bioprocessing chambers 2003, 2004 are connected to each other in series, so that a first modular bioprocessing chamber is attached to the body of the cartridge and then a second modular bioprocessing chamber is attached to the first modular bioprocessing chamber. In some embodiments, at least one, at least two, at least three, or more than three of the components of the cartridge may be modular. The modular components may include connectors 2011, 2013, 2015, and 2117, for example, the male end connectors as shown in FIG. 20A that interface with connectors located on the body 2001 of the cartridge. FIG. 20B shows a close up view of one bioprocessing chamber 2003 connected to the bioprocessing card. FIG. 20B shows a bioprocessing chamber 2003 connected to the body 2001 of the cartridge. As shown in FIG. 20B, in some embodiments, the bioprocessing chamber 2003 may include male connectors 2011, 2013 of the modular bioprocessing chamber 2003 which interact with female connectors 2019, 2021 located on the body 2001 of the bioprocessing cartridge. In some embodiments, the male connectors are located on the body of the bioprocessing cartridge and the female connectors are located on bioprocessing chamber module.

Figure 21A:
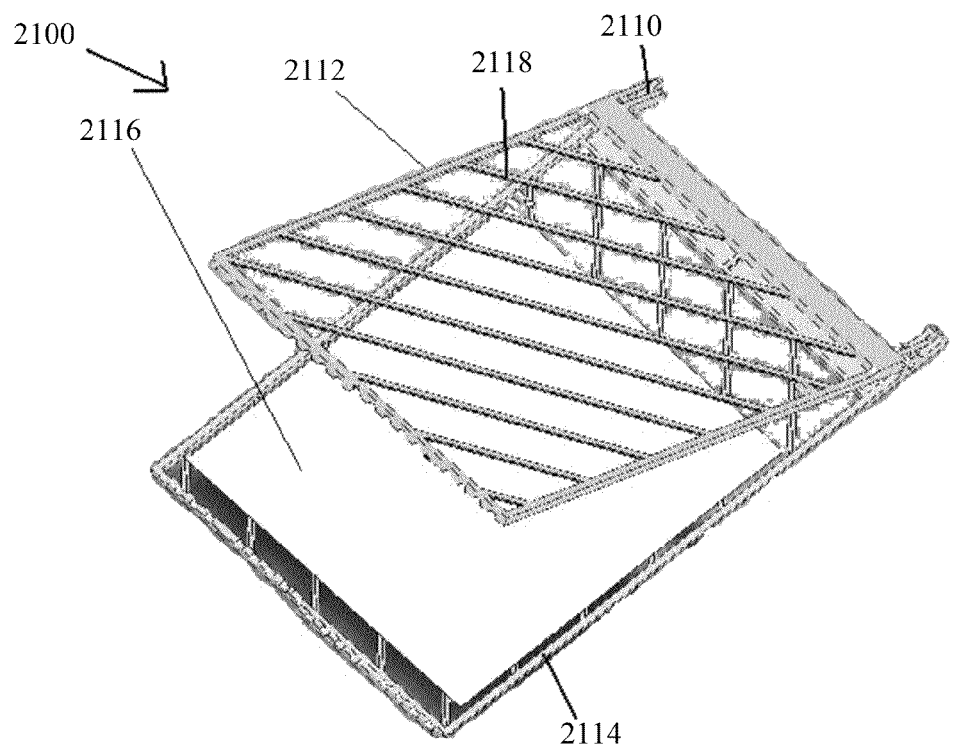
FIGS. 21A and 21B show detail views of blot membrane holders that may be inserted into embodiments of the bioprocessing cartridges.
Figure 21B:
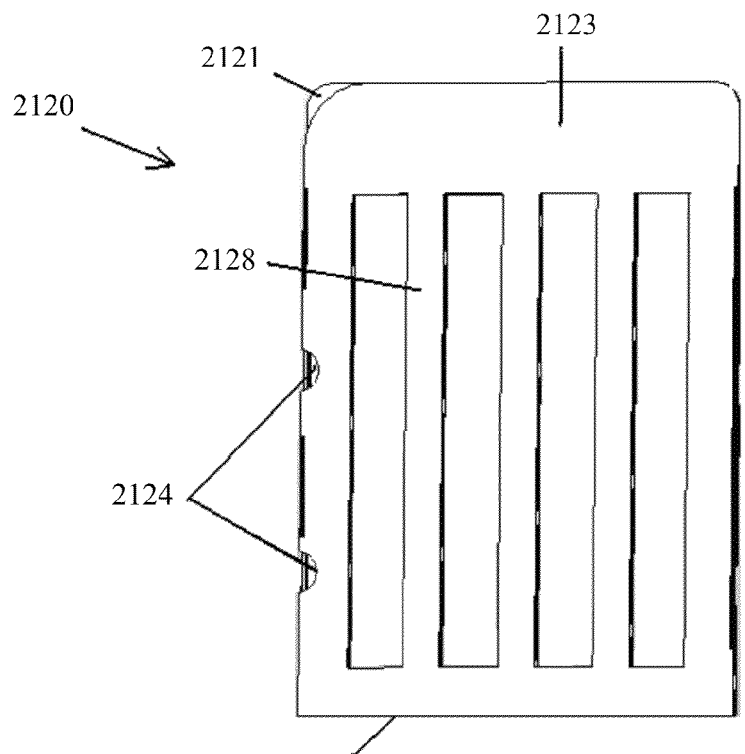

FIGS. 21A and 21B show detail views of membrane holders, such as blot membrane holders, that may be inserted into some embodiments of the bioprocessing cartridges. As shown in FIG. 21A, membrane holder 2100 may comprise a hinge 2110 connecting the halves 2112 and 2114 of the membrane holder 2100, allowing the halves 2112 and 2114 to be opened or closed so that a membrane 2116 may be inserted into the holder. The halves 2112 and 2114 may include ribs, for example, diagonal ribs 2118 to support the structure of the holder while allowing for free flow of process fluids around both sides of the membrane 2116 and preventing or limiting interaction between the membrane 2116 and the walls of a bioprocessing chamber on a bioprocessing cartridge. FIG. 21B shows an alternative membrane holder 2120. In some embodiments instead of a hinge the holder may be folded along fold 2122 to form the two portions 2121 and 2123 of the holder. Membrane holder 2120 includes fluid flow cutouts 2124 to provide non-interfering access to a membrane in the holder 2120 from flow channels on a bioprocessing cartridge. Membrane holder 2120 may include support ribs 2128, oriented for example in a vertical orientation to provide support to the holder while allowing for free flow of process fluids around both sides of the membrane and while limiting or preventing interaction between the walls of a bioprocessing chamber with a membrane within the holder 2120. The membrane holders may be constructed from any suitable materials including plastics, such as for example PVC, HDPE, polyesters, and APET, and may be injection molded or be assembled from injection molded pieces or may be die cut. In some embodiments, the membrane holders help provide for laminar flow of process fluids across both sides of a membrane in a bioprocessing chamber and prevent the membrane from sticking or contacting one or more walls of the bioprocessing chamber.

Figure 22A:
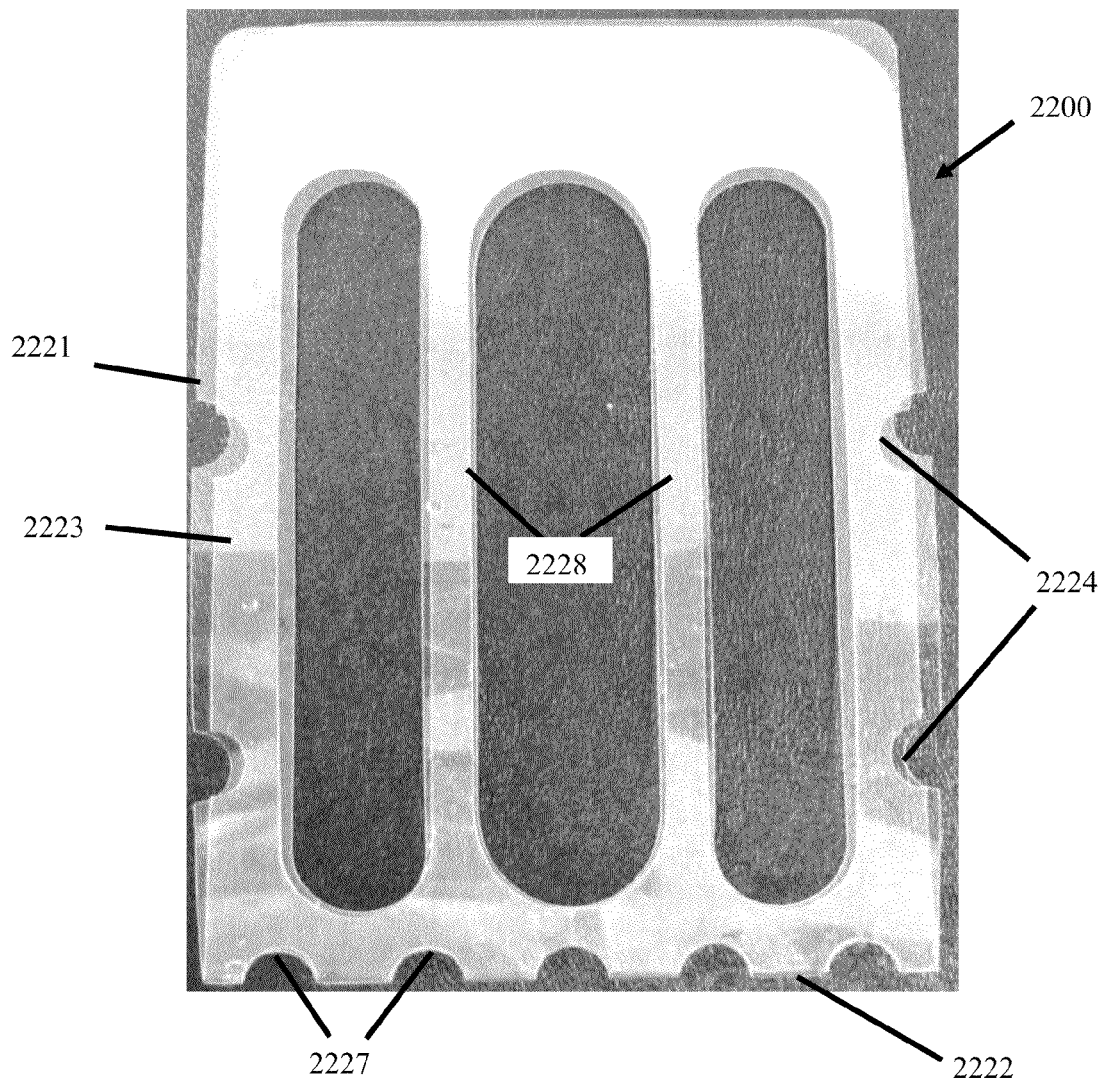
FIGS. 22A and 22B show alternative embodiments of blot membrane holders.

FIG. 22A shows an alternative embodiment of a blot membrane holder 2200 that is similar to the blot membrane holder 2120 shown in FIG. 21B. Blot membrane holder 2200 is folded similar to the blot membrane holder 2120 in that holder 2200 is folded along fold 2222 to form two portions, portion 2221 and portion 2223, of holder 2200 between which a blot membrane may be placed. Unlike holder 2120, holder 2200 includes bottom fluid flow cutouts 2227 along fold 2222 to facilitate fluid flow around a blot membrane in the holder 2200 and between the bioprocessing chamber and the fluid flow channels on a bioprocessing cartridge in addition to the side fluid flow cutouts 2224. Similar to blot membrane holder 2120, holder 2200 includes support ribs 2228 shown in a vertical orientation in the figure to provide support to the holder while allowing for free flow of process fluids around both sides of the membrane and while limiting or preventing interaction between the walls of a bioprocessing chamber with a membrane within the holder 2200. Blot membrane holder 2200 may be constructed from the same or similar materials from which the other blot membrane holders described herein are constructed.

Figure 22B:
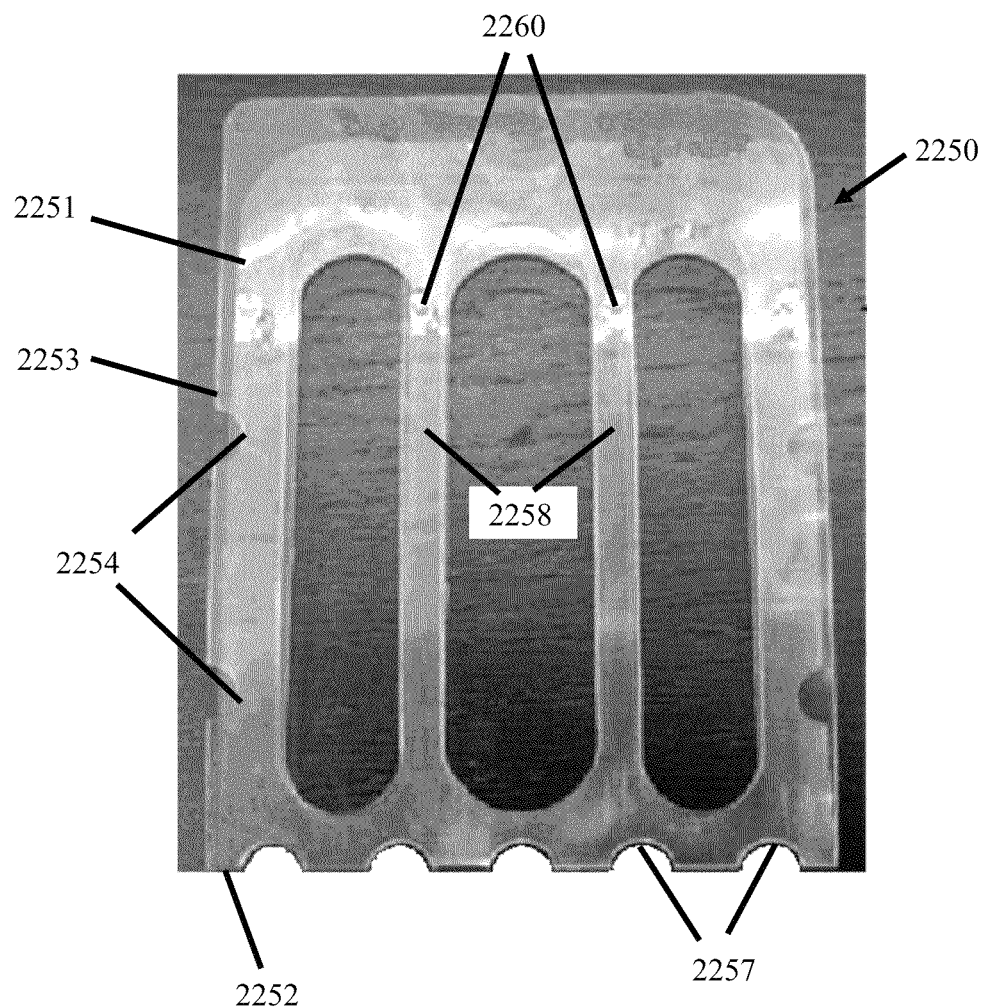

FIG. 22B shows an alternative embodiment of a blot membrane holder 2250 that is similar to the blot membrane holder 2200 shown in FIG. 22A. Blot membrane holder 2250 is folded similar to the blot membrane holder 2200 in that holder 2250 is folded along fold 2252 to form two portions, a first portion 2251 and a second portion 2253, of holder 2250 between which a blot membrane may be placed. In addition, like holder 2200, holder 2250 includes bottom fluid flow cutouts 2257 along fold 2252 to facilitate fluid flow around a blot membrane in the holder 2250 and between the bioprocessing chamber and the fluid flow channels on a bioprocessing cartridge in addition to the side fluid flow cutouts 2254. Unlike holder 2200, blot membrane holder 2250 includes side fluid flow cutouts only on portion 2251 and not on portion 2253 and blot membrane holder 2250 also includes bumps or nibs 2260 that facilitate separation of the two portions 2251 and 2253 and provide a more consistent area for processing a blot membrane. Similar to blot membrane holder 2200, holder 2250 includes support ribs 2258 shown in a vertical orientation in the figure to provide support to the holder while allowing for free flow of process fluids around both sides of the membrane and while limiting or preventing interaction between the walls of a bioprocessing chamber with a membrane within the holder 2250. Blot membrane holder 2250 may be constructed from the same or similar materials from which the other blot membrane holders described herein are constructed.

Figure 23:
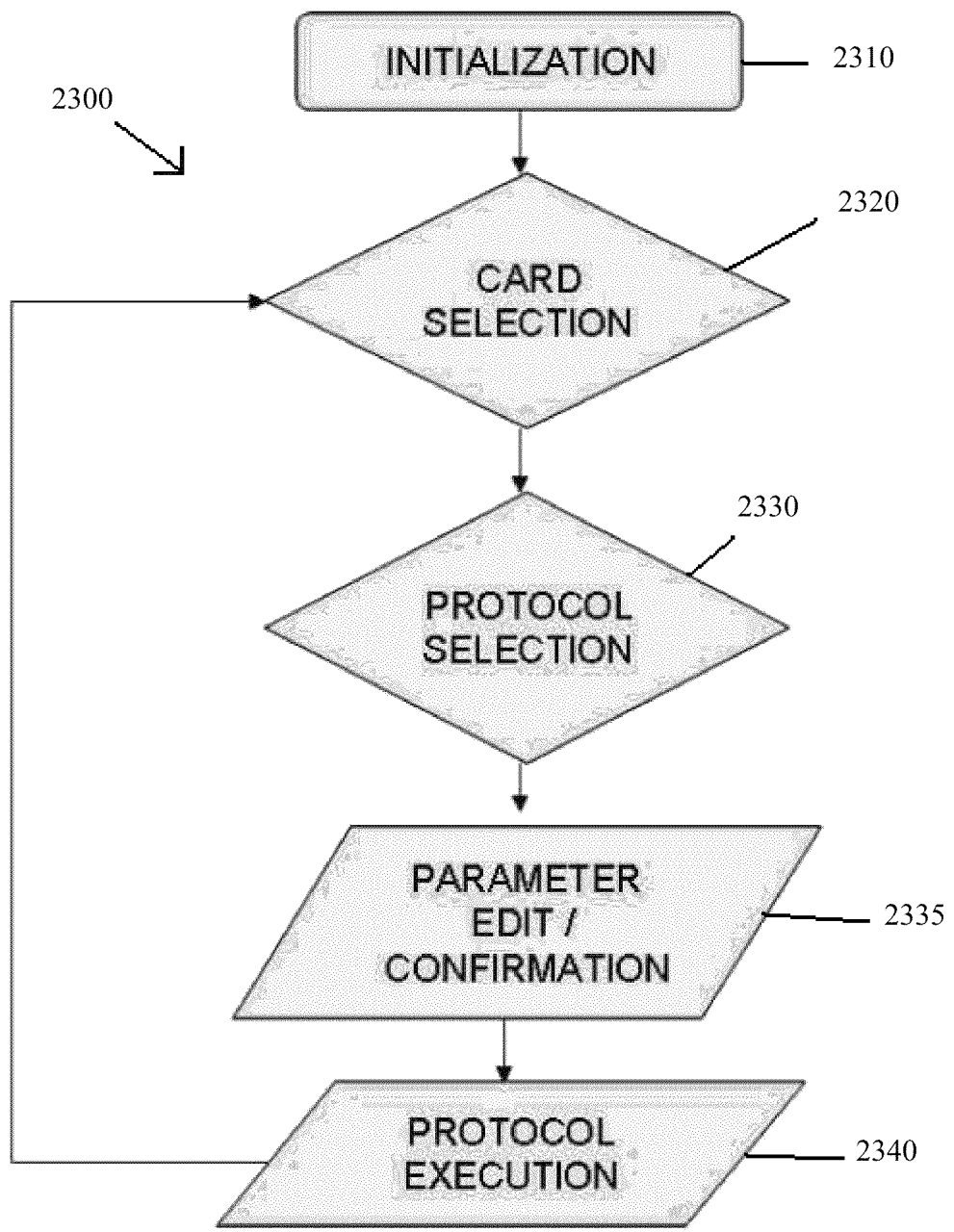
FIG. 23 shows a high level flow chart of the basic user interface for operation of an embodiment of a bioprocessing device.

FIG. 23 shows a basic flowchart 2300 of one embodiment of a method for performing some of the steps that may be included in performing bioprocessing protocols using the automated control system on some embodiments of the bioprocessing device provided herein. These steps are intended to be by way of example only, and some embodiments may include additional steps, different orders of steps and may omit some of the steps shown. As shown, the device may be initialized 2310, the type and/or number of cartridges inserted into the cartridge slots of the device may be identified 2320 and a bioprocessing protocol may be selected 2330 either from an available set of pre-loaded protocols or may be user generated on the device either by editing a pre-existing protocol or by entering a new protocol onto the device or by uploading a protocol onto the device. After selection of the protocol 2330, the device may prompt the user to confirm acceptance and correctness of the individual parameters associated with a protocol 2335 and then the protocol may be executed 2340 by the device on the desired cartridges. In some embodiments, multiple protocols, multiple types of protocols and/or multiple types of cartridges may be used at the same time or in various sequences on the device.

By way of example, embodiments of the bioprocessing cartridge as disclosed with respect FIGS. 12-14 may be used in conjunction with a bioprocessing device described herein to perform any or all of the blocking, washing, antibody binding, and/or detection steps of a western blot after the protein is transferred to the blot membrane. An example of one embodiment of how such a process may be conducted follows. It should be understood that the following procedure is provided by way of example only and that one or more of the steps may be modified and/or deleted and that other types of bioprocessing may be performed using the bioprocessing device and bioprocessing cartridge and other protocols and the same or different bioprocessing cartridge configurations:

1) A bioprocessing device is prepared for processing by inserting a fluid container holder into the removable fluid holder tray and slid into the bioprocessing device. The fluid container holder includes, for each blot membrane to be processed, a container containing an appropriate amount of blocking buffer, a container containing an appropriate amount of wash buffer, a container containing an appropriate amount of primary antibody, a container containing an appropriate amount of secondary antibody and a container containing an appropriate amount of water. It should be understood that the fluid container holder may be supplied to the user with one or more of the containers, that may be supplied pre-filled or may be filled by the user. In some embodiments, at least one or the containers is pre-filled, while in other embodiments all or none of the containers are pre-filled.

2) A blot membrane upon which the protein to be detected has been transferred is inserted into a blot membrane holder and into the bioprocessing chamber of a bioprocessing cartridge configured as described in FIGS. 12-14 through the open top of the bioprocessing chamber. Multiple cartridges may be used, each with its own blot membrane, blot membrane holder and fluid containers in the fluid container holder.

3) The bioprocessing cartridges are inserted into the slots of the bioprocessing device and secured to the cartridge holders. The fluid manifolds for each cartridge are attached to the control fluid connectors of the cartridge by inflating the bladders associated with each cartridge holder. The operator ensures that the aspiration/expiration tubes are placed within the appropriate containers on the fluid container holder.

4) The bioprocessing device may confirm proper insertion of the tray and the cartridges and that the cartridges have not been used previously.

5) The operator selects a desired protocol on the automated control system for the cartridges and initiates it. All of the access valves are ensured to be closed at this time by verifying their actuation state.

The remainder of this example procedure will be described with respect to a single cartridge and occurs automatically and hands-free once the protocol is selected:

6) The automated control system, using pressure and/or vacuum through the appropriate control fluid channels actuates the membrane of the access valve associated with the blocking buffer container to open and actuates the pump and the process fluid valve associated with flow channel connecting to the lower center portion of the bioprocessing chamber (the "center valve") on the cartridge to pump blocking buffer from the blocking buffer container and into the bioprocessing chamber. After the blocking buffer has been pumped into the bioprocessing chamber, the blocking buffer access valve is actuated to a closed position.

7) Blocking buffer is recirculated across the bioprocessing chamber and the blot membrane by withdrawing buffer through one of the process fluid valves associated with the flow channels entering the side of the bioprocessing chamber ("the side valve") by actuating the pump and then pumping the withdrawn fluid back into the bioprocessing chamber through the center valve. Either side valve may be used depending on the size of the blot membrane. The recirculation may occur as follows. The side valve is opened and buffer is pumped into the pump through the side valve and the associated flow channel. The side valve is closed and the center valve is opened. The pump is actuated to pump the blocking buffer from the pump into the bioprocessing chamber through the center valve and the center valve is closed and the procedure is repeated for the selected time in the protocol. Each return of fluid to the bioprocessing chamber may cause the blot membrane to move slightly and may cause localized formation of eddies or formation of turbulence that ensures good or substantially uniform exposure of the surface of the blot membrane to the blocking buffer.

8) Once blocking is complete, the buffer is pumped from the chamber through the center valve and into a waste container on the fluid container holder by alternately opening the center valve, pumping fluid into the pump, closing the center valve, opening the waste container access valve and pumping the fluid into the waste container.

9) In this manner, the blot membrane may be washed, primary antibody may be incubated with the membrane, the membrane may be washed again, secondary antibody may be incubated with the membrane, the membrane maybe further washed and rinsed all according to the automated protocol with no interaction with the user required. Any or all of the above steps may include recirculation of the process fluid described above. After the final rinse, the device may provide an alarm to signal completion and the cartridges may be removed from the device and the blot membranes removed from the cartridges for further processing, such as protein detection and analysis.

The antibodies, blocking buffers, wash buffers, and development/detection solutions may include any suitable compositions for use in immunoblotting procedures without limitation. The antibodies, blocking buffers and wash buffers may be supplied commercially either alone or as a component of a kit, or may be prepared by the end user. By way of non-limiting example, antibodies used in accordance with the presently described embodiments may include one or more primary antibodies, one or more secondary antibodies, or one or more primary antibodies in combination with one or more secondary antibodies.

Suitable primary antibodies may include any antibodies selected by a user for use with the presently described system. In some embodiments, the primary antibody may be directed against a user defined antigen. In some embodiments, the primary antibody may be a complex mixture of antibodies recognizing a plurality of antigens. A primary antibody may be purchased commercially or may be made by the user.

A primary antibody may be a polyclonal antibody or a monoclonal antibody. A monoclonal antibody may be raised in mouse or in rat. A monoclonal antibody may be IgG (IgG1, IgG2a, IgG2b, IgG3), IgM, IgA, IgD and IgE subclasses. A polyclonal antibody may be raised in rabbit, mouse, rat, hamster, sheep, goat, horse, donkey or chicken. In an embodiment, an antibody may be derived from human serum. A human antibody may be at least partially or fully purified. Methods of preparing and purifying antibodies are widely known in the art. General guidance in the production, purification and use of various antibody preparations may be found, for example, in the reference texts Harlow et al., 1989, Antibodies: A Laboratory Manual, Cold Spring Harbor, N.Y., Harlow et al., 1999, Using Antibodies: A Laboratory Manual, Cold Spring Harbor Laboratory Press, NY, and Harlow, et al., 1988, In: Antibodies, A Laboratory Manual, Cold Spring Harbor, N.Y., all of which are hereby expressly incorporated by reference in their entirety.

In some embodiments, a primary antibody may be a "loading control antibody". The loading control antibody may be provided by the user or may be provided commercially as part of the presently described system. Exemplary though non-limiting loading control antibodies that may be used or supplied with the presently described systems and methods may include antibodies directed against actin, tubulin, histone, vimentin, lamin, GAPDH, VDAC1, COXIV, hsp-70, hsp-90 or TBP.

The concentration of primary antibody in an immunoblotting buffer will of course vary, depending on the specific primary antibody being used, the context in which the antibody is being used, and various other properties inherent in the antibody. The determination of an appropriate primary antibody concentration to use in any given experimental scenario is well within the skill level of a practitioner having ordinary skill in the art. Typically, the concentration of the primary antibody will be 1:10 to 1:20,000, 1:100 to 1:15,000, 1:1,000 to 1:10,000 or 1:1,500 to 1:5,000.

Suitable secondary antibodies for use in accordance with the presently described systems and methods include any antibody capable of recognizing and binding to a primary antibody. A secondary antibody may optionally be coupled to one or more detection means. It will be readily apparent to the skilled artisan that what constitutes a suitable secondary antibody will of course vary, depending on the identity of the one or more primary antibodies used in conjunction with the secondary antibody. Generally, a secondary antibody will be selected to bind to at least a portion of the primary antibody being used. Selection of an appropriate secondary antibody further depends on the methods that will be used to detect the signal in later steps. If an end user is using a chemiluminescent technique to detect an analyte, then a suitable secondary antibody may be coupled to, e.g., a peroxidase enzyme. If an investigator is using colorimetric techniques to detect an analyte, then a suitable secondary antibody may be coupled to, e.g., an alkaline phosphatase enzyme. If an investigator is using fluorometric techniques to detect an analyte, then a suitable secondary antibody may be coupled to a fluorophore (including but not limited to FITC, TRITC, Texas-Red, Alexa-Fluor reagents, quantum dots, semiconductor nanocrystals, etc.). Optionally, a secondary antibody may be coupled to one or more biotin moieties and the detection molecule (e.g., peroxidase, phosphates, fluorophore etc.) may be coupled to avidin or streptavidin. Using such a biotin/avidin system may, in some cases, amplify weak signals. Typically, the concentration of the secondary antibody will be 1:10 to 1:20,000, 1:100 to 1:15,000, 1:1,000 to 1:10,000 or 1:1,500 to 1:5,000.

A suitable secondary antibody for use with the presently described systems and methods may be raised, for example, in rabbit, mouse, rat, hamster, pig, sheep, goat, horse, donkey, turkey or chicken. The secondary antibody will typically be raised in a different species than the species in which the primary antibody was raised. The secondary antibody will be generated such that it recognizes and binds to a portion of the primary antibody. The secondary antibody may be at least partially affinity purified. The secondary antibody may be directed against mouse IgG, mouse IgA, mouse IgM, rat IgG, rat IgA, rat IgM, rabbit IgG, rabbit IgA, rabbit IgM, hamster IgG, hamster IgA, hamster IgM, goat IgG, goat IgA, goat IgM, horse IgG, horse IgA, horse IgM, sheep IgG, sheep IgA, sheep IgM, donkey IgG, donkey IgA, donkey IgM, chicken IgG, chicken IgA, chicken IgM, chicken IgY, human IgG, human IgA, or human IgM. A secondary antibody may be coupled to one or more detection molecules such as, by way of example, alkaline phosphatase, peroxidase, biotin, a fluorophore or quantum dots or semiconductor nanocrystals.

A blocking buffer may include an appropriate blocking reagent dissolved or dispersed in a diluent. A suitable blocking reagent may include, by way of non-limiting example, whole serum, fractionated serum, bovine serum albumin, casein, soy protein, non-fat milk, gelatin, fish serum, goat immunoglobulin, rabbit immunoglobulin, mouse immunoglobulin, rat immunoglobulin, horse immunoglobulin, human immunoglobulin, pig immunoglobulin, chicken immunoglobulin or synthetic blocking reagents, such as those that may be obtained commercially from, e.g., BioFX Laboratories, Kem-En-Tec Diagnostics or GeneWay Biotech. A variety of commercially available pre-prepared blocking reagents are available, all of which may be supplied with a kit as described herein. Such commercially available blocking reagents include, though are not limited to, e.g., WesternBreeze, I-BLOCK, BlockIt, PerfectBlock, Synthetic Blocking Buffer (BioFX Labs), Gelantis BetterBlock, SeaBlock, Starting Block and Protein-Free Blocking Buffer (Pierce). In embodiments where the blocking reagent is supplied dissolved or dispersed in the diluent, the amount of the blocking reagent present may be in the range of about 0.1 wt.% to about 50 wt.%, about 1 wt.% to about 40 wt.%, about 2.5 wt.% to about 25 wt.%, about 5 wt.% to about 15 wt.% or about 10 wt%. In an embodiment, the amount of a blocking reagent present in an immunoblotting buffer may be up to about 75 mg/ml, up to about 50 mg/ml, up to about 40 mg/ml, up to about 30 mg/ml, up to about 20 mg/ml, up to about 15 mg/ml, up to about 10 mg/ml up to about 5 mg/ml, up to about 2.5 mg/ml, up to about 1 mg/ml, up to about 0.5 mg/ml, up to about 0.25 mg/ml or up to about 0.1 mg/ml. Suitable diluents that may be used as a carrier medium for blocking reagents include any aqueous buffers having substantially physiologic pH and ionic strength. Exemplary though non-limiting diluents may include any buffer containing phosphate ions, bicarbonate, TAPS, Bicine, Tris, Bis-Tris, Tricine, HEPES, TES, MOPS, PIPES, Cacodylate, MES, acetate, ADA, ACES, cholamine, BES, acetamidoglycine or glycinaide present therein. Exemplary buffers suitable for use as diluents may include, though are not limited to, e.g., PBS, Hank's solution, TBS, TE, TEN, or the like. Optionally, a diluent may include a detergent. Suitable detergents may include non-ionic, non-denaturing detergents such as, e.g., Triton X-100, Triton X-114, NP-40, Brij-35, Brij 58, Tween-20, Tween-80, octyl glucoside and octylthio glucoside and detergents such as sulfabetaines, including SB-12, SB-14 and SB-16. A diluent may contain from about 0.01 vol.% to about 5 vol.%, from about 0.05 vol.% to about 2 vol.%, from about 0.1 vol.% to about 1.5 vol.%, or from about 0.5 vol.% to about 1 vol.% of a detergent.

In some embodiments, a suitable wash buffer may be the same as the diluent in which the blocking reagents are dispersed, as described above. In some embodiments, the wash buffer may be the diluent lacking one or more components thereof. In some embodiments, the wash buffer may be the diluent lacking a blocking reagent.

In some embodiments, a wash buffer or a diluent may be supplied at full strength (i.e., 1× strength) or may be supplied as a concentrated solution that facilitates storage and shipping thereof. A concentrated wash buffer or diluent may be diluted by the user using, for example deionized water, sterile water or any other suitable diluent. Concentrated wash buffers/diluents may be supplied as up to about 50×, up to about 25×, up to about 20×, up to about 10×, up to about 5× or up to about 2× strength.

In some embodiments, a wash buffer/diluent may be supplied to a user in one or more plastic or glass bottles supplied with the kit. Each kit may include between 1 to 10 bottles of a wash buffer, between 1-5 bottles of a wash buffer, or between 1-2 bottles of a wash buffer. Each bottle of diluent may contained up to 5 L, up to 4 L, up to 3 L, up to 2 L, up to 1 L, up to 500 ml, or up to 100 ml of a diluent.

By way of example, embodiments of the bioprocessing cartridge as described with respect to FIGS. 16-18 may be used in conjunction with a bioprocessing device described herein to perform the cell separation, lysing, clarification, binding, washing, elution, precipitation and/or collection steps of nucleic acid processing, including processing for collection of nucleic acids such as DNA or fragments thereof, including plasmid DNA, genomic DNA, viral DNA and bacterial DNA or fragments of any of the above. An example of one embodiment of how such a process may be conducted is follows. It should be understood that the following procedure is provided by way of example only and that one or more of the steps may be modified and/or deleted and that other types of bioprocessing may be performed using the bioprocessing device and bioprocessing cartridge and other protocols and the same or different bioprocessing cartridge configurations:

1) A bioprocessing device is prepared for processing by inserting a fluid reservoir holder for each sample to be processed into the removable fluid holder tray and slid into the bioprocessing device. Each fluid reservoir holder includes, a sample container into which the sample is inserted, a waste container, an RNase reservoir, a resuspension buffer reservoir, a lysis buffer reservoir, a neutralization buffer reservoir, a wash solution reservoir, an elution solution reservoir, an isopropanol reservoir, an ethanol reservoir, a collection buffer reservoir, and a collection reservoir, each reservoir containing an appropriate amount of the relevant solution (or is empty such as for the waste and collection containers). The fluid reservoir holder may be supplied with empty reservoirs or with pre-filled reservoirs, with only the sample needing to be added. In some embodiments, one or more of the reservoirs may be pre-filled, while one or more of the reservoirs may be filled by the user. In some embodiments, the fluid reservoir holder is supplied with at least one reservoir pre-filled, while in other embodiments, the fluid reservoir holder is supplied with no reservoirs and/or the one or more reservoirs are supplied empty.

2) For each sample to be processed, a bioprocessing cartridge is inserted into a slot of the bioprocessing device and secured to the cartridge holder. The fluid manifold for each cartridge is attached to the control fluid connectors of the cartridge by inflating the bladder associated with the cartridge holder. The operator ensures that the aspiration/expiration tubes are placed within the appropriate containers on the fluid container holder when inserting the cartridge into the slots and the cartridge holder.

3) The bioprocessing device may confirm proper insertion of the tray and the cartridges.

4) The operator selects a desired protocol which may be pre-programmed into the device or may be user-defined on the automated control system for the cartridges and initiates it. All of the access valves are ensured to be closed at this time by verifying their actuation state.

The remainder of this example procedure will be described with respect to a single cartridge with reference to the reference numbers in FIGS. 18A-B, and occurs automatically and hands-free once the protocol is selected:

6) The automated control system, using pressure and/or vacuum through the appropriate control fluid channels opens membrane access valve 1818 associated with the sample, actuates pump 1810 and pumps the sample through process fluid valves 1846 and 1852 associated with the process fluid channel connecting to the inlet at the upper central portion of the cell separation bioprocessing chamber 1803 on the cartridge, through a filter membrane in chamber 1803, out of the chamber through the outlet of chamber 1803 at the bottom central portion of the chamber on the back or control fluid layer of the cartridge, through pass-through 1872 and back to the process fluid layer of the cartridge and out through access valve 1820 and into the waste container on the fluid container holder, actuating the appropriate valves open and closed as necessary to allow fluid to flow through the correct process fluid channels and to prevent fluid from flowing down the wrong process fluid channels at the wrong times. The cells in the sample are captured on the filter in chamber 1802.

7) Media remaining in the chamber 1803 and in the process fluid channels leading to the chamber 1803 and in the pump 1810 is removed by blowing air, such as a pulse of air or a continuous stream of air, at approximately 30-40 psi from the control fluid layer, through check valve 1868 to the process fluid layer, through pump 1810, process fluid valves 1846 and 1852, across the filter in bioprocessing chamber 1803, out of the chamber 1803 through the outlet of chamber 1803 at the bottom central portion of the chamber 1803 on the back or control fluid layer of the cartridge, through pass-through 1872 and back to the process fluid layer of the cartridge and out through access valve 1820 and into the waste container on the fluid container holder.

8) Using pump 1810, RNase is pumped from the RNase reservoir through access valve 1822 into pump 1810, and through access valve 1824 and into the resuspension buffer reservoir.

9) The cells on the filter membrane in chamber 1803 are resuspended using pump 1810, by pumping the resuspension buffer (with RNase) through access valve 1824, through pump 1810, through process valve 1840 and pass-through 1872 where it is moved to the control fluid layer, through the outlet (used as an inlet this time) at the bottom central portion of the chamber 1803 on the back or control fluid layer of the cartridge, into chamber 1803 and across the filter (in the reverse direction from the cell separation in steps 6-7) out of the chamber 1802 through the inlet (used as an outlet this time) at the upper central portion of the cell separation bioprocessing chamber 1803, through process valve 1852 and access valve 1826 and into the lysis buffer reservoir.

10) Any remaining cells in the chamber 1803 and in the process fluid channels leading from chamber 1803 to the lysis reservoir are removed by blowing air, such as a pulse of air or a continuous stream of air, at approximately 30-40 psi from the control fluid layer, through check valve 1868 to the process fluid layer, through process valve 1840 and pass-through 1872 where it is moved to the control fluid layer, through the outlet (used as an inlet this time) at the bottom central portion of the chamber 1803 on the back or control fluid layer of the cartridge, into chamber 1803 and across the filter (in the reverse direction from the cell separation in steps 6-7) out of the chamber 1803 through the inlet (used as an outlet this time) at the upper central portion of the cell separation bioprocessing chamber 1803, through process valve 1852 and access valve 1826 and into the lysis buffer reservoir.

11) The cell are lysed by gently mixing the solution in the lysis buffer reservoir back and forth between the lysis buffer reservoir and the resuspension reservoir by pumping it using pump 1810 from the lysis buffer reservoir, through access valve 1826, through process valve 1846, through pump 1810, through access valve 1824 and into the resuspension buffer reservoir and back again. This back and forth may occur as often as necessary to lyse the cells and the solution may ultimately end up in either of the reservoirs.

12) Assuming the lysed cells are in the resuspension buffer reservoir, neutralization buffer is pumped, using pump 1810 from the neutralization buffer reservoir, through access valve 1828, through process valve 1846, through pump 1810, through access valve 1824 and into the resuspension buffer reservoir. The solution may be mixed by pumping through this route back and forth and the may end up ultimately in either reservoir where the layers formed are allowed to separate.

13) Assuming the lysed and neutralized cells are in the resuspension buffer, the lysate may be clarified by pumping, using pump 1810, the lysate through access valve 1824, through pump 1810, through process valve 1848, into bioprocessing chamber 1804 through the inlet at the top central portion of the chamber, through a clarification filter within chamber 1804, where the cellular and other debris is removed, out of chamber 1804 through the outlet at the bottom central portion of the chamber on the control fluid layer, through pass-through check valve 1870 to the process fluid layer, across check valve 1866 (while being prevented by the valve from passing through to the control fluid layer), through pass-through 1874 back to the control fluid layer, into bioprocessing chamber 1806 through a bottom central inlet, across a DNA-binding solid phase extraction filter, membrane, disk or cassette, out of bioprocessing chamber 1806 through an outlet at the top central portion of chamber 1806 on the process fluid layer, through process valve 1858 and access valve 1818 and into the sample container, which will now serve as a waster container.

14) The solid phase extraction filter, membrane, disk or cassette is washed by pumping wash solution from the wash solution container using pump 1812, through access valve 1830, through pump 1812, through process valve 1850, across check valves 1870 and 1866 while being prevented from passing through them, through pass-through 1874 to the control fluid layer, into bioprocessing chamber 1806 through a bottom central inlet, across a DNA-binding solid phase extraction filter, membrane, disk or cassette, out of bioprocessing chamber 1806 through an outlet at the top central portion of chamber 1806 on the process fluid layer, through process valve 1858 and access valve 1818 and into the sample (waste) container.

15) After the wash step, any remaining wash solution is removed from bioprocessing chamber 1806, by blowing air, such as a pulse of air or a continuous stream of air, at approximately 30-40 PSI from the control fluid layer, through check valve 1866, to the process fluid layer, through pass-through 1874 where it is moved to the control fluid layer, through the inlet at the bottom central portion of the chamber 1806 across the filter, out of the chamber 1806 through the outlet at the upper central portion of the bioprocessing chamber 1806, through process valve 1858, and through access valve 1818 and into the sample (waste) container.

16) The bound DNA is eluted from the solid phase extraction filter, membrane, disk or cassette by pumping, using pump 1812, elution solution from the elution solution reservoir, through access valve 1832, through pump 1812, through access valve 1850, across check valves 1870 and 1866 while being prevented from passing through them, through pass-through 1874 to the control fluid layer, into bioprocessing chamber 1806 through a bottom central inlet, across a DNA-binding solid phase extraction filter, membrane, disk or cassette, out of bioprocessing chamber 1806 through an outlet at the top central portion of chamber 1806 on the process fluid layer, through access valve 1860, through pump 1814, through access valve 1834 and into the isopropanol reservoir.

17) The solution in the isopropanol container is mixed by gently mixing the solution in the isopropanol container back and forth between the isopropanol container and the elution solution container by pumping it using pumps 1814 and 1812 from the isopropanol container, through access valve 1834, through pump 1814, through process valve 1854, through pump 1812, through access valve 1832 and into the elution solution container and back again. This back and forth may occur as often as necessary to mix the solutions and the solution should ultimately end up in the isopropanol container.

18) The DNA is captured on a precipitator in bioprocessing chamber 1808 by pumping using pump 1814, the solution in the isopropanol container through access valve 1834, through pump 1814, through access valve 1856 and through an inlet in an upper portion of bioprocessing chamber 1808, into chamber 1808, across a precipitator filter within chamber 1808, out an outlet in a bottom portion of chamber 1808 on the control fluid layer, through pass-through 1873, through process valve 1863 and access valve 1818 and into the sample (waste) container.

19) The precipitator is washed with ethanol by pumping ethanol from the ethanol container using pump 1814, through access valve 1836, through pump 1814, through access valve 1856 and through an inlet in an upper portion of bioprocessing chamber 1808, into chamber 1808, across a precipitator filter within chamber 1808, out an outlet in a bottom portion of chamber 1808 on the control fluid layer, through pass through 1873, through process valve 1863 and access valve 1818 and into the sample (waste) container.

20) The precipitator is dried by blowing air, such as a pulse of air or a continuous stream of air, at approximately 30-40 PSI from the control fluid layer, through check valve 1864 to the process fluid layer, through process valve 1862, through an inlet in an upper portion of bioprocessing chamber 1808, into chamber 1808, across a precipitator filter within chamber 1808, out an outlet in a bottom portion of chamber 1808 on the control fluid layer, through pass-through 1873, through process valve 1863 and access valve 1818 and into the sample (waste) container.

21) The DNA on the precipitator is eluted into the collection container by pumping the collection buffer from the collection buffer container using pump 1816, through access valve 1838, through pump 1816, through across check valve 1864 while being prevented from passing through it, through process valve 1862, through an inlet in an upper portion of bioprocessing chamber 1808, into chamber 1808, across a precipitator filter within chamber 1808, out an outlet in a bottom portion of chamber 1808 on the control fluid layer, through pass-through 1873, through access valve 1838 and into the collection container.

It should be understood that this procedure is by way of example only and should not be considered to be limiting in any way. Many different procedure can be used with the cartridge of FIGS. 18A-B and the cartridge may be configured in different manners according to different protocols, including to have additional or fewer bioprocessing chambers, different spatial orientations of any of the bioprocessing chambers, the inlets and outlets to the bioprocessing chambers, different flow channel configurations, different numbers, types and spatial orientations of pumps and valves, different numbers and types of containers and process solutions, and different types of samples for processing.

Any suitable buffer, wash solutions, resuspension buffer, lysis buffer, neutralization buffer, RNase, elution/collection buffer, or precipitation buffer may be used with or without any additional suitable reagents depending on the protocol being performed. Suitable buffers, as well as there compositions and methods of use are disclosed in the following U.S. patent references: U.S. Pat. No. 6,914,137, 2006/0154247, 2007/0117972, U.S. Pat. Nos. 6,242,220, 5,990,301, 7,214,508, 7,109,322, and 6,297,371, all of which are hereby incorporated by reference as though fully set forth herein.

Any suitable biologically acceptable buffer such as, e.g., Tris, TAPS, Bicine, Tricine, HEPES, TES, MOPS, PIPES, cacodylate, MES, acetate, or the like, having pH between about 3.5 to about 9, between about 5 to about 8, between about 6.5 to about 7.5 are suitable for use in the preparation of a resuspension buffer in accordance with the presently described systems and methods. In some embodiments, a resuspension buffer may include between 1 mm to 100 mm, between 5 mm to 50 mm, or between 10 mm to 20 mm of a chelating agent such as, e.g., EDTA, EGTA, ALA, BAPTA, defarasirox, deferiprone, deferoxamine, DTPA, dimercaprol, DMPS, DMSA, or the like. In some embodiments, a resuspension buffer may optionally include RNase such as endoribonucleases and exoribonucleases, including RNase A, RNase H, RNase I, RNase III, RNase L, RNase P, RNase PhyM, RNase T1, RNase T2, RNase U2, RNase V1, RNase V, PNPase, RNase PH, RNase II, RNase R, RNase D, RNase T, Exoribonuclease I, Exoribonuiclease II and the like. In some embodiments, the RNase A formulation may include 2.4 mg/ml RNase A, 50 mm Tris-HCL with a pH of 8.0, and 10 mm of EDTA. In some embodiments, a resuspension buffer may optionally include lysozyme. In some embodiments, a resuspension buffer may optionally include between about 1 mm to about 500 mm, between about 10 mm to about 200 mm, between about 20 mm to about 100 mm, between about 30 mm to about 75 mM of a carbohydrate such as a sugar. Exemplary sugars include glucose, fructose, galactose, mannose, maltose, lactose, and the like. An exemplary resuspension buffer may include an aqueous solution containing 50 mm Tris, pH 7.4, 100 μg/ml RNase A1, 10 mm EDTA, and 5 mm glucose. In some embodiments the resuspension buffer may include an aqueous solution including 50 mm Tris with a pH of 8.0, and 10 mm EDTA.

Suitable lysis solutions or buffers may include, in an aqueous carrier medium, one or more denaturants in combination with one or more lipid disruptive agents. The denaturants may be nucleic acid denaturants such, e.g., an alkaline salt. Suitable alkaline salts may include sodium hydroxide, potassium hydroxide, calcium hydroxide, and the like. Suitable lipid disruptive agents may include ionic surfactants. Exemplary ionic surfactants include sodium cholate, Sodium dodecylsulfate (SDS), sodium deoxycholate (DOC), N-lauroylsarcosine salts, cetyltrimethylammoniumbromide (CTAB), Bis (2-ethylhexyl)sulfosuccinate salts, and the like. In some embodiments, the lysis buffer ay be a formulation including 1% SDS and 200 mm Sodium Hydroxide.

An exemplary lysis solution may include an aqueous solution containing between about 10 mm to about 500 mm, from about 50 mm to about 250 mm or from about 100 mm to about 200 mm NaOH, in combination with up to about 10% SDS, up to about 5% SDS or up to about 1% SDS. Additional agents may be present in the lysis buffer, as will be readily apparent to one skilled in the art.

Suitable neutralization solutions may include, in an appropriate aqueous carrier medium, one or more agents capable of neutralizing the surfactants/alkaline solution present in the lysis solution. In some embodiments, a neutralization solution may include between about 0.5 M to about 5 M of an appropriate acetate salt, having pH>4. An exemplary neutralization solution may include an aqueous solution of about 3 M potassium acetate, pH~5.

A suitable wash buffer may include, in an appropriate aqueous carrier medium, between 0.1 mm to about 100 mm salt, between about 0.5 mM to about 500 mm of an appropriate biological buffer such that the pH of the wash buffer is at least about 6.0 or higher, and at least 5 vol. %, at least 10 vol. % or at least 15 vol. % of an appropriate alcohol such as ethanol or isopropyl alcohol. Optionally, a wash buffer may include between about 0.01 vol. % to up to about 10 vol. % of a suitable non-ionic detergent such as, e.g., TRITON® X-100, CHAPS or NP-40. The addition of such a detergent may, in some embodiments, enhance the removal of unwanted endotoxins from the preparation. An exemplary wash buffer may include 1 M NaCl, 50 mm MOPS, pH>8.0, 15 vol. % isopropyl alcohol and 0.5 vol. % TRITON® X-100. In some embodiments, the wash buffer may include an aqueous solution including 800 mm NaCl and 100 mm sodium acetate Trihydrate with a pH of 5.0. In some embodiments, the wash buffer may be a formulation including, e.g., 1.5 NaCl, 100 mm Sodium Acetate Trihydrate at a pH of 5.0.

A suitable collection/elution buffer may include, in an appropriate aqueous carrier medium, up to about 50 mm of an appropriate biological buffer having 5.0<pH<9.0 and up to about 10 mm of an appropriate chelating agent. An exemplary collection/elution buffer may include 10 mm Tris HCL with a pH of 8.0 in combination with 1 mm EDTA.

In some embodiments, an equilibration buffer may optionally be passed through the solid support matrix prior to the use thereof. An equilibration buffer may include up to 1 M of a salt, up to 500 mm of an appropriate biological buffer having 5.0<pH<9.0, up to about 10 vol. % of an appropriate non-ionic detergent and up to about 20 vol. % alcohol. An exemplary equilibration buffer may include, e.g., 750 mm NaCl, 50 mm MOPS, pH 7, 15 vol. % isopropyl alcohol, and about 0.15 vol % TRITON® X-100.

In some embodiments, a precipitation buffer may optionally be passed through the solid support matrix prior to the use thereof. A precipitation buffer may include up to 5 M potassium acetate, up to 500 mm of an appropriate biological buffer having 5.0<pH<9.0. An exemplary precipitation buffer may include, e.g., 3.1 M Potassium Acetate with a pH of 5.5.

Further provided herein is an alternate method of purifying nucleic acid using an embodiment of a bioprocessing device including one or more of: selecting the number of cartridges to be used; inserting the cartridges into a bioprocessing device; inflating the bladder to further stabilize the cartridge; pumping cells from the sample container through a bioprocessing chamber into the waste container for 2100 secs with a pump delay of 700 ms between pumps to capture cells; releasing pressure within the cartridge for 1 second; aspirating Rnase into the cartridge for 4 seconds using a pump with a delay of 800 ms between pump strokes; mixing the resuspension buffer with the lysis buffer by pumping the resuspension buffer into the lysis buffer reservoir for 50 secs using a pump delay of 800 ms between pump strokes; pumping the resuspension buffer/lysis buffer mixture back to the resuspension buffer reservoir for 80 using a pump with an 800 ms delay between pump strokes; pump the resuspension/lysis buffer mixture through the bioprocessing chamber with the captured cells for 150 seconds using a pump with delay of 800 ms between pump strokes to resuspend the cells; preset the valves for 1 sec; mix the lysis/resuspension buffer solution with the cells for 100 seconds using a pump delay of 1200 ms between pump strokes; pump the neutralization mixture into the reservoir containing the resuspended cells and lysis/resuspension buffer solution for 60 seconds using a pump delay of 1200 ms between pump strokes; mix the neutralization mixture with the resuspension/lysis buffer mixture for 270 seconds using a pump delay of 2500 ms between pump strokes; purge the Genomed waste from the system for 1 second; open one of the control fluid connectors for 3 seconds; pumping the lysis/resuspension/neutralization buffer with cells for 400 seconds using a pump dealy of 2500 ms through a second bioprocessing chamber to clarify DNA from the cellular debris and bind the DNA in another bioprocessing chamber; the Genomed filter is then washed for 10 seconds using a pump delay of 800 ms; the valves are then preset for 1 second and the Genomed filter is allowed to air dry for 2 seconds; an elution buffer is than pumped for 20 seconds through the membrane using a pump delay of 1100 ms and the eluted solution is then mixed with isopropyl alcohol twice for 20 seconds using a pump delay of 800 ms; the lines are then purged to waste for 1 second; a process valve then opened in three seconds; the pressure in the cartridge is then released for 1 second; the precipitated DNA mixture is the pumped through another bioprocessing chamber with a PPTR membrane for 60 seconds using a pump delay of 1100 ms to capture the DNA; 70% ETOH is then pumped through the bioprocessing chamber for 20 second using a pump delay of 1100 ms; the remaining ETOH is then purged to waste for 1 second; the PPTR membrane is then dried for 90 seconds; the pressure is then released from the bioprocessing cartridge for 1 second; a final elution solution is then pumped through the PPTR membrane for 120 seconds using a pump delay of 3000 into a collection tube; once the run is complete, the bladder is then deflated for 20 second, so the cartridge can be removed. The entire protocol takes about 3690 seconds to run.

Additional embodiments, instruments, methods and cartridges are described below. In the dimensions provided for the cartridge below, height is the Y axis going up and down, width is the X axis going left to right and depth is the Z axis (or smallest dimension) going into the page of an embodiment of the bioprocessing cartridge when viewed as shown in FIG. 13A.

IV. Examples

Unless otherwise stated in the Examples, the automated processing of the western blots was conducted using the upper process channel and valve on the bioprocessing card. This channel is generally the channel associated with process valve 1227 in FIG. 12.

A. Examples 1 & 2

A western blot was performed using an embodiment of the automated processing device as shown in FIGS. 1C & 1D and an embodiment of the bioprocessing cartridge as shown in FIGS. 12, 13A-B and 14, the results (FIG. 24A) of which were compared to a manual method (FIG. 24B) as follows:
Reagents and Equipment
NuPAGE® LDS Sample Buffer (Invitrogen cat #NP0007)
NuPAGE® MES SDS Running Buffer (Invitrogen cat #NP0002)
NuPAGE® Reducing Agent (Invitrogen cat #NP0004)
SeeBlue® Plus2 Prestained Standard (Invitrogen cat #LC5925)
NuPAGE® Antioxidant (Invitrogen cat #NP0005)
Gels=NuPAGE® 4-12% BT IPG Well (Invitrogen cat #NP0330BOX)
iBlot Gel Transfer Device (Invitrogen cat #IB1001)
iBlot Regular Transfer Stack—Mini (nitrocellulose) (Invitrogen cat #1B3010-02)
WesternBreeze® Chromogenic Kit—Anti Rabbit (Invitrogen cat #WB7105)
Rabbit anti-*E. coli* antibody (Dako cat #B0357)
Protocol
1. Western Blot Preparation: 4 µg of an *E. coli* lysate were prepared in NuPAGE LDS sample buffer and 5 µl SeeBlue® Plus2 standard and were loaded onto a NuPAGE 4-12% BT IPG well format gel and run at 200V for 34 minutes. The proteins on the gel were then transferred onto a nitrocellulose membrane (iBlot Regular Transfer Stack) using an iBlot Gel Transfer Device according to the instructions in the users manual provided with the device.

2. Immunodetection Reagent Preparation: Blocker, wash buffer and primary antibody diluent were prepared using reagents contained in the WestemBreeze® Chromogenic Kit as described in the user's manual provided with the kit. The Dako anti-*E. coli* primary antibody was diluted 1:1000 in primary antibody diluent. The secondary antibody used was the ready to use alkaline phosphatase conjugated goat anti-rabbit antibody contained in the WestemBreeze® Chromogenic Kit. Sufficient reagents were prepared in one batch to process both the blot processed with the automated instrument and the blot processed using the manual method (see below).

3. Blot Processing: The nitrocellulose membrane (after transfer) described in section 1 of this protocol was cut in half, one half used for an immunodetection performed in the automated instrument, the other half processed using the standard manual procedure as described in the WestemBreeze® Chromogenic Kit user manual in a Falcon dish provided with the kit.

4. Automated Instrument: The following reagents were loaded into an embodiment of the tray of the automated instrument as shown in FIG. 6: blocker, rinse (water), Primary antibody, Wash (WestemBreeze® wash buffer), Secondary Antibody, Wash (WesternBreeze® wash buffer—a second aliquot), rinse (water—a second aliquot). A bioprocessing cartridge was inserted into a slot of the instrument, half of the blot membrane was loaded into an embodiment of a blot holder as shown FIG. 21A (made from die cut PVC film) and inserted into the bioprocessing chamber of the bioprocessing cartridge in the instrument.

5. Automated Protocol: After insertion of the blot into the bioprocessing cartridge a protocol was initiated on the instrument, the protocol consisting of the following steps, each iteration/step being performed automatically with no further human interaction required, though the progress of each step and of the protocol was indicated on the GUI.
 a. Block: 1×30 minutes—WesternBreeze® blocker
 b. Rinse: 2×5 minutes—Water
 c. Primary Antibody: 1×60 minutes—1:1000 rabbit anti-*E. coli* antibody in antibody diluent
 d. Wash: 4×5 minutes—WesternBreeze® wash buffer
 e. Secondary Antibody: 1×30 minutes—WesternBreeze® goat anti-rabbit AP conjugate
 f. Wash: 4×5 minutes—WesternBreeze® wash buffer
 g. Rinse: 3×2 minutes—Water For each iteration of the above steps, the time indicated did not include the filling time of the chamber with the relevant reagent and only represents the recirculation time of the reagent through the chamber. At the end of each iteration of each of the steps the chamber was drained before starting the next iteration/step and the drain time is also not included in the indicated time. The filling/drain times were relatively short, on the order of about 1 minute for all of the steps or iterations. As used herein and throughout the Examples a number followed by an "×" followed by a time is intended to represent the number of iterations of that step performed for the indicated time. Thus, as included above "Rinse: 2×5 minutes" means 2 iterations of filling of the chamber with water, recirculation of the water for 5 minutes and draining of the water, or, in other words filling of the chamber with water, recirculation of the water for 5 minutes and draining of the water (1 iteration) followed by filling of the chamber with water, recirculation of the water for 5 minutes and draining of the water ($2^{nd}$ iteration).

The manual method used the same lengths of times and number of iterations for each step as the automated method, but each iteration/step was performed by hand. A summary of the manual method is as follows: The half of the blot for manually processing was first placed in the Falcon dish supplied with the WesternBreeze® Chromogenic kit, blocker was poured into the dish and the dish was placed on a rotator table for 30 minutes. After 30 minutes, the blocker was poured off by hand and the rinse water was added by hand. This method of manually adding reagents, rotating/incubating for a set time, pouring off, then adding the next reagent was repeated for each iteration of each step listed above for the automated instrument, except they were performed manually.

Figure 24A:
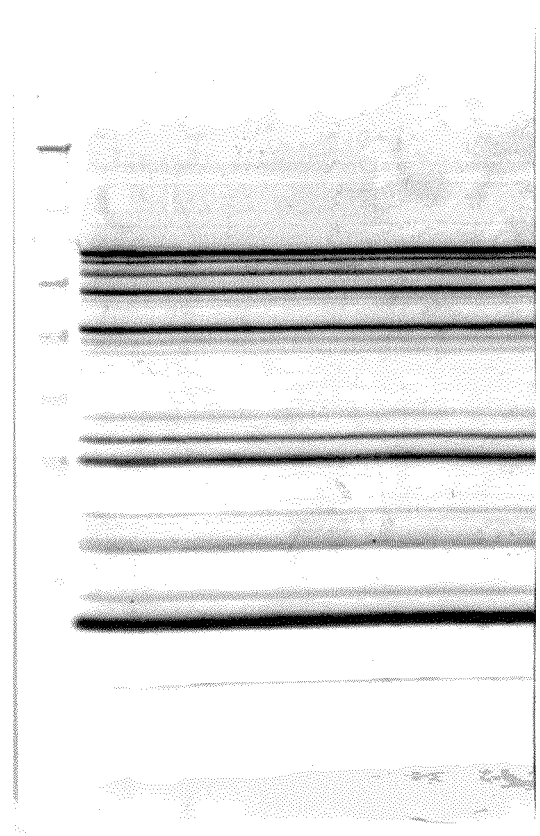
FIGS. 24A & 24B shows results of a the western blots performed as described in Examples 1 and 2.
Figure 24B:
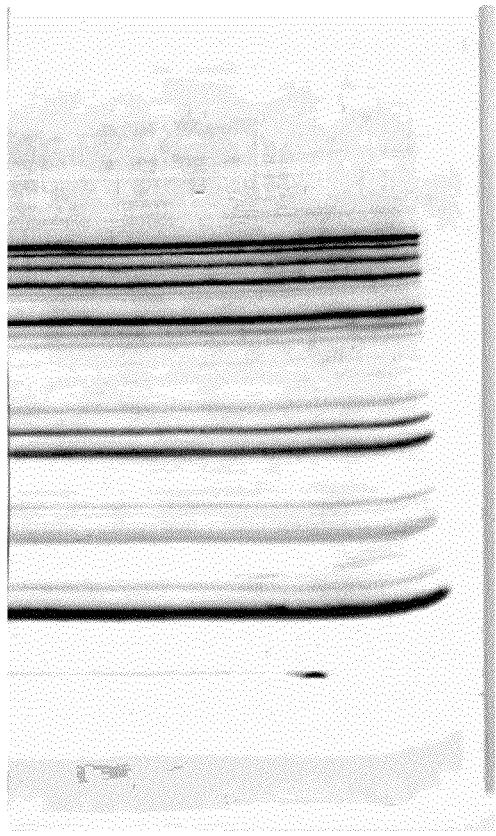

6. Visualization: After the incubation steps above were completed, both blot halves were rinsed with water and incubated in chromogenic substrate (from WesternBreeze® Chromogenic kit) for 20 minutes. The results are shown in FIGS. 24A & B.

B. Examples 3 and 4

Figure 25A:
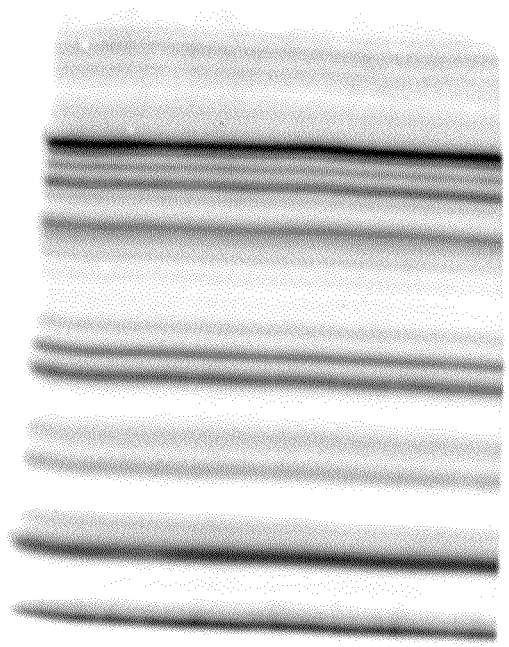
FIG. 25A & 25B shows the results of the western blots performed as described in Examples 3 and 4.
Figure 25B:
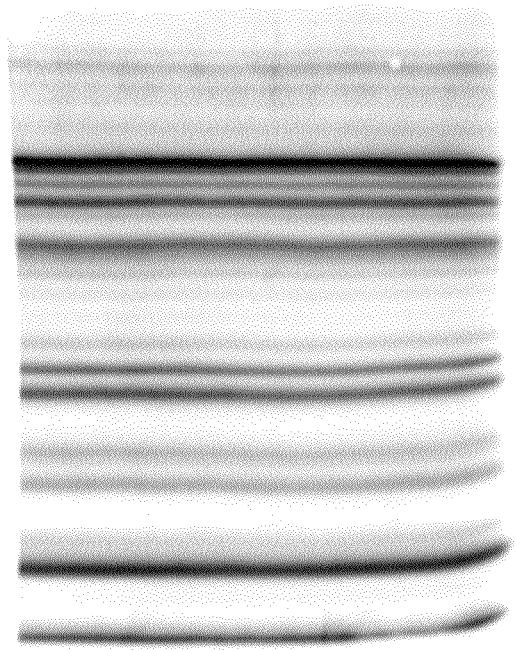

A western blot was performed using an embodiment of the automated processing device as shown in FIGS. 1C&1D and an embodiment of the bioprocessing cartridge as shown in FIGS. 12, 13A-B and 14, the results (FIG. 25A) of which was compared to a manual method (FIG. 25B) as follows:

Reagents and Equipment
NuPAGE® LDS Sample Buffer (Invitrogen cat #NP0007)
NuPAGE® MES SDS Running Buffer (Invitrogen cat #NP0002)
NuPAGE® Reducing Agent (Invitrogen cat #NP0004)
SeeBlue® Plus2 Prestained Standard (Invitrogen cat #LC5925)
NuPAGE® Antioxidant (Invitrogen cat #NP0005)
Gels=NuPAGE® 4-12% BT IPG Well (Invitrogen cat #NP0330BOX)
iBlot Gel Transfer Device (Invitrogen cat # IB1001)
iBlot Regular Transfer Stack—Mini (PVDF) (Invitrogen cat #1B4010-02)
BupH™ Phosphate Buffered Saline (Pierce cat #28372)
Surfact-AMPs® 20 (Pierce cat #28320)
Non-fat dry milk (Carnation)
Goat anti-rabbit IgG HRP conjugate (Jackson cat #111-035-003)
Rabbit anti-*E. coli* antibody (Dako cat #B0357)
ECL HRP Western Blotting Substrate (Pierce cat #32209)
Transparency film for copiers (3M PP2500)
Fuji Luminometer (Fuji LAS-1000)
Protocol
  1. Western blot preparation: 4 µg of an *E. coli* lysate was prepared in NuPAGE® LDS sample buffer and 5 µl SeeBlue® Plus2 standard and was loaded onto a NuPAGE® 4-12% BT IPG well format gel and run at 200V for 34 minutes. The proteins on the gel were then transferred onto a PVDF membrane (iBlot Regular Transfer Stack) using an iBlot Gel Transfer Device.
  2. Immunodetection reagents preparation:
    a. PBST=2 packets of BupH Tris Buffered Saline+10 ml Tween 20 (1 vial of Surfact-Amps 20) were combined and diluted to 1L with deionized water.
    b. Blocker=1.25 g non-fat dry milk (NFDM) was dissolved/diluted to 25 ml with PBST.
    c. Wash buffer=PBST
    d. Primary Antibody Solution=25 ml of PBST was combined with 25 µl Dako anti-*E. coli* primary antibody
    e. Secondary 2° Ab Solution=25 ml PBST was combined with 5 µl Jackson HRP conjugated goat anti-rabbit IgG antibody.
  3. Blot Processing: The PVDF membrane (after transfer) described in section 1 of this protocol was cut in half, one half was used for an immunodetection performed on the automated instrument, the other half was processed using the standard manual procedure as described in a Falcon dish such as that provided in the WesternBreeze immunodetection kit.
  4. Automated Instrument: The reagents were loaded into an embodiment of the instrument tray as shown in FIG. 6, a bioprocessing cartridge was inserted into the instrument, the half of the PVDF membrane was loaded into an embodiment of a blot holder as shown in FIG. 21A and was inserted into the bioprocessing chamber of the bioprocessing cartridge in the instrument.
  5. Automated Protocol: The following steps were performed using the automated instrument and manually substantially as described in more detail in Examples 1-2 above:
    a. Block: 1×30 minutes—5% NFDM in PBST
    b. Rinse: 2×5 minutes—Water
    c. Primary Antibody: 1×60 minutes—1:1000 rabbit anti-*E. coli* antibody in PBST
    d. Wash: 4×5 minutes—PBST
    e. Secondary Antibody: 1×30 minutes—1:5000 goat anti-rabbit HRP conjugate in PBST
    f. Wash: 4×5 minutes—PBST
    g. Rinse: 3×2 minutes—Water
  6. Visualization: After the incubation steps above were completed, both membrane halves were rinsed with water and placed side by side on a piece of plastic copier transparency film. ECL HRP substrate was pipetted onto both halves and left to incubate for 1 minute. Excess substrate was poured off and another sheet of transparency film was placed on top of the membranes, creating a sandwich that was easy to handle and keeps the blots moist during imaging. This blot sandwich was imaged with the Fuji LAS-1000 Luminometer for 3 minutes. The results are shown in FIGS. 25A & 25B.

C. Examples 5-9

Figure 26A:
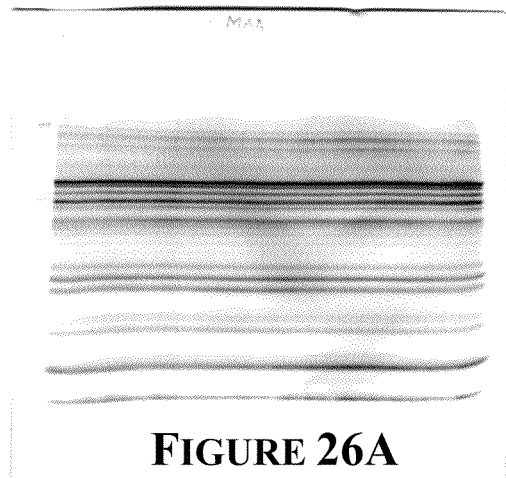
FIGS. 26A-26E shows the results of the western blots performed as described in Examples 5, 6, 7, 8 and 9.
Figure 26B:
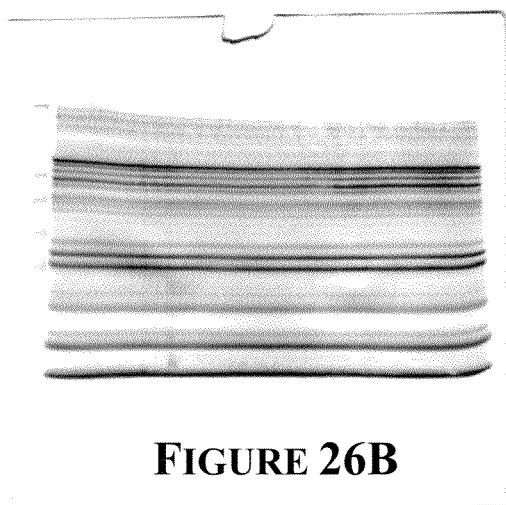
Figure 26C:
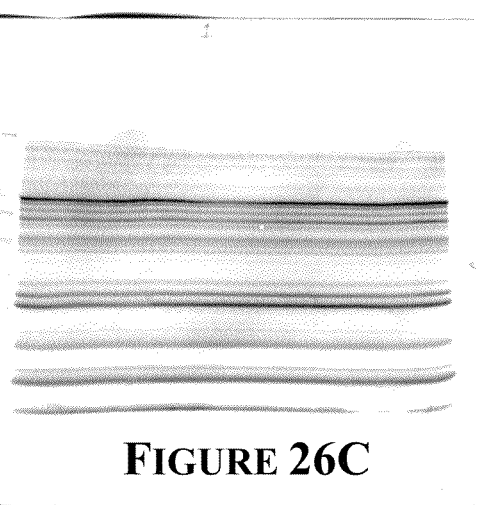
Figure 26D:
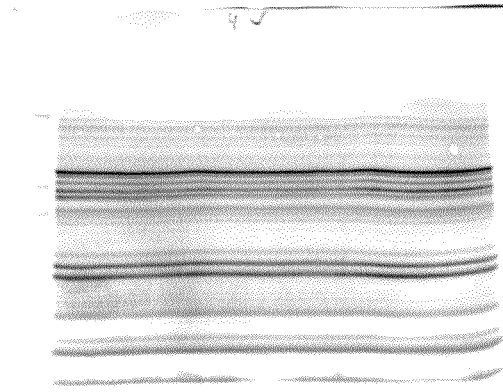
Figure 26E:
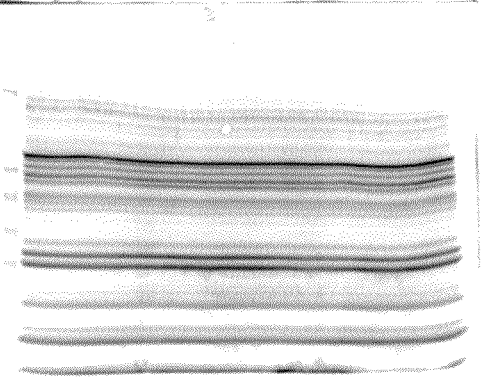
Figure 28A:
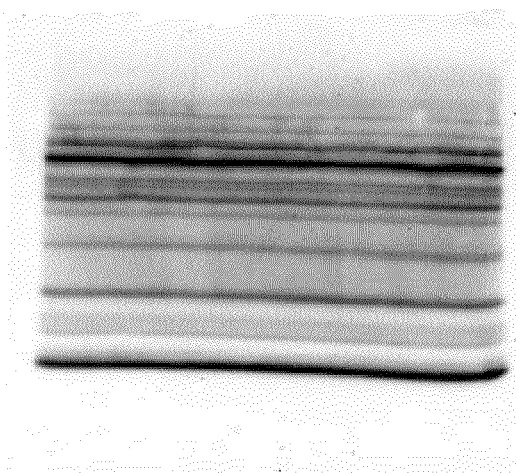
FIGS. 28A & 28B shows the results of the western blots performed as described in Examples 12A and 12B.
Figure 28B:
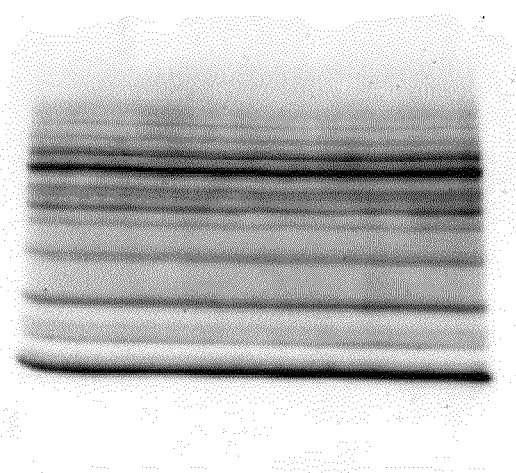

Four western blots were performed using an embodiment of the automated processing device as shown in FIGS. 1C & 1D and an embodiment of the bioprocessing cartridge as shown in FIGS. 12, 13A-B and 14, the results (FIGS. 26B-26E) were compared to a manual method (FIG. 26A) as follows:

Reagents and Equipment
NuPAGE® LDS Sample Buffer (Invitrogen cat #NP0007)
NuPAGE® MES SDS Running Buffer (Invitrogen cat #NP0002)
NuPAGE® Reducing Agent (Invitrogen cat #NP0004)
SeeBlue® Plus2 Prestained Standard (Invitrogen cat #LC5925)
NuPAGE® Antioxidant (Invitrogen cat #NP0005)
Gels=NuPAGE® 4-12% BT IPG Well (Invitrogen cat #NP0330BOX)
iBlot Gel Transfer Device (Invitrogen cat #IB1001)
iBlot Regular Transfer Stack—Mini (nitrocellulose) (Invitrogen cat #1B3010-02)

WesternBreeze® Chromogenic Kit—Anti Rabbit (Invitrogen cat #WB7105)
Rabbit anti-*E. coli* antibody (Dako cat #B0357)
Protocol
1. Western blot preparation: Five blots were prepared as follows: 4 µg of an *E. coli* lysate were prepared in NuPAGE® LDS sample buffer and 5 µl SeeBlue® Plus2 standard and were loaded onto NuPAGE® 4-12% BT IPG well format gels and run at 200V for 34 minutes. The proteins on the gels were then individually transferred onto nitrocellulose membranes (iBlot Regular Transfer Stack) using an iBlot Gel Transfer Device.
2. Immunodetection reagent preparation: Blocker, wash buffer and primary antibody diluent were prepared using reagents contained in the WesternBreeze® kit as described in the user manual provided with the kit. The Dako anti-*E. coli* primary antibody was diluted 1:1000 in primary antibody diluent. The secondary antibody used was the ready to use alkaline phosphatase conjugated goat anti-rabbit antibody contained in the WesternBreeze® kit. Sufficient reagents were prepared in one batch to process five blots—four using the automated instrument and one blot using the manual method.
3. Automated Instrument: Four sets of the following reagents were loaded into an embodiment of the tray of the automated instrument as shown in FIG. 6: blocker, rinse (water), Primary antibody, Wash (WesternBreeze® wash buffer), Secondary Antibody, Wash (WesternBreeze® wash buffer—a second aliquot), rinse (water—a second aliquot). Four bioprocessing cartridges were inserted into individual slots in the instrument. Four blots from step 1 above were individually loaded into separate blot holders according to the embodiment of the blot holder as shown FIG. 21A and were inserted into the bioprocessing cartridges within the instrument. The WesternBreeze® incubation protocol that is pre-programmed into the instrument was used for processing of these blots. All four blots in the instrument were processed by the instrument simultaneously using the pre-programmed WesternBreeze® Protocol.
4. Automated Protocol: The following steps were performed using the automated instrument and manually substantially as described in more detail in Examples 1-2 above:
 a. Block: 1×30 minutes—WesternBreeze® blocker
 b. Rinse: 2×5 minutes—Water
 c. Primary Antibody: 1×60 minutes—1:1000 rabbit anti-*E. coli* antibody in Primary antibody diluent
 d. Wash: 4×5 minutes—WesternBreeze® wash buffer
 e. Secondary Antibody: 1×30 minutes—WesternBreeze® goat anti-rabbit AP conjugate
 f. Wash: 4×5 minutes—WesternBreeze® wash buffer
 g. Rinse: 3×2 minutes—Water
5. Visualization: After the incubation steps above were completed, all blots were rinsed with water and incubated in chromogenic substrate (from WesternBreeze kit) for 20 minutes and imaged in the Fuji Luminometer (3 minute exposure). Results are shown in FIGS. 26A-26E.

D. Examples 10A-B and 11A-B

Western blots were performed using an embodiment of the automated processing device as shown in FIGS. 1C & 1D and an embodiment of the bioprocessing cartridge as shown in FIGS. 12, 13A-B and 14, the results (FIGS. 27A and 27C) of which were compared to a manual method (FIGS. 27B and 27D) as follows:

Reagents and Equipment
NuPAGE® LDS Sample Buffer (Invitrogen cat #NP0007)
NuPAGE® MES SDS Running Buffer (Invitrogen cat #NP0002)
NuPAGE® Reducing Agent (Invitrogen cat #NP0004)
SeeBlue® Plus2 Prestained Standard (Invitrogen cat #LC5925)
NuPAGE® Antioxidant (Invitrogen cat #NP0005)
Gels=NuPAGE® 4-12% BT IPG Well (Invitrogen cat #NP0330BOX)
iBlot Transfer Device (Invitrogen cat #IB1001)
iBlot Transfer Stack—Mini (nitrocellulose) (Invitrogen cat #1B3010-02)
Novex® ECL Chemiluminescent Substrate Reagent Kit— (Invitrogen cat #WP200005)
Rabbit anti-*E. coli* antibody (Dako cat #B0357)
Goat Anti-Rabbit IgG—HRP Conjugate (Jackson Labs cat #111-035-003)
Pierce ECL (Thermo 32109)
Protocol
1. Western Blot Preparation: 4 µg of an *E. coli* lysate were prepared in NuPAGE LDS sample buffer and 3 µl SeeBlue® Plus2 standard and were loaded onto a NuPAGE 4-12% BT ZOOM IPG well format gel and run at 200V for 34 minutes. The proteins were then transferred onto a 0.2 µm nitrocellulose membrane (FIGS. 27A and 27B) or a 0.2 µm PVDF (FIGS. 27C and 27D) membranes from the iBlot Regular Transfer Stacks using an iBlot Gel Transfer Device according to the instructions in the user's manual provided with the device.
2. Immunodetection reagent preparation: The following reagents were used:
 a. Blocker=5% non-fat dry milk (NFDM) in phosphate buffered saline with 0.1% Tween 20 (PBST).
 b. Wash buffer=PBST
 c. Primary Antibody Solution=1:1000 dilution of Dako anti-*E. coli* primary antibody in PBST.
 d. Secondary 2° Ab Solution=1:5000 dilution of Jackson HRP conjugated goat anti-rabbit IgG antibody in PBST.
3. Blot Processing: The membranes (after transfer) described in section 1 above were cut in half, one half of each were used for immunodetection performed in the automated instrument, the other half of each was processed using the same reagents and the standard manual procedure as described in the WesternBreeze® Chromogenic Kit user manual in a Falcon dish provided with the kit.
4. Automated Instrument: The following reagents were loaded into an embodiment of the tray of the automated instrument as shown in FIG. 6: blocker, rinse (water), Primary antibody, Wash (wash buffer), Secondary Antibody, Wash (wash buffer—second aliquot), rinse (water—a second aliquot). The individual halves of the membranes were run separately as follows: a bioprocessing cartridge was inserted into a slot of the instrument, the half of the blot membrane was loaded into an embodiment of a blot holder as shown FIG. 21B (made from die cut PVC film) and inserted into the bioprocessing chamber of the bioprocessing cartridge in the instrument.
5. Automated Protocol: The following steps were performed using the automated instrument (FIGS. 27A and 27C) and manually (FIGS. 27B and 27D) substantially as described in more detail in Examples 1-2 above:
 a. Block: 1×30 minutes
 b. Rinse: 2×5 minutes
 c. Primary Antibody: 1×60 minutes
 d. Wash: 4×5 minutes e. Secondary Antibody: 1×30 minutes f. Wash: 4×5 minutes g. Rinse: 3×2 minutes 6. Visualization: Visualization was performed substantially as described in Examples 3-4 above. The results are shown in FIGS. 27A-27D.

E. Examples 12A & 12B

Two western blots were performed using an embodiment of the automated processing device as shown in FIGS. 1C & 1D and an embodiment of the bioprocessing cartridge as shown in FIGS. 12, 13A-B and 14:

1. Western blot preparation: Two blots were prepared as follows: 4 μg of an *E. coli* lysate were prepared in NuPAGE LDS sample buffer and 3 μl SeeBlue® Plus2 standard and were loaded onto a NuPAGE 4-12% BT ZOOM IPG well format gel and run at 200V for 34 minutes. The proteins were then transferred onto 0.2 μm PVDF membranes from the iBlot Regular Transfer Stacks using an iBlot Gel Transfer Device according to the instructions in the user's manual provided with the device.

2. Immunodetection reagent preparation: Blocker, wash buffer and primary antibody diluent were prepared using reagents contained in the WesternBreeze® Chromogenic Kit as described in the user's manual provided with the kit. The Dako anti-*E. coli* primary antibody was diluted 1:1000 in primary antibody diluent. The secondary antibody used was the ready to use alkaline phosphatase conjugated goat anti-rabbit antibody contained in the WesternBreeze® Chromogenic Kit. Sufficient reagents were prepared in one batch to process both blots.

3. Automated Instrument: Two sets of the following reagents were loaded into an embodiment of the tray of the automated instrument as shown in FIG. 6: blocker, rinse (water), Primary antibody, Wash (WesternBreeze® wash buffer), Secondary Antibody, Wash (WesternBreeze® wash buffer—a second aliquot), rinse (water—a second aliquot). The two blot membranes were inserted into separate blot holders according to the embodiment of the blot holder as shown in FIG. 22B and were inserted into the bioprocessing chambers of the bioprocessing cartridges in the instrument.

4. Both blots were processed using the automated instrument substantially as described in more detail in Examples 1-2 using the following protocol:

a. Block: 1×10 minutes—WesternBreeze® blocker b. Primary Antibody: 1×30 minutes—1:1000 rabbit anti-*E. coli* antibody in antibody diluent c. Wash: 2×1 minutes and 2×5 minutes—WesternBreeze® wash buffer d. Secondary Antibody: 1×30 minutes—WesternBreeze® goat anti-rabbit AP conjugate e. Wash: 2×5 minutes—WesternBreeze® wash buffer f. Rinse: 3×1 minutes—Water 5. Visualization: After the incubation steps above were completed, both blots were rinsed with water and incubated in chemiluminescent substrate and imaged in the Fuji Luminometer (3 minute exposure). The results are shown in FIG. 28A-D.

F. Examples 13A & B

Two western blots were performed using an embodiment of the automated processing device as shown in FIGS. 1C & 1D and an embodiment of the bioprocessing cartridge as shown in FIGS. 12, 13A-B and 14:

1. Western blot preparation: Two blots were prepared as follows: 4 μg of an *E. coli* lysate were prepared in NuPAGE LDS sample buffer and 3 μl SeeBlue® Plus2 standard and were loaded onto a NuPAGE 4-12% BT ZOOM IPG well format gel and run at 200V for 34 minutes. The proteins were then transferred onto a 0.45 μm nitrocellulose membrane (Example 13A) or a 0.45 μm PVDF membrane (Example 13B) using the method described in the NuPAGE Bi-Tris Gel Instruction Booklet using 10% methanol and 1:1000 dilution of antioxidant.

2. Immunodetection reagent preparation: The following reagents were used:

a. Blocker=5% non-fat dry milk (NFDM) in Tris buffered saline (Thermo Scientific) with 0.1% Tween 20 (TBST).

b. Wash buffer=TBST c. Primary Antibody Solution=1:1000 dilution of Dako anti-*E. coli* primary antibody in TBST.

d. Secondary 2° Ab Solution=1:5000 dilution of Jackson HRP conjugated goat anti-rabbit IgG antibody in TB ST.

3. Automated Instrument: Two sets of the reagents were loaded into an embodiment of the tray of the automated instrument as shown in FIG. 6. Two blot membranes cartridges were inserted into separate blot holders according to the embodiment of the blot holder as shown in FIG. 22B and were inserted into the bioprocessing chambers of the bioprocessing cartridges in the instrument.

Figure 29A:
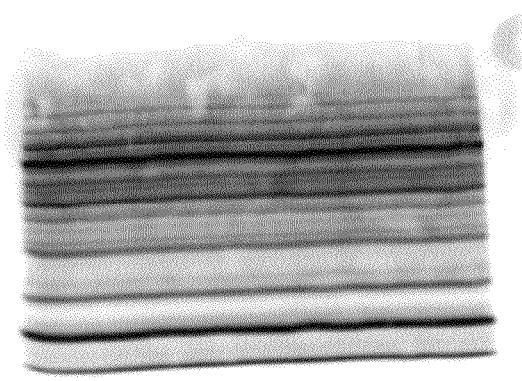
FIGS. 29A & 29B shows the results of the western blots performed as described in Examples 13A and 13B.
Figure 29B:
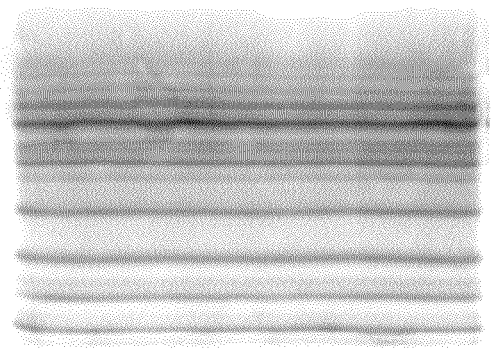

4. Automated Protocol: Both blots were processed using the automated instrument substantially as described in more detail in Examples 1-2 above using the following protocol:

a. Block: 1×60 minutes b. Wash: 2×1 minutes c. Primary Antibody: 1×60 minutes d. Wash: 2×1 minutes, 1×15 minutes and 2×5 minutes e. Secondary Antibody: 1×60 minutes f. Wash: 2×1 minutes, 1×15 minutes and 2×5 minutes 5. Visualization: Visualization was performed substantially as described in Examples 3-4 above. The results are shown in FIGS. 29A and 29B.

G. Examples 14A & B

Two western blots were performed using an embodiment of the automated processing device as shown in FIGS. 1C & 1D and an embodiment of the bioprocessing cartridge as shown in FIGS. 12, 13A-B and 14:

1. Western blot preparation: Two blots were prepared as follows: 4 μg of an *E. coli* lysate were prepared in NuPAGE LDS sample buffer and 3 μl SeeBlue® Plus2 standard and were loaded onto a NuPAGE 4-12% BT ZOOM IPG well format gel and run at 200V for 34 minutes. The proteins were then transferred onto 0.2 μm nitrocellulose (Example 14A) and 0.2 μm PVDF (Example 14B) membranes from the iBlot Regular Transfer Stacks using an iBlot Gel Transfer Device according to the instructions in the user's manual provided with the device.

2. Immunodetection reagent preparation: Blocker, wash buffer and primary antibody diluent were prepared using reagents contained in the WesternBreeze® Chromogenic Kit as described in the user's manual provided with the kit. The Dako anti-*E. coli* primary antibody was diluted 1:1000 in primary antibody diluent. The secondary antibody used was the ready to use alkaline phosphatase conjugated goat anti-rabbit antibody contained in the WesternBreeze® Chromogenic Kit. Sufficient reagents were prepared in one batch to process both blots.

3. Automated Instrument: Two sets of the following reagents were loaded into an embodiment of the tray of the automated instrument as shown in FIG. 6: blocker, rinse (water), Primary antibody, Wash (WesternBreeze® wash buffer), Secondary Antibody, Wash (WesternBreeze® wash buffer—a second aliquot), rinse (water—a second aliquot). The two blot membranes were inserted into separate blot holders according to the embodiment of the blot holder as shown in FIG. 22B and were inserted into the bioprocessing chambers of the bioprocessing cartridges in the instrument.

Figure 30A:
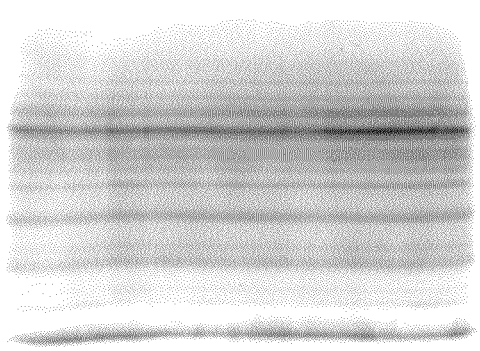
FIGS. 30A & 30B shows the results of the western blots performed as described in Examples 14A and 14B.
Figure 30B:
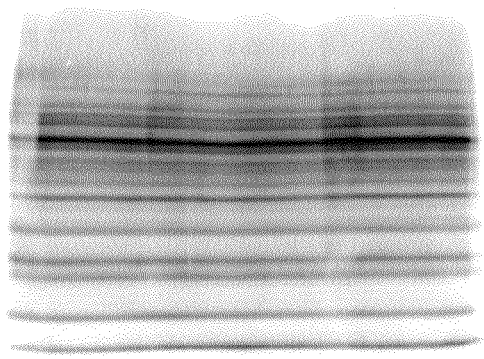

4. Automated Protocol: Both blots were processed using the automated instrument substantially as described in more detail in Examples 1-2 above using the following protocol:
 a. Block: 1×10 minutes—WesternBreeze® blocker
 b. Primary Antibody: 1×30 minutes—1:1000 rabbit anti-*E. coli* antibody in antibody diluent
 c. Wash: 2×1 minutes and 2×5 minutes—WesternBreeze® wash buffer
 d. Secondary Antibody: 1×30 minute—WesternBreeze® goat anti-rabbit AP conjugate
 e. Wash: 2×5 minutes—WesternBreeze® wash buffer
 f. Rinse: 3×1 minutes—Water 5. Visualization: After the incubation steps above were completed, both blots were rinsed with water and incubated in chemiluminescent substrate for 5 minutes and imaged in the Fuji Luminometer (3 minute exposure). The results are shown in FIGS. 30A and 30B.

H. Examples 15A-B and 16A-B

Western blots were performed using an embodiment of the automated processing device as shown in FIGS. 1C & 1D and an embodiment of the bioprocessing cartridge as shown in FIGS. 12, 13A-B and 14, the results (FIGS. 31A and 31C) of which were compared to a manual method (FIGS. 31B and 31D) as follows:

1. Western blot preparation: Two blots were prepared as follows: 4 µg of an *E. coli* lysate were prepared in NuPAGE LDS sample buffer and 3 µl SeeBlue® Plus2 standard and were loaded onto a NuPAGE 4-12% BT ZOOM IPG well format gel and run at 200V for 34 minutes. The proteins were then transferred onto a 0.2 µm nitrocellulose membrane (FIGS. 31C & 31D) or a 0.2 µm PVDF (FIGS. 31A & 31B) membrane from the iBlot Regular Transfer Stacks using an iBlot Gel Transfer Device according to the instructions in the user's manual provided with the device.

2. Immunodetection reagent preparation: Blocker, wash buffer and primary antibody diluent were prepared using reagents contained in the WesternBreeze® Chromogenic Kit as described in the user's manual provided with the kit. The Dako anti-*E. coli* primary antibody was diluted 1:1000 in primary antibody diluent. The secondary antibody used was the ready to use alkaline phosphatase conjugated goat anti-rabbit antibody contained in the WesternBreeze® Chromogenic Kit. Sufficient reagents were prepared in one batch to process both the blots processed with the automated instrument and the blots processed using the manual method (see below).

3. Blot Processing: The membranes (after transfer) described in section 1 of this example were cut in half, one half of each used for an immunodetection performed in the automated instrument, the other half of each was processed using the standard manual procedure as described in the WesternBreeze® Chromogenic Kit user manual in a Falcon dish provided with the kit.

4. Automated Instrument: For each automated processing, the following reagents were loaded into an embodiment of the tray of the automated instrument as shown in FIG. 6: blocker, rinse (water), Primary antibody, Wash (WesternBreeze® wash buffer), Secondary Antibody, Wash (WesternBreeze® wash buffer—a second aliquot), rinse (water—a second aliquot). A bioprocessing cartridge was inserted into a slot of the instrument, the half of the relevant blot membrane was loaded into an embodiment of a blot holder as shown FIG. 22B and inserted into the bioprocessing chamber of the bioprocessing cartridge in the instrument.

5. Automated Protocol: The following steps were performed using the automated instrument (the results of which are shown in FIGS. 31A and 31C) and manually (the results of which are shown in FIGS. 31B and 31D). For the automated processing, the reagents were recirculated in the bioprocessing chamber of the bioprocessing cartridge using the channel associated with the process valve 1440 in FIG. 14 using the following protocol:
 a. Block: 1×30 minutes
 b. Rinse: 2×5 minutes
 c. Primary Antibody: 1×60 minutes
 d. Wash: 4×5 minutes
 e. Secondary Antibody: 1×30 minutes
 f. Wash: 4×5 minutes
 g. Rinse: 3×2 minutes 6. Visualization: After the incubation steps above were completed, the blots were rinsed with water and incubated in chemiluminescent substrate for 5 minutes and imaged in the Fuji Luminometer (3 minute exposure). The results are shown in FIGS. 31A-31D.

Examples 17A-B and 18A-B

Western blots were performed using an embodiment of the automated processing device as shown in FIGS. 1C & 1D and an embodiment of the bioprocessing cartridge as shown in FIGS. 12, 13A-B and 14 as follows:

1. Western blot preparation: Two blots were prepared as follows: 4 µg of an *E. coli* lysate were prepared in NuPAGE LDS sample buffer and 3 µl SeeBlue® Plus2 standard and were loaded onto a NuPAGE 4-12% BT ZOOM IPG well format gel and run at 200V for 34 minutes. The proteins were then transferred onto a 0.2 µm PVDF membrane from the iBlot Regular Transfer Stacks using an iBlot Gel Transfer Device according to the instructions in the user's manual provided with the device.

2. Blot Processing: The membranes (after transfer) described in section 1 of this example were cut in half, one half of each blot was used for an immunodetection performed in the automated instrument, the results of which are shown in FIGS. 32A and 32C and manually, the results of which are shown in FIGS. 32B and 32D, using the NFDM/TBST reagents (FIGS. 32C and 32D) described in Examples 13A-B or the NFDM/PBST reagents (FIGS. 32A and 32B) described in Examples 10A-B and 11A-B.

3. Automated Instrument: For each automated processing, the reagents were loaded into an embodiment of the tray of the automated instrument as shown in FIG. 6: a bioprocessing cartridge was inserted into a slot of the instrument, the half of the relevant blot membrane was loaded into an embodiment of a blot holder as shown FIG. 22B and inserted into the bioprocessing chamber of the bioprocessing cartridge in the instrument.

4. Automated Protocol: The following steps were performed using the automated instrument (the results of which are shown in FIGS. 32C and 32D) and manually (the results of which are shown in FIGS. 32A and 32B). For the automated processing, the reagents were recirculated in the bioprocessing chamber of the bioprocessing cartridge using the channel associated with the process valve 1440 in FIG. 14 using the following protocol:
 a. Block: 1×30 minutes
 b. Rinse: 2×5 minutes
 c. Primary Antibody: 1×60 minutes
 d. Wash: 4×5 minutes
 e. Secondary Antibody: 1×30 minutes
 f. Wash: 4×5 minutes
 g. Rinse: 3×2 minutes
 5. Visualization: Visualization was performed substantially as described in Examples 3-4. The results are shown in FIGS. 32A-32D.

For each of Examples J-M, the following Bovine Serum Albumin (BSA) samples were prepared (separately for each Example) and loaded onto NuPage 4-12% BT 10 mini well mini gels for BSA blots and run at 200V for approximately 34 minutes:
 5 μl of Sharp Prestained Standard (Invitrogen Cat #LC5800)
 8 μl of Magic Mark XP Western Protein Standard (Invitrogen Cat #LC5602)
 50 ng of BSA (5 μl of 10 ng/μl BSA) (BSA-Sigma Cat #A-3059)
 25 ng of BSA (5 μl of 5 ng/μl BSA)
 10 ng of BSA (5 μl of 2 ng/μl BSA)

J. Examples 19A & 19B

Two western blots were performed using an embodiment of the automated processing device as shown in FIGS. 1C & 1D and an embodiment of the bioprocessing cartridge as shown in FIGS. 12, 13A-B and 14, the results (FIG. 33B) of which were compared to the results (FIG. 33A) of a manual method as follows:

1. Western blot preparation: One set of BSA samples as described above were loaded and prepared as described above. The proteins were then transferred onto a 0.2 μm nitrocellulose membrane from the iBlot Regular Transfer Stacks using an iBlot Gel Transfer Device according to the instructions in the user's manual provided with the device.

2. Immunodetection reagent preparation: Blocker, wash buffer and primary antibody diluent were prepared using reagents contained in the WesternBreeze® Chromogenic Kit as described in the user's manual provided with the kit. The Dako anti-*E. coli* primary antibody was diluted 1:1000 in primary antibody diluent. The secondary antibody used was the ready to use alkaline phosphatase conjugated goat anti-rabbit antibody contained in the WesternBreeze® Chromogenic Kit. Sufficient reagents were prepared in one batch to process both blots.

Figures 33A, 33B:
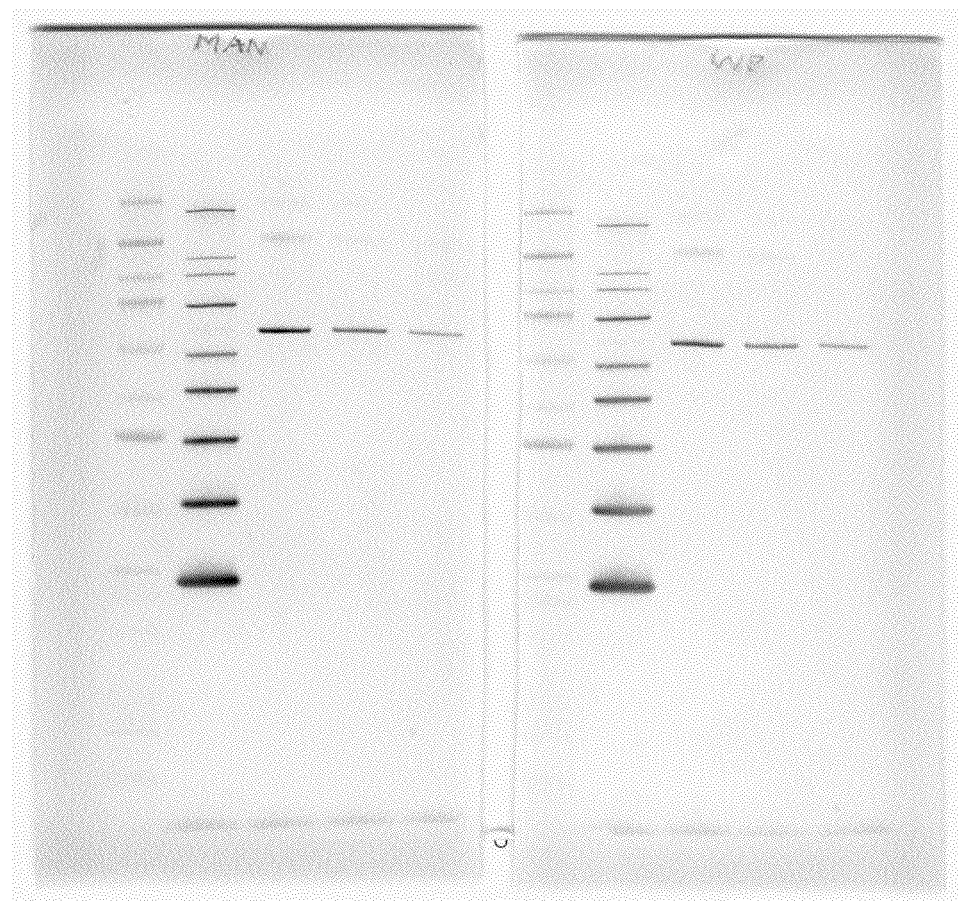
FIGS. 33A & 33B shows the results of the western blots performed as described in Examples 19A and 19B.

3. Blot Processing: The membrane (after transfer) described in section 1 above was cut in half, one half of each was used for an immunodetection performed in the automated instrument (as shown in FIG. 33B), the other half of was processed using the standard manual procedure as described in the WesternBreeze® Chromogenic Kit user manual in a Falcon dish provided with the kit (as shown in FIG. 33A).

4. Automated Instrument: For the automated processing, the following reagents were loaded into an embodiment of the tray of the automated instrument as shown in FIG. 6: blocker, rinse (water), Primary antibody, Wash (WesternBreeze® wash buffer), Secondary Antibody, Wash (WesternBreeze® wash buffer—a second aliquot), rinse (water—a second aliquot). A bioprocessing cartridge was inserted into a slot of the instrument, the half of the blot membrane was loaded into an embodiment of a blot holder as shown FIG. 22B and inserted into the bioprocessing chamber of the bioprocessing cartridge in the instrument.

5. Automated Protocol: The following steps were performed using the automated instrument (the results of which are shown in FIG. 33B) using the following protocol:
 a. Block: 1×30 minutes
 b. Rinse: 2×5 minutes
 c. Primary Antibody: 1×60 minutes
 d. Wash: 4×5 minutes
 e. Secondary Antibody: 1×30 minutes
 f. Wash: 4×5 minutes
 g. Rinse: 3×2 minutes 6. Visualization: After the incubation steps above were completed, both blots were rinsed with water and incubated in chemiluminescent substrate and imaged in the Fuji Luminometer (3 minute exposure). The blots were then rinsed and then incubated with chromogenic substrate for 20 minutes, rinsed, allowed to dry somewhat and then imaged using an Epson 4990 scanner. The results for the chromogenic imaging are shown in FIGS. 33A and 33B. The Loads from left to right are—5 μl Sharp Prestained Marker, 8 μl of 1:10 dilution of MagicMark, BSA (50 ng, 25 ng, 10 ng).

K. Examples 20A & 20B

Figure 34A:
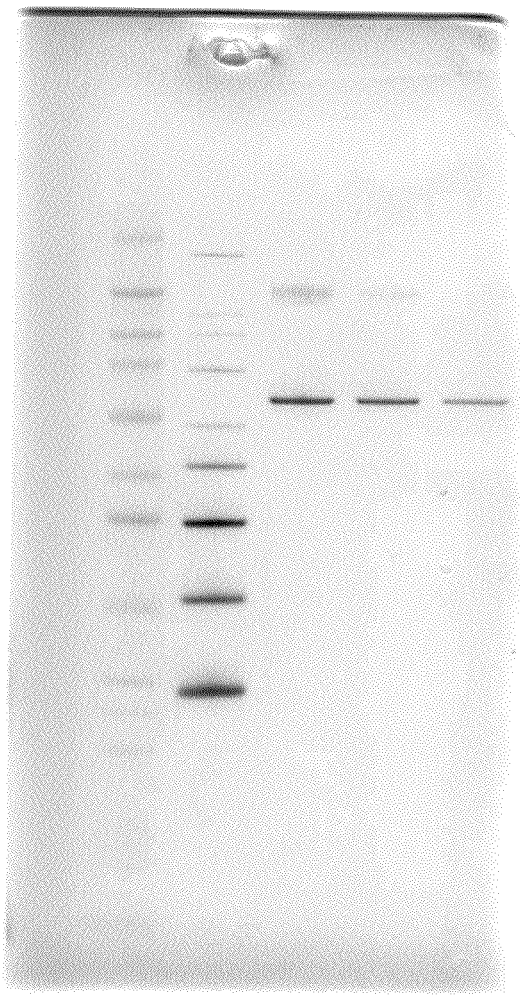
FIGS. 34A & 34B shows the results of the western blots performed as described in Examples 20A and 20B.
Figure 34B:
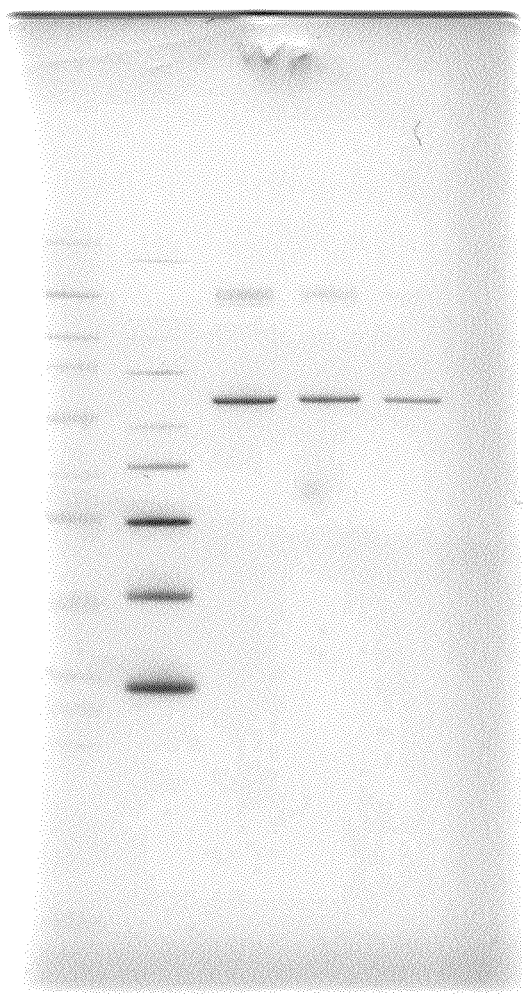

Two western blots were performed using an embodiment of the automated processing device as shown in FIGS. 1C & 1D and an embodiment of the bioprocessing cartridge as shown in FIGS. 12, 13A-B and 14 (the results of which are shown in FIG. 34B) and manually (the results of which are shown in FIG. 34A) substantially the same as in Examples 19A-B with the exception that the proteins were transferred onto a 0.2 μm PVDF membrane. The results for the chromogenic imaging are shown in FIGS. 34A & 34B. The Loads from left to right are—5 μl Sharp Prestained Marker, 8 μl of 1:10 dilution of MagicMark, BSA (50 ng, 25 ng, 10 ng).

L. Examples 21A & 21B

Two western blots were performed using an embodiment of the automated processing device as shown in FIGS. 1C & 1D and an embodiment of the bioprocessing cartridge as shown in FIGS. 12, 13A-B and 14, the results (FIG. 35A) of which were compared to the results (FIG. 35B) obtained using a manual method:

1. Western blot preparation: One set of BSA samples as described above were loaded and prepared as described above. The proteins were then transferred onto a 0.2 μm nitrocellulose membrane from the iBlot Regular Transfer Stacks using an iBlot Gel Transfer Device according to the instructions in the user's manual provided with the device.

Figures 35A, 35B:
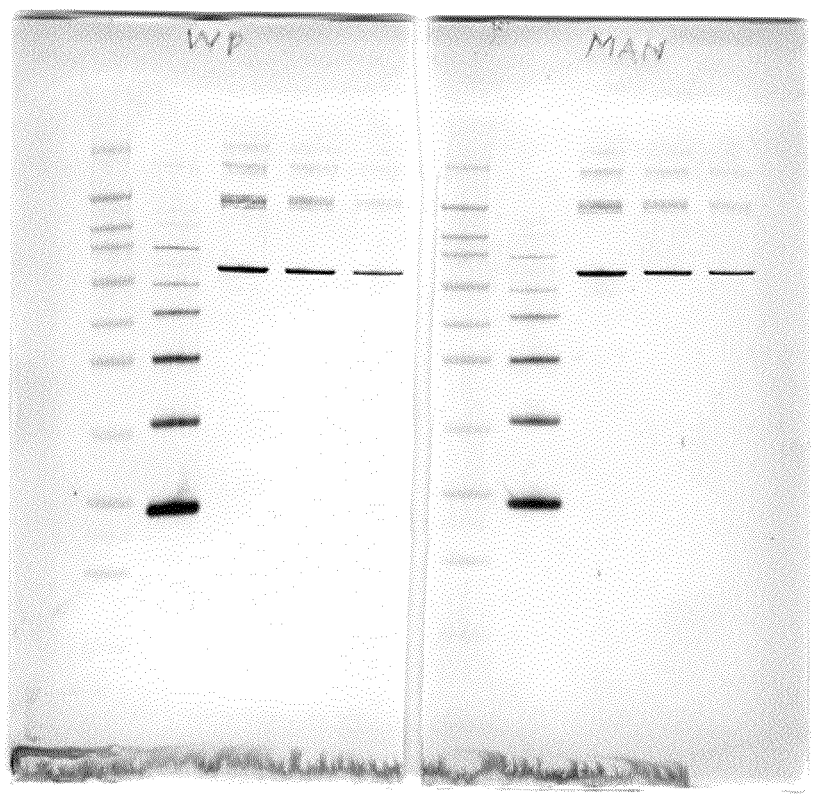
FIGS. 35A & 35B shows the results of the western blots performed as described in Examples 21A and 21B.

2. Blot Processing: The membrane (after transfer) described in section 1 of this example above was cut in half, one half of the blot was used for an immunodetection performed in the automated instrument (used as shown in FIG. 35A) and manually (used as shown in FIG. 35B) using the NFDM/TBST reagents described in Examples 13A-B.

3. Automated Instrument: For the automated processing, the reagents were loaded into an embodiment of the tray of the automated instrument as shown in FIG. 6: A bioprocessing cartridge was inserted into a slot of the instrument, the half of the blot membrane was loaded into an embodiment of a blot holder as shown FIG. 22B and inserted into the bioprocessing chamber of the bioprocessing cartridge in the instrument.

4. Automated Protocol: The following steps were performed using the automated instrument (the results shown in FIG. 35B) and manually (the results shown in FIG. 35A):
   a. Block: 1×60 minutes
   b. Wash: 2×1 minutes
   c. Primary Antibody: 1×60 minutes
   d. Wash: 2×1 minutes, 1×15 minutes and 2×5 minutes
   e. Secondary Antibody: 1×60 minutes
   f. Wash: 2×1 minutes, 1×15 minutes and 2×5 minutes 5. Visualization: After the incubation steps above were completed, both blots were rinsed with water and incubated in HRP chemiluminescent substrate and imaged in the Fuji Luminometer (3 minute exposure). The blots were then rinsed and then incubated with TMB HRP chromogenic substrate for 20 minutes, rinsed, allowed to dry somewhat and then imaged using an Epson 4990 scanner. The results for the chromogenic imaging are shown in FIG. 33. The Loads from left to right are—5 µl Sharp Prestained Marker, 8 µl of 1:10 dilution of MagicMark, BSA (50 ng, 25 ng, 10 ng).

M. Examples 22A & 22B

Figure 36A:
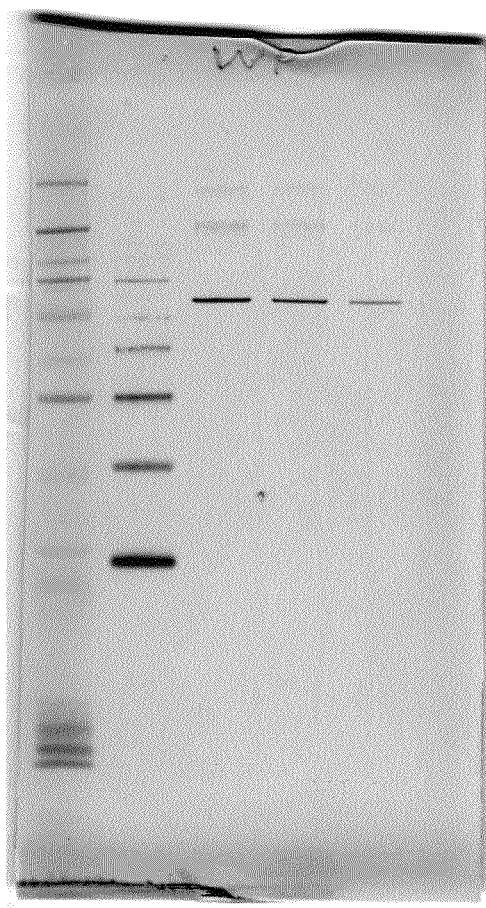
FIGS. 36A & 36B shows the results of the western blots performed as described in Examples 22A and 22B.
Figure 36B:
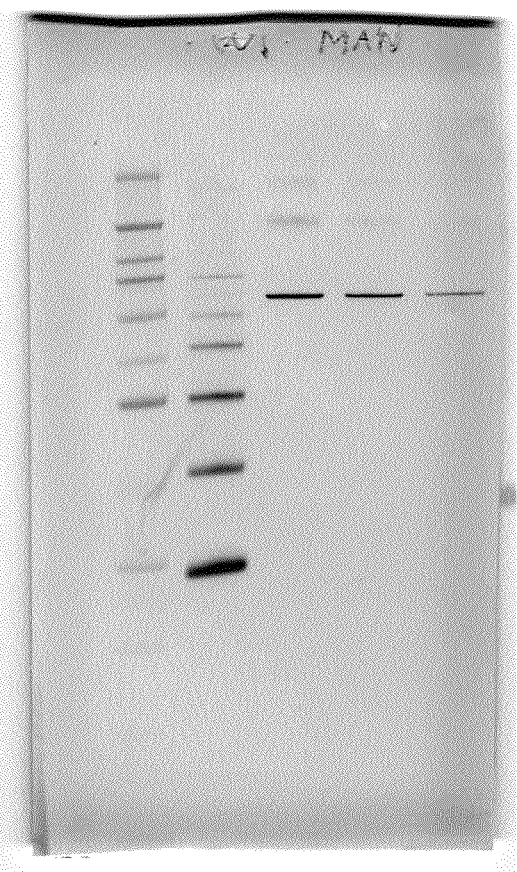

Two western blots were performed using an embodiment of the automated processing device as shown in FIGS. 1C & 1D and an embodiment of the bioprocessing cartridge as shown in FIGS. 12, 13A-B and 14, the results (FIG. 36A) of which were compared to the results (FIG. 36B) obtained using a manual method substantially the same as in Examples 19A-B with the exception that for the automated processing the reagents were recirculated in the bioprocessing chamber of the bioprocessing cartridge using the channel associated with the process valve 1440 in FIG. 14. The results for the chromogenic imaging are shown in FIG. 34. The Loads from left to right are—5 µl Sharp Prestained Marker, 8 µl of 1:10 dilution of MagicMark, BSA (50 ng, 25 ng, 10 ng).

Unless explicitly noted in the example, for Examples N-W all of the fluids, solutions, reagents, mixtures, waste, or any other fluid products of the example, were pumped/moved using the cartridge by drawing the fluid up into the cartridge using an aspiration/expiration tube, access valve, and pump located on the card. Additionally, during some steps of the examples, the fluid may be passed through a membrane/bioprocessing chamber located in the cartridge after being drawn up into the cartridge and before being expelled out of the cartridge.

N. Examples 23

Figure 37:
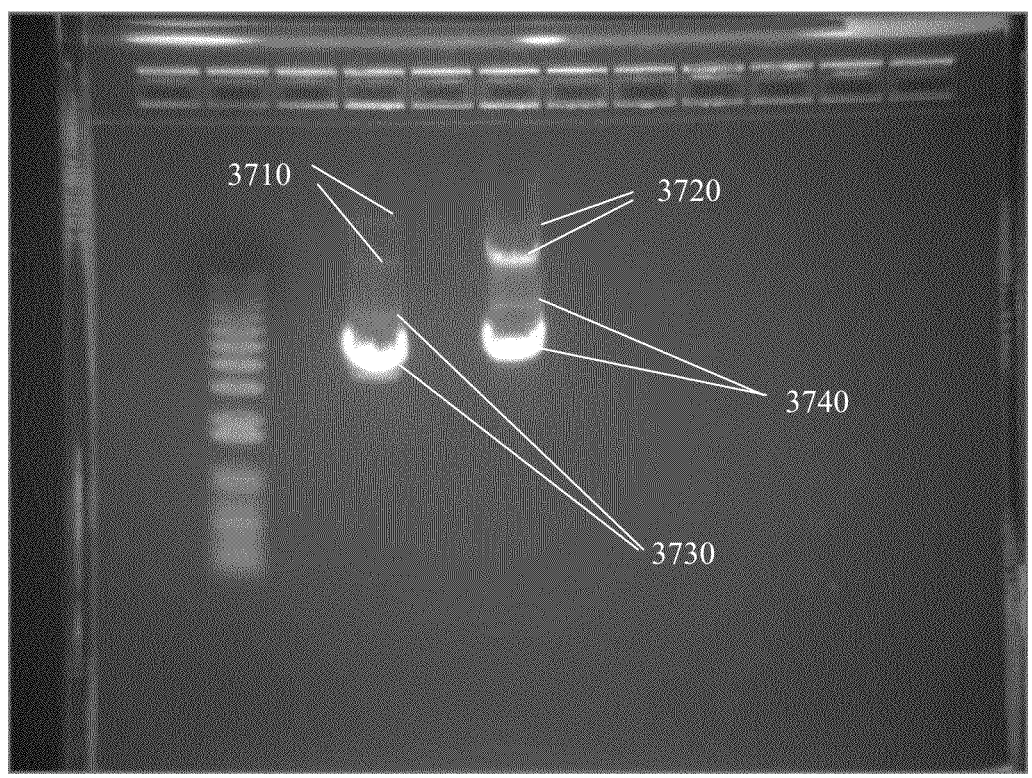
FIG. 37 shows the results of the nucleic acid purification performed as described in Example 23.

Nucleic acid purification was performed using the automated processing device shown in FIGS. 1A & 1B, and the cartridge shown in FIGS. 16-18, the results of which are shown in FIG. 37. The amount of genomic DNA collected using the described protocol varied depending on whether a flow diffuser was incorporated with the device. The amount of genomic DNA was decreased by using a flow diffuser during pumping of the lysed cell mixture from the lysis buffer reservoir to the resuspension buffer/RnaseA buffer mixture reservoir during the resuspension and lysing of cells. The amount of genomic DNA 3710 detected using a system incorporating a flow diffuser was less than the amount of genomic DNA 3720 detected using a system without a flow diffuser. However, the amount of plasmid DNA detected using both devices 3730, 3740 remained of comparable value.

1. Cell Capture: 250 mL of *E. Coli* containing media was aspirated into the bioprocessing cartridge from a sample reservoir located outside the bioprocessing cartridge and passed through a bioprocessing chamber containing a B1a065 membrane. The cells were filtered from the media and the clarified media passed out of the cartridge into a waste reservoir. 20 PSI of air pressure was then applied to the inlet side of the B1a065 cell capture membrane to move residual media from the membrane and out of the cartridge and into the waste reservoir.

2. Resuspension and lysing of cells: RnaseA solution was aspirated into the cartridge from an outside reagent reservoir, pumped out of the cartridge into a reagent reservoir containing a resuspension buffer, and the RnaseA and resuspension buffer mixed together by the cartridge. The resuspension buffer/RnaseA mixture was then aspirated into the cartridge through the membrane to remove cells captured by the capture membrane. The cells were removed from the capture membrane and passed out of the cartridge into a reagent reservoir containing a lysis buffer. Approximately ¾ amount of the lysed cell mixture was then pumped from the lysis buffer reservoir back to the resuspension /RnaseA buffer mixture reservoir. 32 PSI of air pressure was then applied through the outlet side of the cell capture membrane to remove the remaining captured cells to the lysis buffer reservoir. The remaining captured cells were then pumped from the lysis buffer reservoir to the resuspension/RnaseA mixture reservoir.

3. Neutralization—Neutralization buffer was then pumped from the neutralization buffer reservoir to the reservoir containing the lysed cells. The lysed cells/neutralization buffer solution was then pumped back into the lysis buffer reservoir. The device then pauses for three minutes to allow cell debris layer and clear lysate phase layer to separate.

4. Clarification/Binding—Cell debris was then clarified by pumping the cell debris layer from the reservoir into the cartridge and through an Extra-Thick (Xthick) glass fiber clarification membrane and Anion Exchange DNA binding membrane and out of the cartridge and into the waste reservoir. An anion exchange wash buffer was then pumped from the anion exchange wash buffer reservoir into the cartridge, through the membrane, and out to the waste reservoir. 32 PSI of air pressure was then applied through the anion exchange membrane to ensure all waste was collected from the membrane into the waste container. An anion exchange elution buffer was then pumped from the anion exchange elution buffer into the cartridge, through the membrane, and out of the bioprocessing cartridge and into a reagent reservoir containing isopropyl alcohol, to precipitate the pDNA. The elution buffer/isopropyl alcohol buffer solution was then mixed by pumping the mixture back into the anion exchange elution buffer reservoir. The elution buffer/isopropyl alcohol buffer solution was then mixed one more time by pumping the mixture back from the anion exchange elution buffer reservoir back into the isopropyl alcohol reservoir. The elution buffer/isopropyl alcohol mixture was then passed through a PPTR membrane (B1a065) to capture the precipitated pDNA. The remainder of the mixture was then passed out of the cartridge and into the waste reservoir. 70% ETOH was then pumped from the ETOH reagent reservoir into the cartridge, through the PPTR membrane, and out to the waste reservoir. The membrane was then air dried by passing 32 PSI of air through the membrane for 1.5 minutes and any waste passed out of membrane collected by the waste reservoir. A final TE elution buffer was then pumped from the TE elution buffer reservoir through the PPTR membrane, and out to a collection tube. The amount of genomic DNA detected using a device with a diffuser is compared to a device not using a diffuser as shown in FIG. 37.

O. Example 24

Nucleic acid can be purified and captured using a bioprocessing system described in FIGS. 1A & 1B and the protocol below. As opposed to Example 23, Example 24 includes partial flow diffused pumping stems, and premixed the lysis and resuspension buffers together prior to cell resuspension.

1. Cell capture—250 mL of *E. Coli* containing media was aspirated into the bioprocessing cartridge from a disposable cell liner reservoir located outside the bioprocessing cartridge and passed through a bioprocessing chamber containing a B1a065 membrane. The cells were filtered from the media and the clarified media passed out of the cartridge into a waste reservoir.

2. Resuspension and lysing of cells—RnaseA solution was aspirated into the cartridge from a reagent reservoir, passed out of the cartridge and into a reagent reservoir containing a resuspension buffer. Lysis buffer was then pumped from the lysis buffer reservoir into reservoir containing the resuspension buffer and the RnaseA. The lysis/resuspension/RnaseA mixture was then aspirated into the cartridge through the membrane to remove and lyse cells from the cell capture membrane before collected into an external reservoir. The remaining cells are then pumped from the external into a second reservoir.

3. Neutralization—Neutralization buffer was pumped from the neutralization buffer reservoir to a separate reservoir. The cells from the second reservoir described above are then pumped into the reservoir containing the neutralization buffer. The automated system paused for three minutes to allow the cell debris phase and the clear lysate phase to separate.

Figure 38:
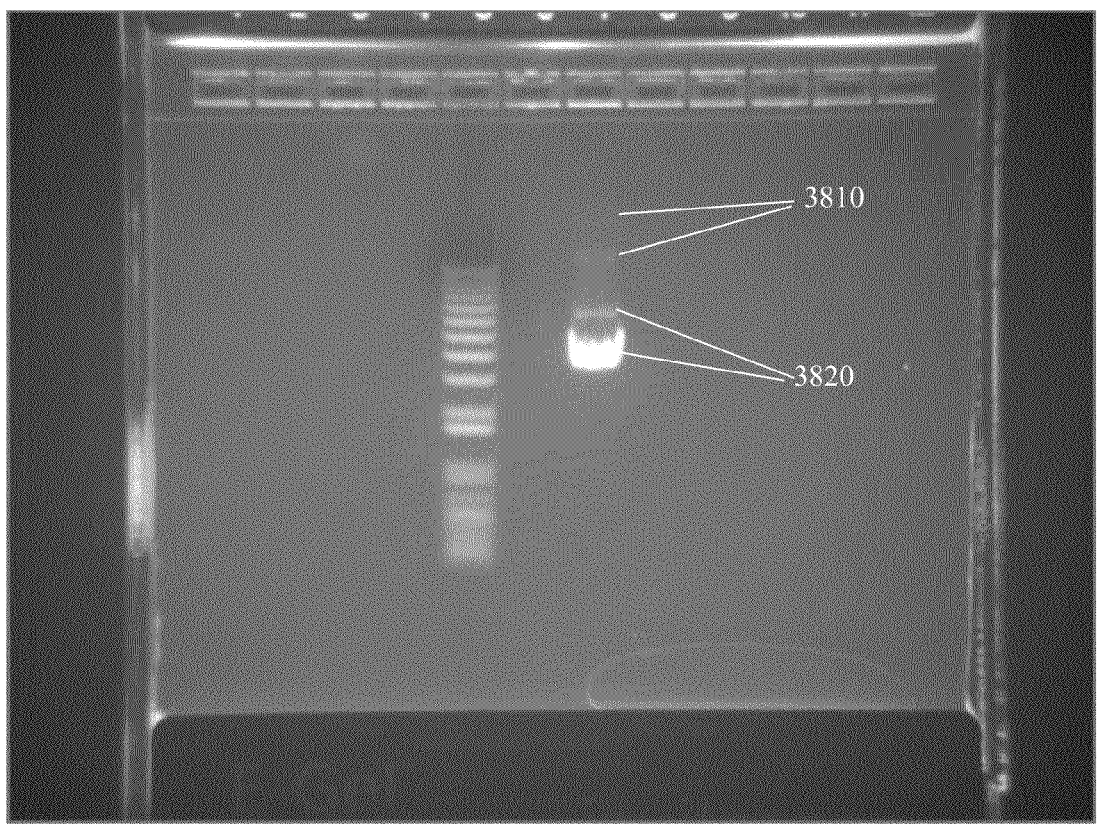
FIG. 38 shows the results of the nucleic acid purification performed as described in Example 24.

4. Clarification/Binding—The cell debris was then clarified by using a diffuser pump to pump the neutralized cell material from the reservoir through an Extra-Thick glass fiber clarification membrane and an Anion Exchange DNA binding membrane and out to the waste reservoir. An anion exchange wash buffer was then pumped from the anion exchange wash buffer reservoir through the membrane and out to the waste reservoir. 32 PSI of air was then applied through the anion exchange membrane and out to the waste reservoir. An anion exchange elution buffer is then pumped from the anion exchange elution buffer reservoir through the membrane and out a reservoir containing isopropyl alcohol, where the pDNA is precipitated. The elution buffer and the isopropyl alcohol was then mixed by the cartridge transferring the mixture from the isopropyl alcohol reservoir to a second reservoir and then back to the isopropyl alcohol reservoir. The elution buffer/isopropyl alcohol mixture containing the precipitated pDNA was then pumped through the bioprocessing chamber containing a PPTR membrane to capture the DNA. The remainder of the media is transferred to waste. 70% ETOH was then pumped from the ETOH reservoir through the PPTR membrane and out to the waste reservoir. The membrane was then air dried with 32 PSI of air for 1.5 and any material released from the PPTR membrane collected in the waste reservoir. A final TE elution buffer was then pumped from the TE elution buffer reservoir through the PPTR membrane and collected in a collection tube. The DNA collected is shown in FIG. 38. The amount of genomic DNA 3810 and plasmid DNA 3820 detected are indicated.

P. Example 25

Nucleic acid can be purified and captured using a bioprocessing system described in FIGS. 1A & 1B, and the bioprocessing cartridge shown in FIGS. 16-18, where the automated system is configured with varying pump speed and step timing.

1. Cell capture—250 mL of *E. Coli* containing media was aspirated into the bioprocessing cartridge from a disposable cell liner reservoir located outside the bioprocessing cartridge and passed through a bioprocessing chamber containing a B1a065 membrane. The cells were filtered from the media and the clarified media passed out of the cartridge into a waste reservoir. The system operates with an 800 ms pump delay between each stroke of the pump for a 21 minute capture time.

2. Resuspend and lyse cells—RnaseA solution is pumped from the RnaseA solution reservoir into the resuspension buffer reservoir using an 800 ms pump delay between each pump stroke for 5 seconds. The resuspension buffer and RnaseA is then pumped back into the RnaseA solution reservoir and then back to the resuspension buffer reservoir using an 800 ms pump delay between each pump stroke for 2 seconds. The resuspension/RnaseA buffer is then pumped through the cartridge into the lysis buffer reservoir using an 800 ms pump delay between each pump stroke for 1 minute. The RnaseA/resuspension/lysis buffer is then mixed by transporting the solution through the card from the lysis buffer reservoir into the resuspension/RnaseA buffer reservoir at using an 800 ms pump delay between each pump stroke for 1 minute. The lysis/resuspension/RnaseA mixture is then pumped through the membrane where the cells captured on the cell capture membrane are removed from the membrane and lysed and then transported to the lysis/resuspension/RnaseA reagent reservoir. The pumping is done using 800 ms pump delay between each pump stroke for 1 minute and 45 seconds. The lysis mixture with lysed cells is then pumpled from to the lysis buffer reagent reservoir using a 1100 ms pump delay between each pump stroke for 1 minute and 45 seconds.

3. Neutralization—The lysed cells are then pumped from the lysis buffer reagent reservoir to the neutralization buffer reagent reservoir using an 1100 ms pump delay between each pump stroke for 1 minute and 45 seconds. The solution is then pumped using a diffuser from the neutralization reservoir to the lysis mixture reservoir using a 2500 ms pump delay between each pump stroke for 4 and a half minutes. The device is then paused for 4 minutes to allow cell debris and clear lysate phases to separate.

Figure 39:
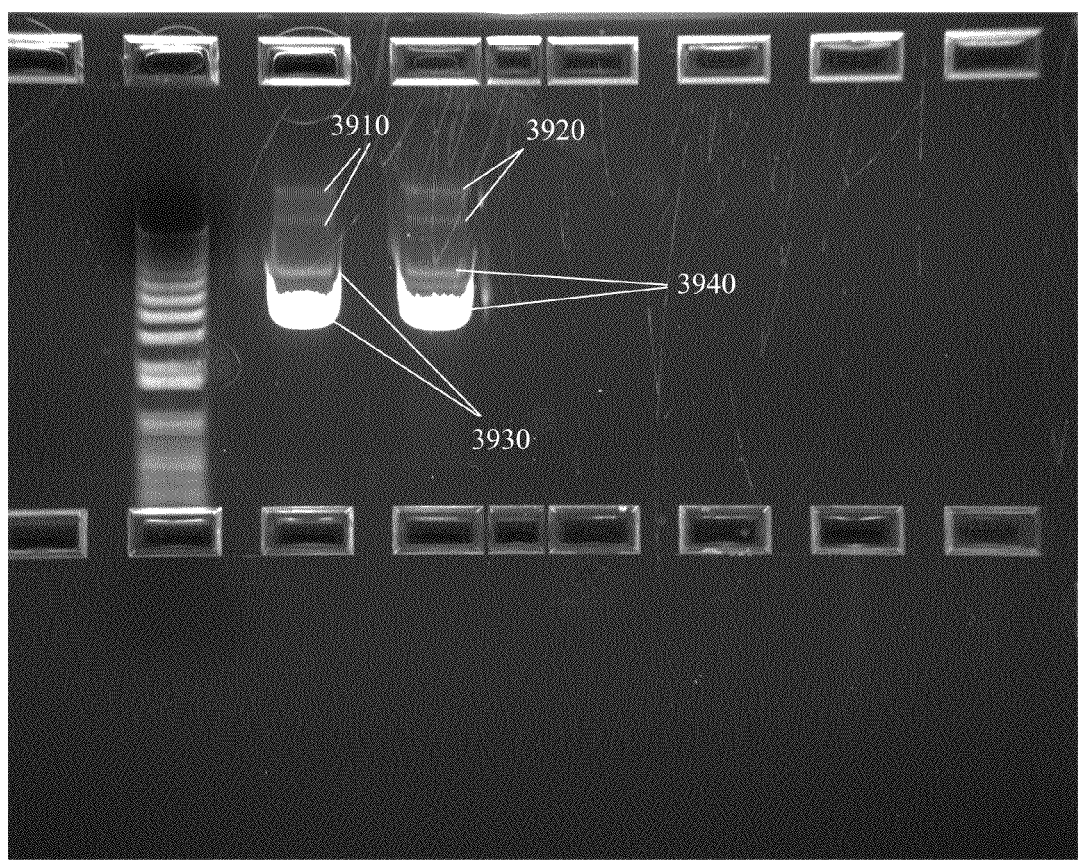
FIG. 39 shows the results of the nucleic acid purification performed as described in Example 25.

4. Clarification/Binding—The cell debris was then clarified using a diffuser pump to pump the cell debris and clear lysate phases through an Extra-Thick glass fiber clarification membrane and then through an Anion Exchange DNA binding membrane and then to the waste reservoir using a 2500 ms delay between each pump stroke for 5 minutes and 30 seconds. An Anion exchange wash buffer solution was then pumped from the Anion exchange wash buffer reservoir through the Anion exchange membrane and out to the waste reservoir using 1100 ms delay between each pump stroke for 30 seconds. 32 PSI of air pressure was then applied through the anion exchange membrane to pass debris from the membrane into the waste reservoir. 2 seconds after the air pressure application was ceased, an anion exchange elution buffer was then pumped through the membrane and out to the isopropyl alcohol reagent reservoir using a pump between each pump stroke with 1100 ms delay for 30 seconds. The elution buffer and the isopropyl alcohol buffer was then mixed by transferring the mixture to a second reservoir and then back to the isopropyl alcohol buffer reservoir using a 1100 ms delay between each pump stroke for 45 seconds. The waste lines were then purged using 32 PSI of air pressure with any waste in the waste lines passing out to the waste reservoir. Two seconds after air pressure application was ceased, the valves were opened to release pressure. The system was then paused for 1 minute to allow precipitation to occur. The elution buffer/isopropyl alcohol mixture containing the precipitated pDNA was then passed through a PPTR membrane (b1a065)

to capture the DNA and the remainder of the mixture was passed out to the waste reservoir using a 1100 ms delay between each pump stroke for 1 minute. 70% ETOH was then aspirated into the cartridge from the ETOH reservoir and passed through the PPTR membrane and then out to waste using a pump with 1100 ms delay between each pump stroke for 25 seconds. Residual ETOH was removed from the line by applying 32 PSI of air pressure to the membrane. The system was paused for 1 second. The membrane was then air dried by applying 32 PSI of air pressure through a check valve and out to waste for 1.5 minutes. A TE elution buffer was then applied through the PPTR to elute the pDNA into a collection tube using a 2000 ms delay between each pump stroke for 5 minutes. The amount of genomic DNA (gDNA) 3910, 3920 detected and the amount of plasmid DNA (pDNA) 3930, 3940 detected is shown in FIG. 39.

Q. Example 26

Nucleic acid can be purified and captured using a bioprocessing system described in FIGS. 1A & 1B and the bioprocessing cartridge shown in FIGS. 16-18, where the automated system is configured with varying pump speed and step timing. Nucleic acid purification using partial flow diffused pumping steps wherein the application of air pressure, premixing of lysis with resuspension buffer have been removed. The example also used the reagent reservoir tray as shown in FIGS. 8B-8F. This version of the protocol finalized the removal of genomic DNA (gDNA) contamination.

1. Capture cells—125 mL of *E. coli* media was aspirated into the cartridge from the disposable cell liner reservoir and passed through a B1a065 membrane of one of the bioprocessing chambers of the cartridge to filter cells from the media. The clarified media was the pumped out of the cartridge into the waste reservoir using 700 ms pump delay between pump strokes with 15 minutes capture time. Pressure was then released and the system paused for 1 second.

2. Resuspension and lysis of cells—RnaseA solution was pumped through the cartridge from the RnaseA reagent reservoir to the resuspension buffer reservoir using an 800 ms pump delay between pump strokes for 4 seconds. The resuspension buffer/RnaseA buffer mixture was then pumped to the lysis buffer reservoir using an 800 ms pump delay between pump strokes for 45 seconds. The lysis/resuspension/RnaseA mixture was then aspirated into the cartridge and passed through the cell capture membrane. The captured cells were then removed from the membrane and lysed and the lysed cells pumped into the resuspension/RnaseA buffer mixture reservoir using 800 ms pump delay between pump strokes for 1 minute and 20 seconds.

3. Neutralization—the lysed cell mixture was the pumped using a diffuser to a second reservoir and back to the original reservoir using a 2500 ms pump delay between pump strokes for 3 and a half minutes. The waste lines were then purged using a check valve to blow 32 PSI of air pressure in the cartridge for 2 seconds. The system was then paused for 30 seconds to allow cell debris and the clear lysate phases to separate.

Figure 40:
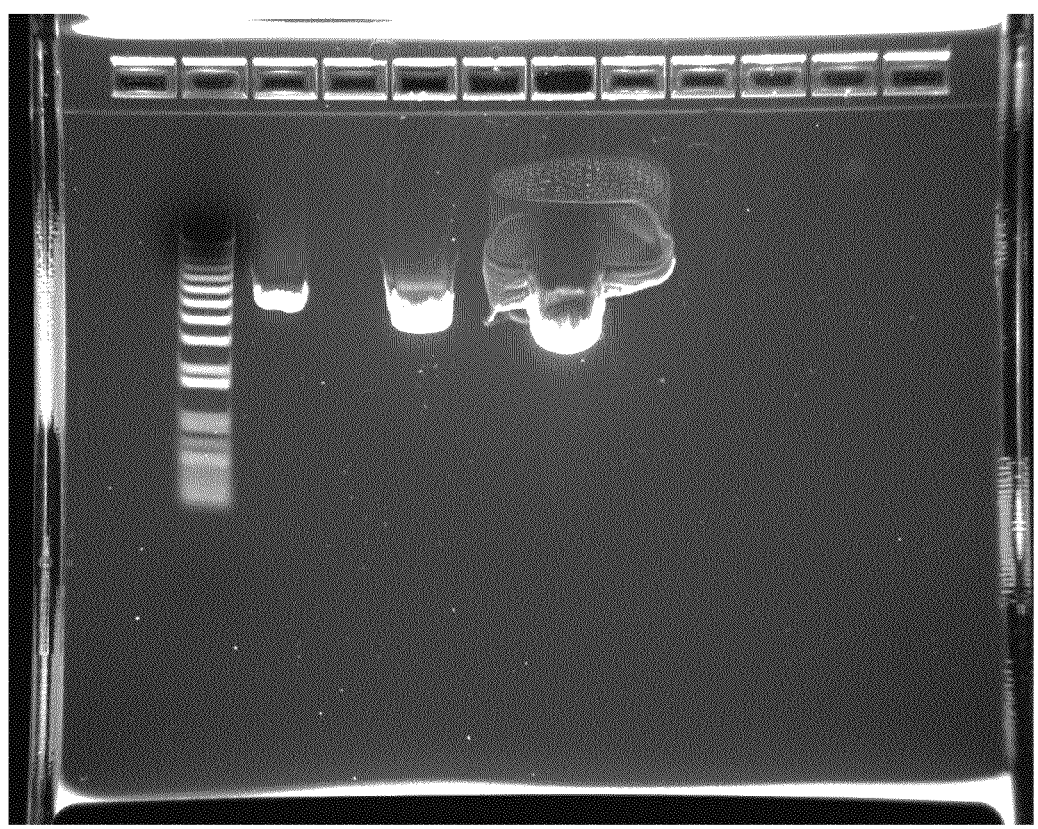
FIG. 40 shows the results of the nucleic acid purification performed as described in Example 26.

4. Clarification/Binding—The cell debris was clarified using a diffuser pump to pump the cell debris through an Extra-Thick glass fiber clarification membrane in one bioprocessing chamber and then pumped through an Anion Exchange DNA binding membrane in another bioprocessing chamber and then finally pumped into a waste reservoir using a 2500 ms delay between pump strokes for 8 and a half minutes. The remaining debris and buffer solution is then pumped to the waste container using a 2500 ms delay between pump strokes for 30 seconds. Any remaining mixture in the lysis buffer reservoir is then pumped to the waste container using a 2500 ms delay between pump strokes for 30 seconds. An Anion exchange wash buffer is pumped from Anion exchange wash buffer reagent reservoir through the Anion exchange membrane to remove the unwanted material out to the waste reservoir using an 800 ms delay between pump strokes for 15 seconds. An Anion exchange elution buffer was then pumped through the membrane to elute the captured DNA material out to an isopropyl alcohol reagent reservoir using an 1100 ms delay between pump strokes for 30 seconds. The elution buffer and isopropyl alcohol buffer are then mixed by transferring the mixture to a second reagent reservoir and then back to the isopropyl alcohol reagent reservoir using an 800 ms delay between pump strokes for 30 seconds. The waste lines were then purged using 32 PSI of atmospheric pressure, purging the waste to the waste reservoir for 1 second. The pressure was then released by opening several valve located along the waste lines. The system was then paused for 2 minutes to allow the pDNA in the mixture to precipitate. The elution buffer/isopropyl alcohol buffer mixture with precipitated DNA was then pumped through the PPTR membrane (b1a065) to capture the precipitated DNA while the remainder of the mixture flows out to waste using an 1100 ms delay between pump strokes for 1 minute. 70% ETOH was then pumped from the ETOH reagent reservoir through the PPTR membrane and out to waste. Residual ETOH was then removed from the line and out to waste by applying 32 PSI through the line for 1 second. The membrane was then air dried by applying 32 PSI of air through a check valve through the membrane and into a waste reservoir. A final TE elution buffer was applied through PPTR membrane to elute the precipitated DNA using a 3000 ms delay for 1 minute and 20 seconds. The amount of plasmid DNA 4010 detected is shown in FIG. 40.

R. Example 27

Protein expression can be identified using a bioprocessing system shown in FIGS. 1C & 1D and the bioprocessing cartridge shown in FIGS. 12-14. In some embodiments, a nitrocellulose membrane maybe used with the system, such as a Hybond nitrocellulose membrane, although any suitable membrane may be used with the system.

1. Samples: A 3T3-L1 primordial cell line was differentiated into adipocytes cells. Insulin was then added to some of the samples to stimulate pAKT expression. Each sample contained 10 ug differentiated 3T3 L1 adipocyte lysates.

2. Protocol: The samples were blocked for 60 minutes in a blocker, for example, SeaBlock/TBS/0.5% Tween 20. Any suitable blocker may be used including MILK, BSA, other serums, IVGs. The sample was then washed two times for one minute using a wash buffer, for example TBS/0.05% Tween 20. Any suitable wash buffer may be used including PBS. Additionally, the percentage of components in the wash buffer may be varied. The sample was then co-incubated in either 1/1000 AKT(rabbit) and pAKT (mouse) or Glut-4 (rabbit) and GADPH (moue) primary antibodies for at least 900 minutes, or overnight, in a SeaBlock/TBS/0.05% Tween 20 blocker. The sample was then washed three times for 5 minutes in a TBS/0.05% Tween 20 wash buffer. The samples were then co-incubated for 60 minutes in either 1 nM GAR-QDaot 625 and GAM-Qdot 800 or in 1 ug/mL GAR-AlexaFluor 790 (AF790) and GAM-AlexaFluor 680 (AF680) secondary conjugates in blocker containing 0.01% SDS. Any suitable label may be used including quantum dots (Qdot) nanocrystals, including QDots 625, 605, 655, 565, 585, 705, 800, and 525, and microspheres. In some embodiments, the primary conjugates may be Goat anti-Mouse IgG (GAM), Goat anti-Rabbit IgG (GAR), or streptavidin. In some embodiments, the sample may be conjugated to a Click-iT® label/imaging kit. In some embodiments, the secondary conjugate may be GAM, GAR, or streptavidin. The sample was then washed three times for 5 minutes in TB S/0.05% Tween 20 wash buffer. The sample was then rinsed in water two times for five minutes.

Figure 41C:
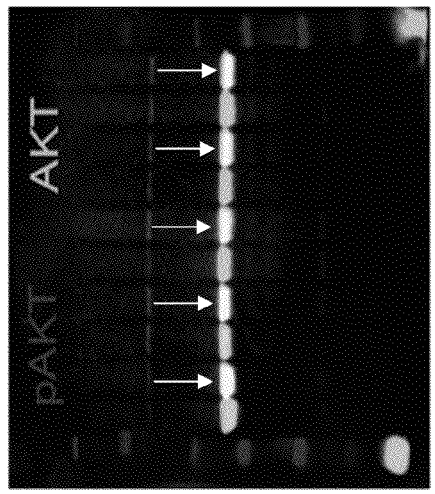
FIGS. 41A-41F show the results of the western blots performed as described in Example 27.
Figure 41F:
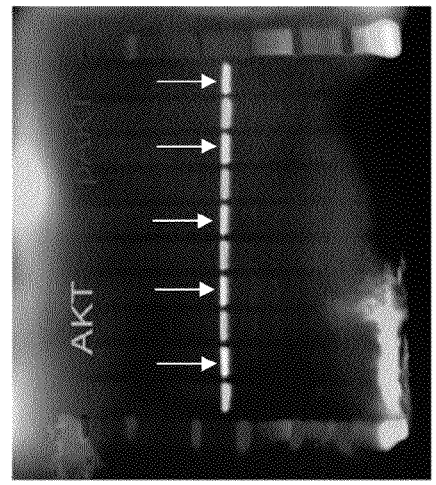
Figure 41B:
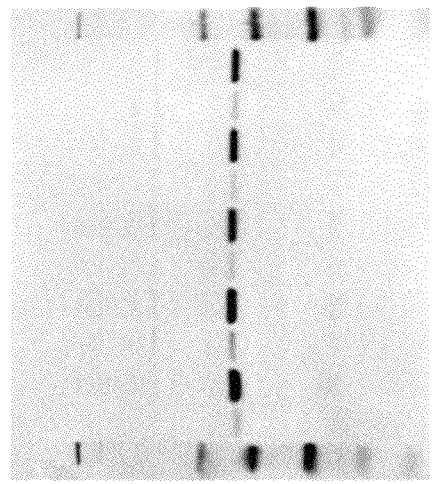
Figure 41E:
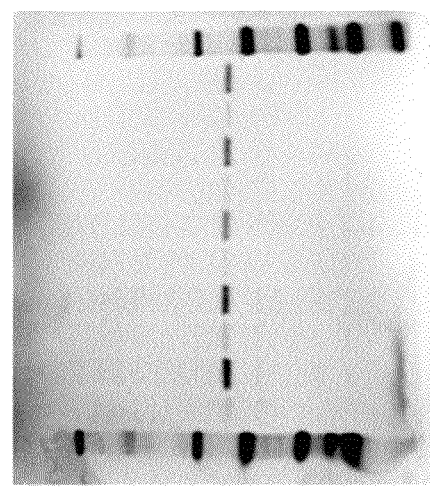
Figure 41A:
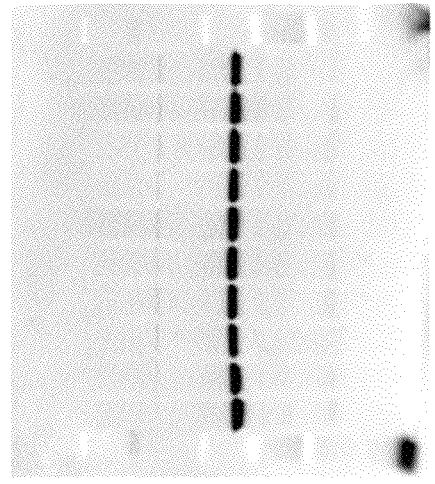
Figure 41D:
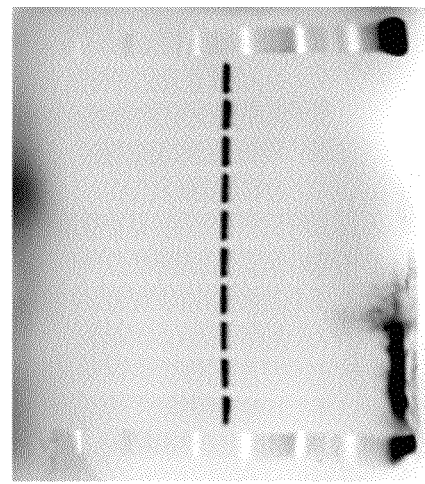

3. Results: The results of using Q-Dot® nanocrystals with the device described herein are shown in FIGS. 41A-41F, FIGS. 42A-42C, and FIGS. 43A-43F. FIGS. 41A-41F show the results obtained using the device described in FIGS. 1C & 1D. FIGS. 41A-41C illustrates the results obtained where the gel was done on the benchtop, whereas FIGS. 41D-41F show the results obtained using the device described herein. FIGS. 41A & 41D illustrate two gels run identifying the presence of AKT (rabbit) labeled with GAR-Qdot 625, FIGS. 41B & 41E illustrate two gels run detecting the presence of pAKT (mouse) +GAM-Qdot 800, and FIGS. 41C & 41F illustrate the merged results of gels shown in FIGS. 41A & 41B and FIGS. 41D & 41E, respectively. The arrows indicated the lanes in which both AKT and pAKT were detected.

Figure 42C:
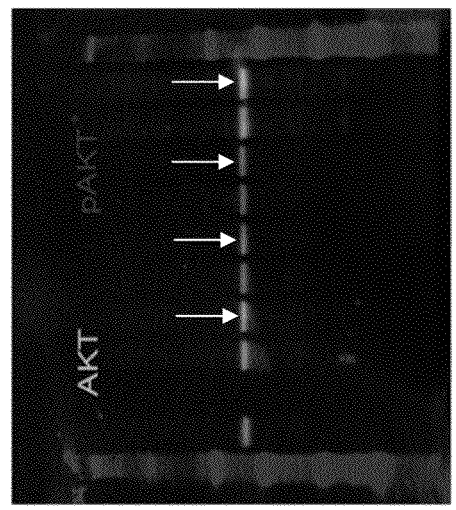
FIGS. 42A-42C show the result of the western blots performed as described in Example 27.
Figure 42B:
Figure 42A:
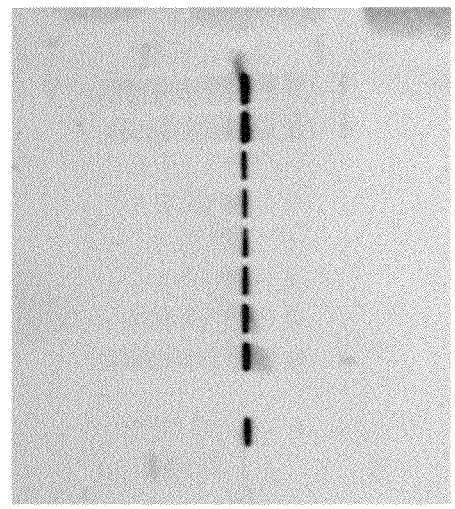

FIGS. 42A-42C show the results obtained using the device described in FIGS. 1C & 1D. FIG. 42A shows the presence of AKT (rabbit) wherein AKT has been labeled with GAR-AlexaFluor 790. FIG. 42B shows the presence of pAKT (mouse) wherein the pAKT has been labeled with GAM-AF680. FIG. 42C shows an image of the gels shown in FIGS. 42A & 42B. The arrows indicated the lanes in which both AKT and pAKT were detected.

Figure 43A:
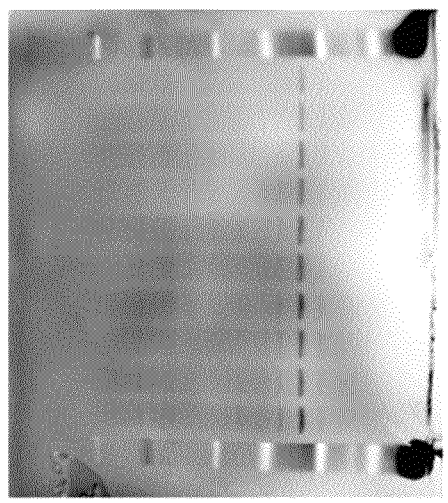
FIGS. 43A-43F show the result of the western blots performed as described in Example 27.
Figure 43B:
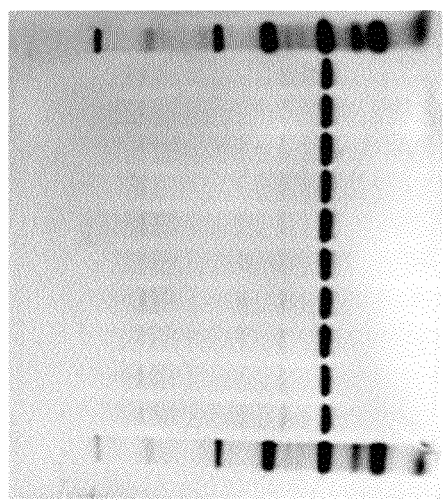
Figure 43C:
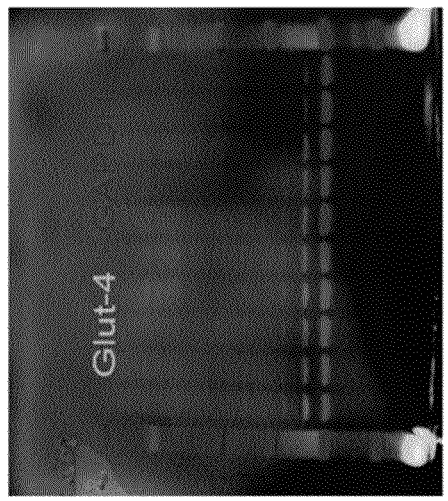
Figure 43D:
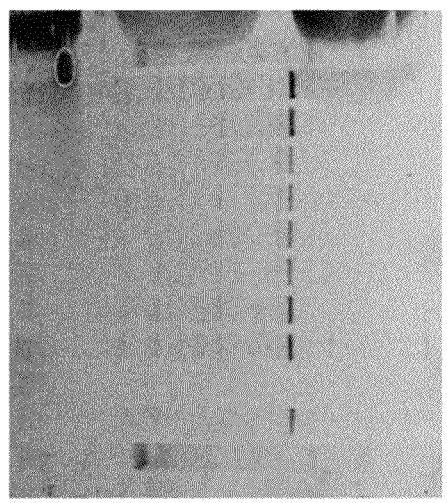
Figure 43E:
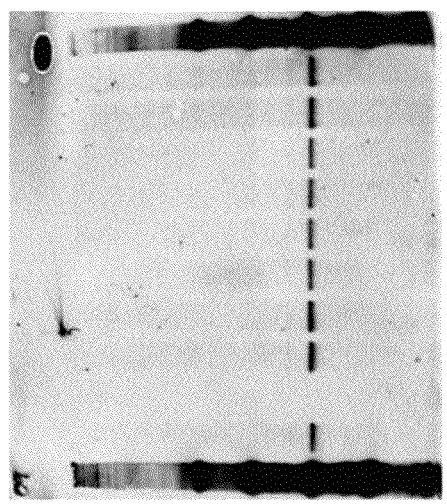
Figure 43F:
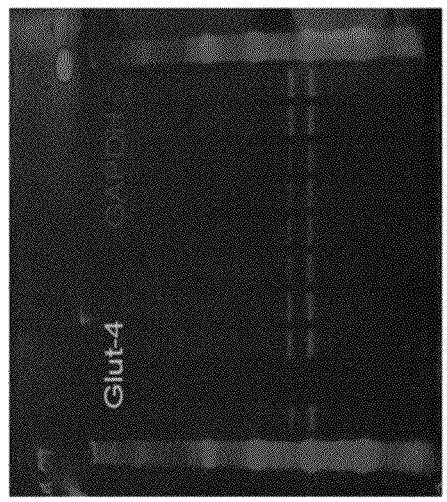

FIGS. 43A-43F shows the presence of different proteins in the adipocytes and, more particularly, the presence of the same amount of protein across the gel. The result of FIGS. 43A-43F can be used to compare how much sample was loaded in each well on the gel using either Qdots or AlexaFlour dyes. FIG. 43A shows the presence of Glut-4(rabbit) labeled with GAR-Qdot 625. FIG. 43B shows the presence of GADPH (mouse) labeled with GAM-Qdot 800. FIG. 43C shows the merged image of FIGS. 43A & 43B. FIG. 43D shows the presence of Glut-4(rabbit) labeled with GAR-AF 790. FIG. 43E shows the presence of GAPDH (mouse) labeled with GAM-AF680. FIG. 43F shows the merged image of FIGS. 43D & 43E.

S. Example 28

Food safety analysis may be performed using a bioprocessing system described in FIGS. 16-18. Contamination of food with pathogenic microorganisms is one of the major concerns in the food industry. Traditional culture methods for food safety pathogen detection are time consuming and may take greater than 24 hours to perform, from start to finish. Current requirements in food safety testing specify a rapid detection of a small number of bacteria, typically 1 cubic foot per 25 grams of a food sample, in less than 8 hours. These requirements make rapid detection of slow-growing bacteria challenging because of the low number of bacteria that may be present in the culture after a short (up to 6 hours) pre-enrichment step. The detection and identification of bacterial pathogens in food may be done with DNA analysis, however, extraction, purification, and recovery of a sufficient amount of bacterial DNA from large sample volumes may be a critical factor in these assays. Because of the relatively low number of pathogenic bacteria in a culture even after 8 hours of enrichment (typically 0.1-10 cfu/mL) recovering sufficient amounts of bacterial DNA for successful downstream PCR is essential. Insufficient numbers of DNA targets in PCR reactions can lead to high Ct values or no positive signal. Conventional concentrating techniques include techniques, such as centrifugation of large sample volumes (1 ml or more), co-precipitate bacteria, food sample particulates and other inhibitors typically present in the culture. Therefore, robust DNA-extraction protocols have to be used before PCR or other molecular techniques can be used. However, centrifugation of large volumes of culture enriched with pathogenic bacteria is associated with risks of damaging containers and as a result, severe contamination of equipment and work area. Using the device provided herein in FIGS. 1A & 1B and the bioprocessing cartridge shown in FIGS. 16-18, DNA can be prepared and extracted from a large sample volume using an automated method and device.

1. Sample preparation: a food matrix culture (10-50 mL) is applied to the prefilter (P). The pre-filter retains large size particulates and allows bacteria to flow through the filter. The flow-through, containing mostly bacteria is then directed to the second filter where the bacteria is then captured by the filter and the flow through discarded to waste. The bacteria captured by the second filter is then lysed on the second filter using a lysis solution, for example, PrepSeq lysis solution, and the lysate is directed to the silica membrane. The DNA from the lysed bacteria is captured by the silica membrane and the flow through is discarded to the waste reservoir. The silica membrane is then washed with PrepSeq wash solution to remove PCR inhibitors.

2. DNA collection: an elution buffer, for example PrepSeq elution buffer, is then pumped through the silica membrane to elute the DNA from the silica membrane. The amount of DNA eluted from the membrane may be between 40 uL-115 uL.

3. Results: using the bioprocessing device herein allows for the processing of extra-large volumes (>10 mL) of complex food sample cultures in a relatively short amount of time. The automated sample processing steps allow removing food particulates from the sample matrix and capturing bacterial DNA extractions using the silica membrane.

T. Example 29

Nucleic acid can be purified and captured using a bioprocessing system described in FIGS. 1A & 1B and the bioprocessing cartridge shown in FIGS. 16-18, where the automated system is configured with varying pump speed and step timing. Nucleic acid purification using partial flow diffused pumping steps wherein the application of air pressure, pre-mixing of lysis with resuspension buffer have been removed. The example also used the reagent reservoir tray as shown in FIGS. 8B-8F. This version of the protocol optimized the removal of genomic DNA (gDNA) contamination.

1. Cell Capture: 125 mL of *E. Coli* containing media was aspirated into the bioprocessing cartridge from a sample reservoir (disposable cell liner reservoir) located outside the bioprocessing cartridge and passed through a bioprocessing chamber containing a B1a065 membrane to filter cells from the media. The clarified media separated from the cells was pumped out of the cartridge into a waste reservoir. The sample was pumped through the bioprocessing chamber using a 700 ms pump delay for 15 min capture time. Pressure remaining in the cartridge was released for 1 second.

2. Cell Resuspension and Lysis: RnaseA solution was aspirated into the cartridge from an outside reagent reservoir and then pumped out of the cartridge into a reagent reservoir containing a resuspension buffer. The RnaseA solution was pumped using 800 ms pump delay for 4 seconds. The resuspension/RnaseA buffer mixture was then mixed together. The resuspension/RnaseA buffer mixture was then pumped from the buffer reservoir to the lysis buffer reservoir. The mixture was pumped using an 800 ms pump delay for 45 seconds. The lysis buffer/resuspension/RnaseA mixture was then pumped from the lysis buffer reservoir through the outlet side of the membrane to simultaneously remove and lyse cells from the cell capture membrane. Pumping the mixture through the outlet side of the membrane eliminated the need to use an air to remove the remaining cells captured cells. The mixture was pumped using an 800 ms pump delay for 1 minute and 20 seconds. The diffused lysis buffer/resuspension/RnaseA mixture was pumped from to the resuspension/RnaseA mixture reservoir using a 2500 ms pump delay for 3 minutes and 30 seconds.

3. Neutralization: The lysed cells were then pumped from a first reservoir to a second reservoir using a 2500 ms pump delay between each pump stroke for 3 minutes and 30 seconds. The mixture was then diffuse pumped from the second reservoir to a third reservoir using a 2500 ms pump delay between each pump stroke for 6 minutes and 40 seconds. The mixture was then diffuse pumped from the third reservoir back to the second reservoir using a 2500 ms pump delay for 5 minutes. The remainder of the mixture in the third reservoir was then diffuse pumped from the third reservoir back to the second reservoir using a 2500 ms pump delay for 5 minutes. The waste lines were then purged for 2 seconds using a check valve to apply 32 PSI of air. The device was then paused for 5 minutes to allow the cell debris and clear lysate phases to separate.

4. Clarification/Anion Exchange Binding: The cell debris was then clarified using a diffuser pump to pump the cell debris and clear lysate phases through an Extra-Thick glass fiber clarification membrane and then through an Anion Exchange DNA binding membrane and then to the waste reservoir using a 2500 ms delay for 10 minutes and 30 seconds. Remaining debris and buffer was removed using a 2500 ms delay for 1 minute. An anion exchange wash buffer was then pumped through the Anion exchange membrane and out to the waste reservoir using a 2500 ms delay for 40 seconds 5. Anion Exchange Elution and Precipitation: Anion exchange elution buffer was pumped from the buffer reservoir through the anion exchange membrane and out to a reservoir containing Isopropyl alcohol using an 1100 ms delay pump delay for 1 minute and 30 seconds. The elution buffer and isopropyl alcohol buffer mixture was then mixed by pumping the mixture from the isopropyl reservoir to the elution buffer reservoir using an 800 ms delay for 20 seconds and then back to the isopropyl alcohol reservoir using an 800 ms pump delay for 30 seconds. The waste lines were then purged to waste using 32 PSI of air pressure for 1 second. Pressure was then released by opening valves. The system was then paused for 2 minutes to allow for precipitation to occur 6. Capture of pDNA on Precipitator Membrane: The elution buffer/IPA mixture containing precipitated pDNA was diffuse pumped through PPTR membrane (b1a065) to capture DNA. The filtered buffers were pumped out to waste using a pump delay of 2500 ms for 4 minutes. 70% ETOH was then diffuse pumped from the ETOH reservoir through the PPTR membrane and then out to waste using a pump with a 2500 ms delay between pump strokes for 30 seconds. Residual ETOH was removed from the line by applying 32 PSI of air pressure for 1 second through valves and out to waste. The membrane was then air dried by applying 32 PSI of air through the check valve and out to waste for 1.5 minutes.

7. Final elution into collection tube: A TE elution buffer was then applied through the PPTR membrane to elute the pDNA into a collection tube using a 3000 ms delay between pump strokes for 5 minutes.

U. Example 30

Cell clumping and the effect of adding NaCl to alleviated cell clumping was tested using the protocol described in Example 29 above. The protocol was run using a bioprocessing system described in FIGS. 1A & 1B and the bioprocessing cartridge shown in FIGS. 16-18.

Using the protocol described in Example 29 above, 250 mM NaCl was added to 125 mL of cells located in the reagent tray. Overnight cultures were prepared by the addition of 50 uL of TOP10/DH10B-T1R glycerol stock solution to 1 L of fresh LB media containg 100 ug/ml Ampicillin. 125 mL of bacterial culture was poured into the reagent reservoir. NaCl (5M) was added to the reservoir prior to starting a run using the device to achieve the desired NaCl concentration.

Figure 44A:
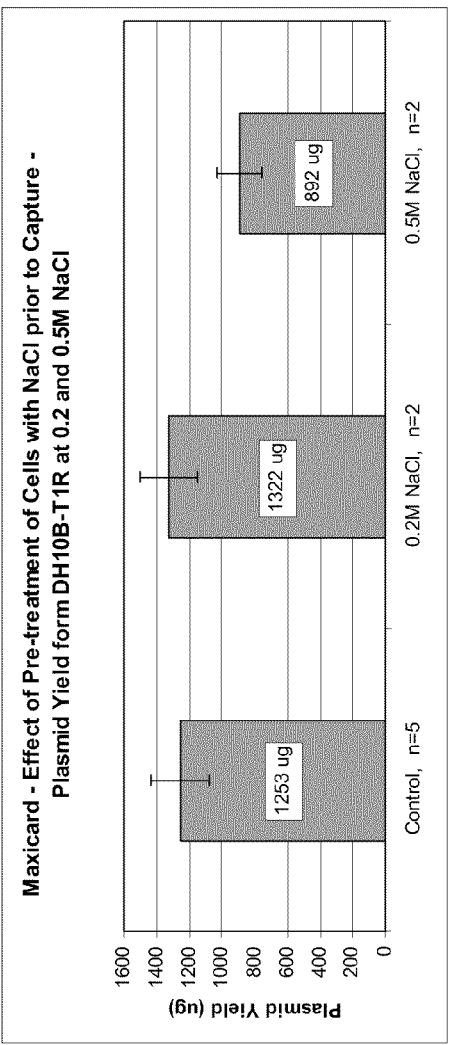
FIGS. 44A & 44B show the results of the nucleic acid purification performed as described in Example 30.

The effect of treating cells using 0.2M NaCl solution versus 0.5 M NaCl solution prior to capture of DH10B-T1R cells was compared and the results of the comparison are shown in FIG. 44A. As shown in FIG. 44A, there was a small increase in the plasmid yield when using 0.2M NaCl solution as compared to the control, while the 0.5M NaCl solution appeared to have a detrimental effect on the plasmid yield.

Figure 44B:
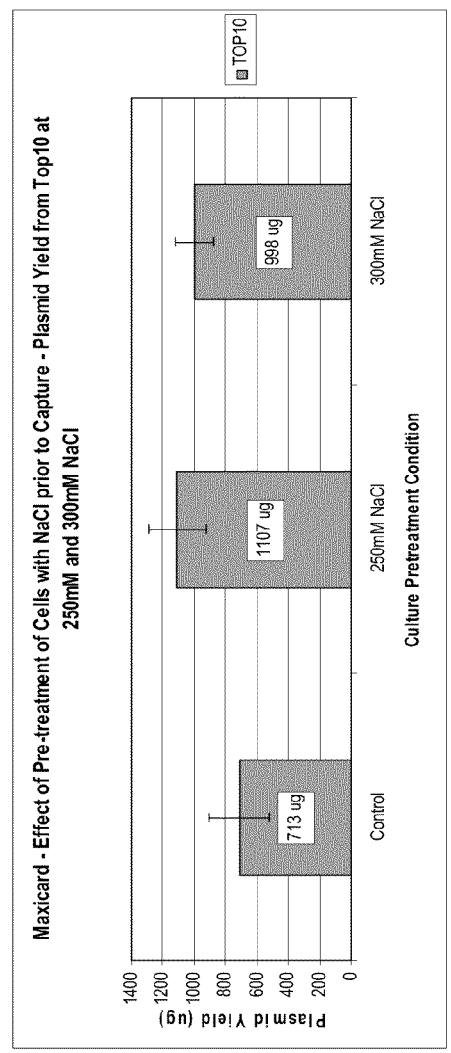

The effect of treating cells using a 250 mm NaCl solution versus using a 300 mm NaCl solution prior to capture of Top10 cells was compared and the result of the comparison are shown in FIG. 44B. As shown in FIG. 44B, both concentrations of NaCl increased the plasmid yields obtained from the Top10 cells as compared to the control, with a 55% increase in the plasmid yield captured when using the 250 mm NaCl concentration and a 40% increase in the plasmid yield captured when using the 300 mm NaCl concentration.

V. Example 31

Cell clumping and the effect of adding NaCl to alleviated cell clumping was tested using the protocol described in Example 29 above. The protocol was run using a bioprocessing system described in FIGS. 1C & 1D and the bioprocessing cartridge shown in FIGS. 16-18.

NaCl pretreatment of cells: 6.5 mL of 5M NaCl was added to 125 mL of bacterial culture located in the reagent tray. Plasmid yield from cells with no salt pretreatment (control) was compared to plasmid yield obtained from cells pretreated with 250 mm NaCl.

Figure 45A:
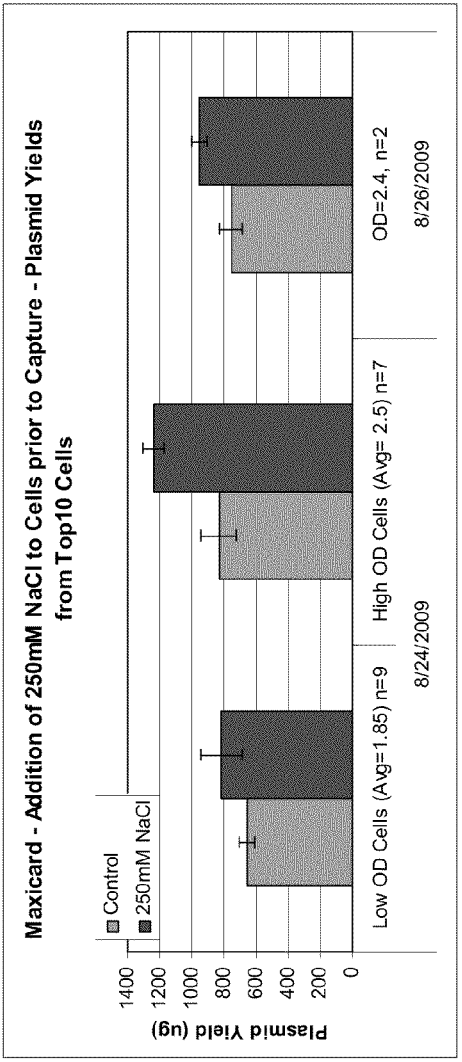
FIGS. 45A & 45B show the results of the nucleic acid purification performed as described in Example 31.
Figure 45B:
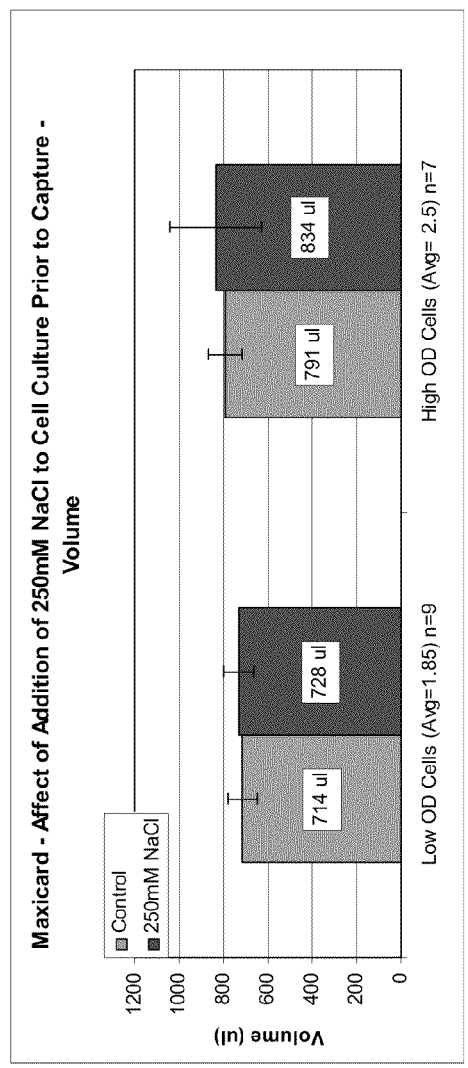

FIG. 45A shows the plasmid yields obtained from low optical density (OD) TOP10 cells (cells with an average density of 1.85), and high optical density TOP10 cells (cells with an average density of 2.4-2.5) as compared to the plasmid yields obtained from TOP10 controls (no salt treatment). As shown in FIG. 45A, the plasmid yield collected for all TOP10 cells increased with the treatment of 250 mM NaCl, as compared to the controls. The volume of the final sample collected after the run remained unaffected by the salt pretreatment, as shown in FIG. 45B.

W. Example 32

Cell clumping and the effect of adding NaCl to alleviated cell clumping was tested using the protocol described in Example 29 above. The protocol was run using a bioprocessing system described in FIGS. 1C & 1D and the bioprocessing cartridge shown in FIGS. 16-18.

NaCl pretreatment of cells: 6.5 mL of 5M NaCl was added to 125 mL of bacterial culture located in the reagent tray. Plasmid yield from cells with no salt pretreatment (control) was compared to plasmid yield obtained from cells pretreated with 250 mm NaCl.

Figure 46:
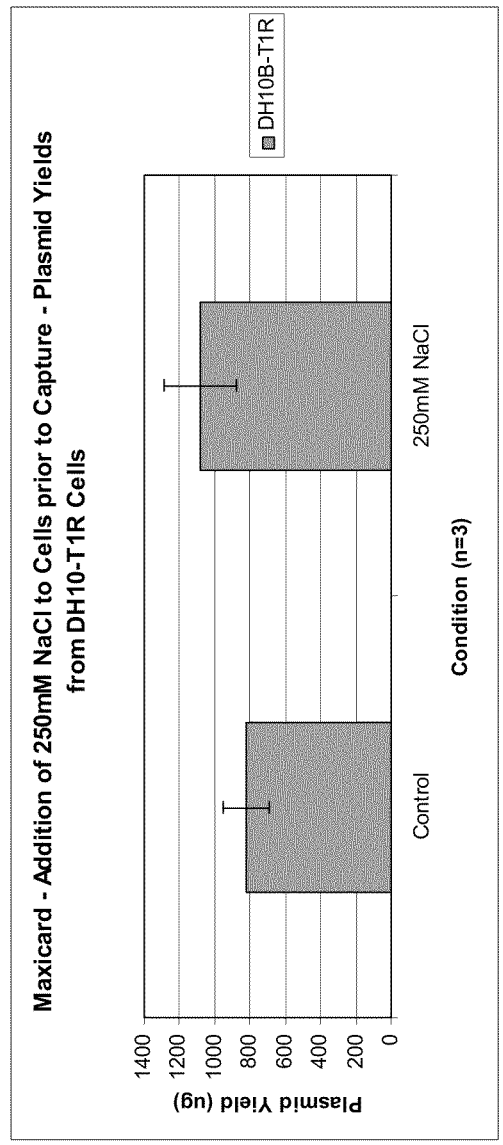
FIG. 46 shows the results of the nucleic acid purification performed as described in Example 32.

FIG. 46 shows the plasmid yields obtained from DH10B-T1R cells pretreated with 250 mm of NaCl as compared to cells with no salt pretreatment. As shown in FIG. 46, the plasmid yield obtained from the DH10B-T1R cells was increased for the 250 mm NaCl pretreated cells versus the control cells.

The terms and expressions which have been employed herein are used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed in part by preferred embodiments, exemplary embodiments and optional features, modification and variation of the concepts herein disclosed may be resorted to by those skilled in the art, and such modifications and variations are considered to be within the scope of this invention as defined by the appended claims. The specific embodiments provided herein are examples of useful embodiments of the present invention and it will be apparent to one skilled in the art that the present invention may be carried out using a large number of variations of the devices, device components, and methods steps set forth in the present description.

All references cited in this application are hereby incorporated in their entireties by reference to the extent that they are not inconsistent with the disclosure in this application. It will be apparent to one of ordinary skill in the art that methods, devices, device elements, materials, procedures and techniques other than those specifically described herein can be applied to the practice of the invention as broadly disclosed herein without resort to undue experimentation. All art-known functional equivalents of methods, devices, device elements, materials, procedures and techniques specifically described herein are intended to be encompassed by this invention.

When a group of materials, compositions, components or compounds is disclosed herein, it is understood that all individual members of those groups and all subgroups thereof are disclosed separately. When a Markush group or other grouping is used herein, all individual members of the group and all combinations and subcombinations possible of the group are intended to be individually included in the disclosure. Every formulation or combination of components described or exemplified herein can be used to practice the invention, unless otherwise stated. Whenever a range is given in the specification, for example, a temperature range, a time range, or a composition range, all intermediate ranges and subranges, as well as all individual values included in the ranges given are intended to be included in the disclosure.

We claim:

1. A bioprocessing cartridge comprising:
    a) at least one bioprocessing chamber configured to contain a solid support;
    b) a plurality of mesoscale and/or microscale process fluid channels in fluid communication with the bioprocessing chamber through at least one pump, wherein the at least one pump is included in or on the bioprocessing cartridge;
    c) a film or foil layer enclosing the at least one bioprocessing chamber, the plurality of mesoscale and/or microscale fluid channels, and the at least one pump; and
    d) a cartridge alignment guide configured to hold the bioprocessing cartridge in a cartridge holder of a bioprocessing device,
wherein said cartridge comprises at least one access valve within a flow path defined by at least one of the plurality of process fluid channels, wherein each of said at least one access valves is located within a flow path between a process fluid connector and the at least one of the plurality of process fluid channels, each process fluid connector configured to fluidly connect the cartridge to one or more fluid containers and wherein said cartridge comprises more than one access valve, wherein each access valve is placed within a flow path between an independent process fluid connector and one of the plurality of process fluid channels, each independent process fluid connector configured to fluidly connect the cartridge to one or more fluid containers.

2. The cartridge of claim 1, wherein said process fluid connectors are configured to connect to said fluid containers via a manifold.

3. The cartridge of claim 1, wherein said process fluid connectors are configured to connect to said fluid containers via aspiration and/or expiration tubes.

4. The cartridge of claim 1, wherein said process fluid connectors are aspiration and/or expiration tubes.

5. The cartridge of claim 1, wherein said cartridge comprises an access valve within each of the flow paths between each of the process fluid connectors and each of the plurality of process fluid channels.

6. The cartridge of claim 1, further comprising at least one process valve in a flow path between the pump and the chamber.

7. The cartridge of claim 1, wherein said cartridge comprises two or more bioprocessing chambers.

8. The cartridge of claim 1, further comprising a plurality of control fluid channels.

9. The cartridge of claim 1, further comprising control fluid connectors connecting to each of said plurality of control fluid channels, each control fluid connector configured to fluidly connect the cartridge to one or more automated control systems.

10. The cartridge of claim 1, wherein said cartridge comprises a dye chamber in fluid communication with at least one process fluid channel, wherein a material within said dye chamber changes color when contacted with a fluid.

11. The cartridge of claim 1, wherein the two or more fluid layers comprise at least a process fluid layer and a control fluid layer.

12. The cartridge of claim 1 further comprising two film or foil layers.

13. The cartridge of claim 1 wherein the mesoscale and/or microscale process fluid channels are formed from one or more substrate layers and the cartridge further comprises one or more additional layers or elements between the one or more the substrate layers.

14. A bioprocessing cartridge comprising:
    a) at least one bioprocessing chamber configured to contain a solid support;
    b) a plurality of mesoscale and/or microscale process fluid channels in fluid communication with the bioprocessing chamber through at least one pump, wherein the at least one pump is included in or on the bioprocessing cartridge;

c) a film or foil layer enclosing the at least one bioprocessing chamber, the plurality of mesoscale and/or microscale fluid channels, and the at least one pump; and d) a cartridge alignment guide configured to hold the bioprocessing cartridge in a cartridge holder of a bioprocessing device, the bioprocessing cartridge comprising a plurality of control fluid channels and further comprising control fluid connectors connecting to each of said plurality of control fluid channels, each control fluid connector configured to fluidly connect the cartridge to one or more automated control systems.

\* \* \* \* \*